(12) United States Patent
Wills et al.

(10) Patent No.: US 9,321,045 B2
(45) Date of Patent: Apr. 26, 2016

(54) CATALYST AND PROCESS FOR SYNTHESISING THE SAME

(71) Applicant: The University of Warwick, Coventry, West Midlands (GB)

(72) Inventors: Martin Wills, Coventry (GB); Katherine Emma Jolley, Coventry (GB); Rina Soni, Coventry (GB)

(73) Assignee: THE UNIVERSITY OF WARWICK, West Midlands (GB)

( * ) Notice: Subject to any disclaimer, the term of this patent is extended or adjusted under 35 U.S.C. 154(b) by 0 days.

(21) Appl. No.: 14/440,140

(22) PCT Filed: Nov. 1, 2013

(86) PCT No.: PCT/GB2013/052869
§ 371 (c)(1),
(2) Date: May 1, 2015

(87) PCT Pub. No.: WO2014/068331
PCT Pub. Date: May 8, 2014

(65) Prior Publication Data
US 2015/0290634 A1    Oct. 15, 2015

(30) Foreign Application Priority Data

Nov. 2, 2012 (GB) .................................. 1219716.6

(51) Int. Cl.
| | | |
|---|---|---|
| *C07F 15/00* | (2006.01) | |
| *B01J 31/22* | (2006.01) | |
| *C07C 29/145* | (2006.01) | |
| *B01J 31/18* | (2006.01) | |
| *B01J 31/16* | (2006.01) | |

(52) U.S. Cl.
CPC .......... *B01J 31/2295* (2013.01); *B01J 31/1658* (2013.01); *B01J 31/1805* (2013.01); *C07C 29/145* (2013.01); *C07F 15/0046* (2013.01); *B01J 2231/643* (2013.01); *B01J 2531/821* (2013.01)

(58) Field of Classification Search
CPC . C07F 15/0046; C07C 29/145; B01J 31/2295
USPC ............................................ 556/137; 568/715
See application file for complete search history.

(56) References Cited

U.S. PATENT DOCUMENTS

2012/0123142 A1* 5/2012 Dyke ................... B01J 31/1805
556/137

FOREIGN PATENT DOCUMENTS

| WO | 2010106364 | 9/2010 |
|---|---|---|
| WO | 2012026201 | 3/2012 |
| WO | 2012147944 | 11/2012 |

OTHER PUBLICATIONS

PCT Search Report prepared for PCT/GB2013/052869, mailed Feb. 10, 2014.
Morris, David J., Aidan M. Hayes, and Martin Wills. "The "reverse-tethered" ruthenium (II) catalyst for asymmetric transfer hydrogenation: further applications." The Journal of organic chemistry 71.18 (2006): 7035-7044.
Jolley, Katherine E., et al. "Application of tethered ruthenium catalysts to asymmetric hydrogenation of ketones, and the selective hydrogenation of aldehydes." Advanced Synthesis & Catalysis 354. 13 (2012): 2545-2555.
Touge, Taichiro, et al. "Oxo-tethered ruthenium (II) complex as a bifunctional catalyst for asymmetric transfer hydrogenation and H2 hydrogenation." Journal of the American Chemical Society 133.38 (2011): 14960-14963.

* cited by examiner

*Primary Examiner* — Porfirio Nazario Gonzalez
(74) *Attorney, Agent, or Firm* — Brannon Sowers & Cracraft PC

(57) ABSTRACT

The invention relates to a method for synthesizing tethered ruthenium catalysts and novel tethered ruthenium catalysts obtainable by this methods. The method involves carrying out an "arene swapping" reaction avoiding the requirement to use complicated techniques making use of unreliable Birch reductions and unstable cyclodienyl intermediates.

22 Claims, 21 Drawing Sheets

CATALYST AND PROCESS FOR SYNTHESISING THE SAME

CROSS-REFERENCE TO RELATED APPLICATIONS

This application is a U.S. national application under 37 C.F.R. §371(b) of International Application Serial No. PCT/GB2013/052869, filed Nov. 1, 2013, which claims the benefit under 35 U.S.C. 119(a) of GB Patent Application No. 1219716.6, filed Nov. 2, 2012, the entire disclosures of which are incorporated herein by reference.

FIELD OF INVENTION

The invention relates to a process for synthesising catalysts for asymmetric catalysis using a ligand swapping reaction and novel compounds made according to said process and also their use in hydrogenation reactions.

BACKGROUND TO THE INVENTION

Asymmetric catalysis is an important area of chemistry, invaluable in the production of enantiomerically enriched products. The manufacture of pharmaceuticals and specialised chemical compounds are two particular industries where stereo-selective synthesis is often essential.

Hydrogenation reactions are used in a variety of synthetic methods and asymmetric control of hydrogenation has been well studied. In particular, catalysts for the asymmetric reduction of carbonyl and imino groups have been known for many years.

Ruthenium η-6 arene complexes were first reported as suitable catalysts for asymmetric hydrogenation by Noyori, and co-workers (S. Hashiguchi, A. Fujii, J. Takehara, T. Ikariya, R. Noyori, *J. Am. Chem. Soc.* 1995, vol 117, 7562-7563). These catalysts have been extensively tested and commercialised and are effective at the asymmetric reduction of ketones and imines to alcohols and amines respectively using a number of reducing agents.

Wills reported, in 2005, an improvement of the Noyori catalyst, which demonstrates increased reactivity on a wider range of substrates (A. M. Hayes, D. J. Morris, G. J. Clarkson and M. Wills, *Am. Chem Soc,* 2005, vol 127, 7318-7319). Wills catalysts, or so called 'tethered' catalysts, comprise a ligand having an η-6 arene group co-ordinated to a metal centre, wherein the arene group is also covalently linked to a second portion which co-ordinates to the remaining available positions around the metal centre.

Various synthetic routes have been proposed to make these complexes, many of which require multi-step reactions via a range of complex mechanisms. One such synthesis requires i) Birch reduction of an alcohol using an onerous combination of sodium metal and liquid ammonia, ii) conversion of the alcohol to an aldehyde using Swern oxidation, iii) reductive coupling of the aldehyde with the diamine component, iv) complexation of the product with ruthenium trichloride and v) conversion of the initially formed dimer to a monomer.

An alternative synthesis requires i) Birch reduction of an alcohol, ii) conversion of the alcohol to the tosylate, triflate, mesylate or related reagent, iii) coupling with the diamine component, iv) complexation of the product with ruthenium trichloride and v) conversion of the initially formed dimer to a monomer. Although some of these reactions can be 'telescoped' into a shorter practical sequence by performing the last two steps in a 'one-pot' process, many of these processes are undesirable.

Further, many of these reactions require the presence of a cyclodienyl intermediate in order for the η-6 arene ring to form and co-ordinate with the metal centre. This cyclodienyl intermediate limits the range of substituents that can be arranged around the arene ring as electron donating groups will cause aromatisation of the ring prior to co-ordination with the metal centre thereby preventing the desired complex from forming.

Various attempts have been made to synthesise these complexes using intramolecular ring swapping reactions such as M. Ito, H. Komatso, Y. Endo and T. Ikariya, *Chem. Lett.* 2009, 38, 98-99. However, there is no evidence that such approaches do not work with larger multidentate ligand counterparts The invention is intended to overcome or ameliorate at least some of the problems outlined above.

SUMMARY OF THE INVENTION

There is provided in a first aspect of the invention, a process for synthesising a compound according to general formula (I), the process comprising the steps of reacting a compound according to general formula (IIa) or (IIb) with the compound according to general formula (III),

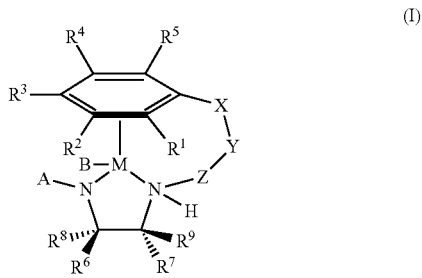

(I)

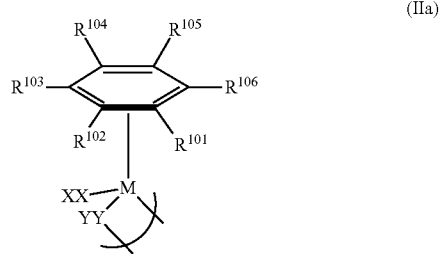

(IIa)

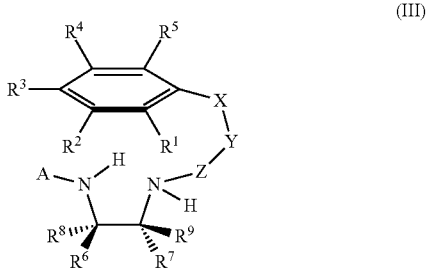

(III)

-continued

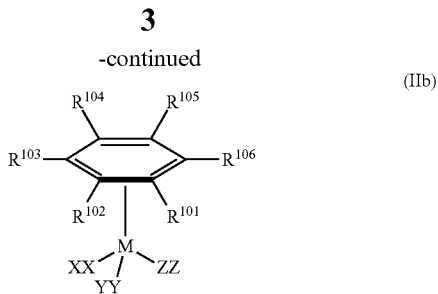

(IIb)

wherein $R^1$-$R^5$, $R^6$-$R^9$ and $R^{101}$-$R^{106}$ each independently, or in combination with another of said substituents ($R^1$-$R^5$, $R^6$-$R^9$ and $R^{101}$-$R^{106}$) are selected from: H, halide, alkyl, alkenyl, alkynyl, alkoxy, hydroalkyl, haloalkyl, carboalkyl, aryl, aryloxy, CH$_2$Ar (where Ar is aryl), acyl, carboxy (C═O), alkoxycarbonyl, thiocarbonyl (═S), cyano (CN), hydroxyl, thiol, alkylthiol, amino, acylated amino, NO$_2$, silyl, SO$_2$R$^{10}$ (where $R^{10}$ is defined as for $R^{101}$-$R^{106}$); A is selected from: H, $R^{11}$, SO$_2$R$^{11}$, SOR$^{11}$, SO$_2$NR$^{11}$R$^{12}$, P(O)($R^{11}$R$^{12}$), P(O)(OR$^{11}$)(OR$^{12}$), CO$_2$R$^{11}$, wherein $R^{11}$ and $R^{12}$ are defined as for $R^{10}$; B is selected from: H, halide, trifluoromethylsulfonyl, alkylsulfonate, trifluoromethylsulfonate, arylsulfonate, carboxylate or acetoxy group; M is a metal atom/ion selected from: ruthenium, rhodium, osmium, iridium and iron (typically ruthenium or rhodium); XX-ZZ are each independently selected from: H, halide, hydroxyl, amino or any other atom or group of atoms which can form a stable complex; at least one of X, Y and Z is present and each is independently, or in combination with each other, selected from one or more of the groups: CH$_2$, O, S, NH, CHR$^{11}$CR$^{11}$R$^{12}$ (where $R^{11}$-$R^{12}$ are defined as for $R^{101}$-$R^{106}$) adjacent groups may form unsaturated carbon-carbon bonds for example by being alkenyl (—CH═CH—) or as part of a cyclic structure, such as an aryl group or combinations thereof and the total linear length of the chain defined by 'X-Y-Z' is two to four atoms, typically 3 atoms; or a salt thereof. This process provides a simple and efficient synthesis for tethered metal catalysts which allows for a broad range of substituents to be incorporated onto the η-6 arene ring. Enantiomers of formulae I, IIa, IIb and/or III are also included in the scope of the invention.

The term 'alkyl' is intended to encompass substituted or unsubstituted aliphatic, linear and cyclic saturated carbon chains as well as branched saturated carbon chains. Typically, the alkyl groups used in the invention are between $C_1$ to $C_{10}$, more typically between $C_1$ to $C_8$ and even more typically $C_1$ to $C_5$. The terms 'alkenyl' and 'alkynyl' are intended to mean an alkyl group as defined above having at least one carbon-carbon double bond (C═C) or at least one carbon-carbon triple bond (C≡C) respectively. The term 'aryl' is intended to refer to an aromatic ring structure. This may include one or more fused rings and the ring or rings may each independently be 5-, 6-, 7-, 8- or 9-membered rings. Further, said ring structures may also comprise one or more heteroatoms. Typically, one or two heteroatoms are included in the ring and the heteroatoms are typically selected from nitrogen, oxygen and sulphur. Most typically, the heteroatom is nitrogen or oxygen. Typically, the aryl groups will be a single aromatic ring and even more typically, the ring may be a 5-, or 6-membered ring.

Groups $R^1$-$R^5$ and $R^{101}$-$R^{106}$ may form substituents in combination with one another. One or more of $R^1$ and $R^2$, $R^2$ and $R^3$, $R^3$ and $R^4$, $R^4$ and $R^5$, $R^6$ and $R^7$, $R^6$ and $R^8$, $R^6$ and $R^9$, $R^8$ and $R^7$, $R^8$ and $R^9$, $R^7$ and $R^9$, $R^{101}$ and $R^{102}$, $R^{102}$ and $R^{103}$, $R^{103}$ and $R^{104}$, $R^{104}$ and $R^{105}$, $R^{105}$ and $R^{106}$, $R^{101}$ and $R^{106}$ may be linked to form a cycloalkyl, cycloalkenyl, cycloalkynyl or aryl group. For example, neighbouring groups may together define an aromatic ring thereby creating a ligand comprising a fused ring structure.

The groups 'XX-ZZ' described in general formulae (IIa) and (IIb) are not particularly limited as they are believed to not play a significant role in the reaction according to the claimed invention. Accordingly, XX-ZZ is any group capable of forming a stable complex, or in other words, that is capable of co-ordinating to the metal centre without destabilising the η-6 arene complex, XX-ZZ are typically monodentate ligands. It is typically the case that XX-ZZ is a halide and even more typically chloride. However, XX-ZZ may also often be OH, NH$_3$ or C═O or a trifluoromethylsulfonyl group, an alkylsulfonate, trifluoromethylsulfonate or aryl-sulfonate group, any carboxylate group including an acetoxy group or a hydrogen atom. XX-ZZ could also be a neutral molecule such as triphenylphosphine or a solvent molecule for example acetonitrile, dichloromethane, dimethylsufoxide, methanol, ethanol or another commonly used solvent.

The term 'halide' is intended to cover fluoride, chloride, bromide and iodide. The term 'amino' is intended to encompass primary, secondary and tertiary amino groups.

Typically, the reaction is performed in an organic solvent. The solvent may comprise a halogenated solvent such as a halogenated organic solvent, and it is often the case that the solvent will comprise chlorobenzene, dichloromethane, 1,2-dichloroethane, xylene or a combination thereof. Typically, the solvent will comprise at least 90% chlorobenzene, dichloromethane, 1,2-dichloroethane, xylene or a combination thereof by mass of the total solvent. Typically the solvent is chlorobenzene, dichloromethane or a combination thereof and even more typically the solvent is chlorobenzene. The inventors have surprisingly found that this solvent system is particularly effective as a solvent for the reaction.

The typical duration of the reaction necessary to produce the product depends on the choice of solvent used. However, the duration is usually within the range of 2 to 50 hours. In particular, where the solvent is dichloromethane it is typically the case that the reaction time will be in the range of 40 to 50 hours and where the solvent is chlorobenzene it is typically the case that the reaction time is between 2 to 5 hours. It will be appreciated by the skilled person that the duration of the reaction will vary depending on the exact ratio of solvents, where a combination of solvents are used, and the temperature at which the reaction is carried.

The temperature at which the reaction is performed is typically in the range of 25° C. to 140° C., even more typically is 50° C. to 140° C. and may also be in the range of 75° C. to 120° C. It is often the case that the reaction will be conducted in the range of 75° C. to 90° C. The inventors have unexpectedly found that the reaction of the present invention proceeds most efficiently when performed within these temperature windows and minimises the quantity of impurities generated.

The reaction may be carried out with a mild inorganic base. A mild inorganic base such as calcium hydroxide, sodium bicarbonate or potassium carbonate may be added to the reaction. However strong bases, such as triethylamine or sodium hydroxide are typically not used as these tend to provide lower yields of the catalyst.

The metal centre of the complex in the catalysts of the invention is typically ruthenium. Whilst other metals can be used with the invention, ruthenium has been found to produce the most effectively catalysts. The catalysts of the invention are typically used in the asymmetric hydrogenation. In particular, the catalysts may be used in the asymmetric hydrogenation of C=O and C=N bonds. Typically, the catalysts are used in the asymmetric reduction of ketones.

The complexes may contain multiple chiral centres, or a single chiral centre, and may be prepared in either enantiomerically-enriched or racemic form.

It is usually the case that the total linear length of the chain defined by 'X-Y-Z' is three atoms. Groups X, Y and Z each independently comprise, or in combination with each other, one or more of the groups selected from: $CH_2$, $CHR^{11}$ and $CR^{11}R^{12}$ or one or more adjacent groups may form an alkenyl moiety (—CH=CH—). Typically, X, Y and Z are each $CH_2$. $R^{11}$ and $R^{12}$ may form substituents in combination with one another. For example, neighbouring groups may together define an aromatic ring thereby creating a tethering portion wherein carbons in the chain form the edge of an aromatic ring. The inventors have found that ligands having a tether portion (X-Y-Z) with a length of two, three and four atoms, demonstrate optimum catalytic activity.

The combined electron withdrawing effect generated by $R^{101}$-$R^{106}$ may be greater than that generated by $R^1$-$R^5$. Usually, at least one of $R^1$-$R^5$ is an alkoxy group, and typically at least one of $R^1$-$R^5$ is a methoxy group. Even more typically one, two or three of $R^1$-$R^5$ are a methoxy group. The reaction of the present invention has been found to proceed more efficiently where the electron density around the ring of the compound according to general formulae (IIa) and (IIb) is less than that on the ring of the compound according to general formulae (III). Without wishing to be bound by theory, it seems that a reduction in the electron density of the ring shown in general formulae (IIa) and (IIb) relative to the ring shown in general formulae (III) promotes the 'ring swapping' reaction.

It is often the case that at least one of $R^{101}$-$R^{106}$ is an electron withdrawing group and at least one of $R^{101}$-$R^{106}$ may be an ester group. Usually, at least one of $R^{101}$-$R^{106}$ is $CO_2Et$. Ester groups can be incorporated on the phenyl ring easily and provide a good electron withdrawing effect, decreasing electron density of the ring.

Typically, $R^6$=$R^7$=Ph or $C_4$ alkyl or $R^8$=$R^9$=Ph or $C_4$ alkyl. Typically, the $C_4$ alkyl is a tertiary butyl group. In order for the catalysts to provide optimal stereo-selective reduction, it is useful to functionalise the pendant, diamine portion of the ligand with bulky groups on either side of the nitrogen groups. This directs the incoming substrate and reagents towards a particular orientation, favouring a specific enantiomer.

The groups XX-ZZ are typically monodentate ligands and are often halides and even more typically are chloride. XX-ZZ may also often be —OH, $NH_3$ or C=O or a trifluoromethylsulfonyl group, an alkylsulfonate, trifluoromethylsulfonate or aryl-sulfonate group, any carboxylate group including an acetoxy group or a hydrogen atom. As mentioned above, there is no particular limitation on the choice of ligand which XX-ZZ can be however, chloride is readily available and reasonable small and therefore does not interfere with the reactive portions of the catalyst and forms a stable complex with the metal centre.

A is typically selected from $SO_2Ar$, $SO_2R$ (wherein Ar is aryl and R is alkyl as defined above) and even more typically A is $SO_2pTol$.

Often, the group B may be a monodentate ligand and may be a halide and is typically is chloride. The group B is usually one of XX-ZZ which has not been displaced by co-ordination of the ligand. As such, B is also typically chloride as this is readily available and reasonable small and therefore does not interfere with the reactive portions of the catalyst and forms a stable complex with the metal centre.

Further, it may be the case that the reaction is performed with exposure to a microwave source. Typically, the microwaves to which the reaction is exposed are in the range of 20 W to 200 W and more typically are in the range of 40 W to 100 W. There is no particular limit on the power of the microwave source but this is usually restricted so that it does not causes excessive evaporation of the reaction solvent or lead to an excessive rise in temperature. The duration of time for which the reaction is irradiated is usually in the range of 10 seconds to 30 minutes and more often will be in the range of 1 minute to 10 minutes. Further, the power of the microwave radiation can be increased or decreased, either gradually or incrementally, as required throughout the reaction. The power need not be constant throughout a single period of irradiation.

The reaction may be carried out alternating the conditions between exposure and non-exposure to microwaves. As such, a single reaction may experience several periods of microwave radiation and relaxation.

There is also provided in a second aspect of the invention, a compound according to general formula (IV)

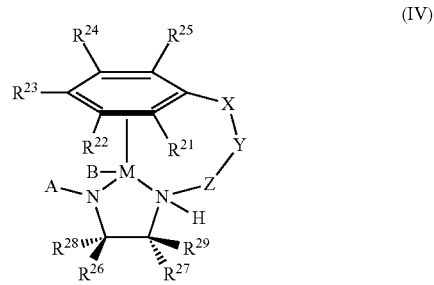

(IV)

wherein, $R^{21}$-$R^{25}$ each independently, or in combination with another of said substituents ($R^{21}$-$R^{25}$) form, an electron rich or electron donating group and are selected from: H, alkylaryl, alkoxy, aryloxy, acyloxy, hydroxy, amino, acyl amino, thiol, alkylthiol; and wherein, $R^{26}$-$R^{29}$ are defined as for $R^{101}$-$R^{106}$; B is selected from: H, halide, trifluoromethylsulfonyl, alkylsulfonate, trifluoromethylsulfonate, aryl-sulfonate, acetoxy group; and A, B, M, XX-ZZ, X, Y, Z are defined as above.

It has been found by the inventors that the compounds having these substituents can be manufactured by the process according to the claimed invention but are not believed to be possible to synthesise by methods disclosed in the prior art. Without wishing to be bound by theory, it is believed that electron rich substituents such as $R^{21}$-$R^{25}$ destabilise the cyclodienyl intermediate used in the processes of the prior art. As such, these compounds are not accessible via conventional methods and provide unique catalytic properties.

Typically, X, Y and Z each independently comprise one or more of the groups selected from: $CH_2$, $CHR^{31}$ and $CR^{31}R^{32}$. Even more typically, X, Y and Z are each $CH_2$. The inventors have found that a 'tethering portion' having a length the structure $(CH_2)_3$ provides optimal catalytic activity.

Groups $R^{21}$-$R^{25}$ and $R^{26}$-$R^{29}$ may form substituents in combination with one another. One or more of $R^{21}$ and $R^{22}$, $R^{22}$ and $R^{23}$, $R^{23}$ and $R^{24}$, $R^{24}$ and $R^{25}$, $R^{26}$ and $R^{27}$, $R^{26}$ and $R^{28}$, $R^{26}$ and $R^{29}$, $R^{28}$ and $R^{27}$, $R^{28}$ and $R^{29}$, $R^{27}$ and $R^{29}$ may be linked to form a cycloalkyl, cycloalkenyl, cycloalkynyl or aryl group. For example, neighbouring groups may together define an aromatic ring thereby creating a ligand comprising a fused ring structure.

It is usually the case that at least one of $R^{21}$-$R^{25}$ is an alkoxy group and typically, at least one of $R^{21}$-$R^{25}$ is a methoxy group and even more typically one, two or three of $R^{21}$-$R^{25}$ is a methoxy group. The oxygen atom in the alkoxy or methoxy substituent is capable of donating electrons into the ring and the methoxy group is typically used as it is small and therefore provides minimal hindrance to other substituents around the ring.

Usually, $R^{26}$=$R^{27}$=Ph or alkyl and it may be the case that $R^{28}$=$R^{29}$=Ph or alkyl. Further, XX-ZZ may be halides and are typically chloride. B is also typically a halide and may be chloride.

It is typically the case that substituents $R^{22}$ and $R^{24}$ are hydrogen and substituents $R^{21}$, $R^{23}$ and $R^{25}$ are not hydrogen. Substitution onto the arene ring at the $R^{22}$ and $R^{24}$ positions is synthetically more difficult due to directing effects during preparation of the ligand.

Typically $R^{21}$-$R^{25}$ and XYZ are not in the following combinations:

(i) XYZ do not together make a 3 carbon linear chain in combination with $R^{21}$-$R^{25}$ forming a para-methyl substitution.

(ii) XYZ do not together make a 3 carbon linear chain in combination with $R^{21}$-$R^{25}$ forming a 3,5 dimethyl substitution or (iii) XYZ do not together make a 4 carbon linker in combination with $R^{21}$-$R^{25}$ forming a 4-Me substitution; wherein the remaining $R^{21}$-$R^{25}$ are H.

The invention is typically selected from:

(a)

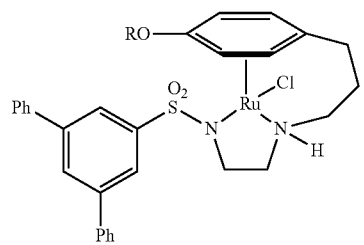

(b)

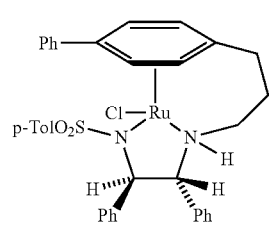

(c)

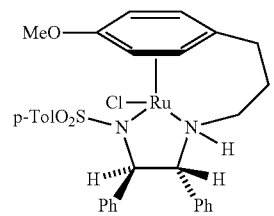

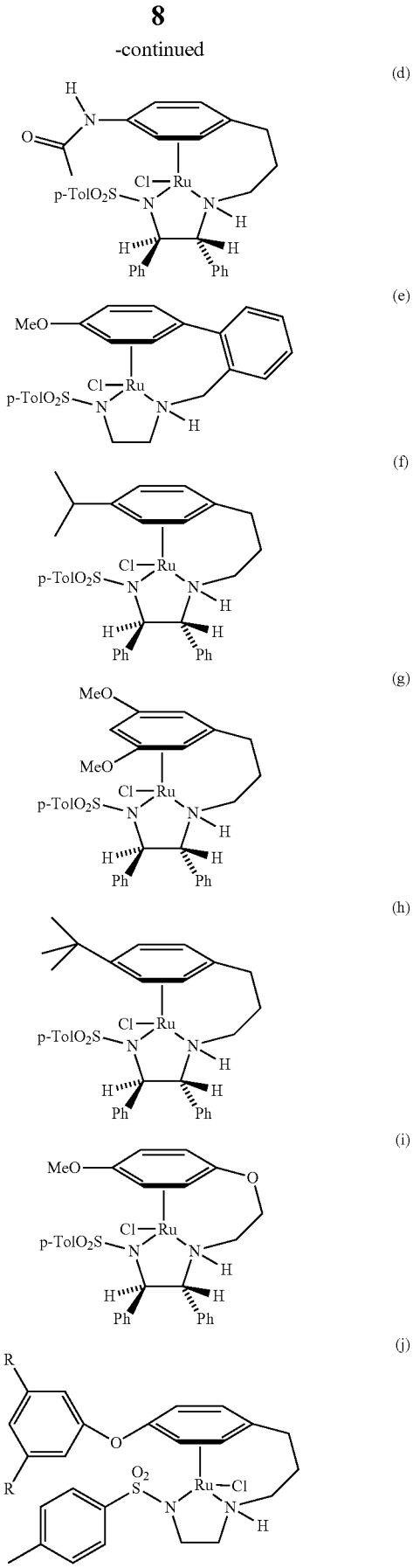

-continued

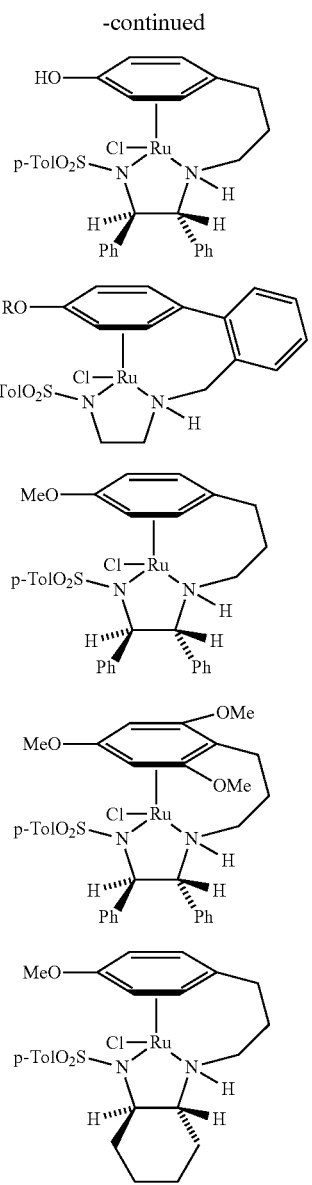

or a salt thereof and/or a combination thereof.

There is also provided in a third aspect of the invention, a method of carrying out a hydrogenation reaction comprising the use of a compound according to second aspect of the invention to catalyse the hydrogenation of a substrate. Typically, the hydrogenation is an asymmetric hydrogenation. Typically the substrate will be a compound containing one or more C=O bonds and/or one or more C=N bonds.

BRIEF DESCRIPTION OF THE DRAWINGS

Table 1a—shows results for asymmetric transfer hydrogenation of ketones using (R,R) '4-methoxy' SRC 834(1) and (R,R) '3,5-dimethoxy' SRC 835(1) catalysts in FA:TEA (2M solution of ketone) at 60° C. using S/C ratio 1000/1.

Table 1b—shows the results of asymmetric transfer hydrogenation of acetophenone and acetylcyclohexane using five novel catalysts (2M) in FA:TEA at 28° C. using complexes at S/C ratio 100/1.

Tables 2a to 2e—shows reductions using hydrogen gas and methanol for different substrates.

Table 3a—shows comparative results for hydrogenation for tethered (R,R) catalysts for a range of substrates.

Table 3b—shows comparative results for hydrogenation for p-OMe and di-OMe 3C tethered (R,R) catalysts.

Table 4—shows asymmetric transfer hydrogenation of ketones (2M) in FA:TEA at 28° C. using a range of tethered complexes at a substrate/catalyst (S/C) ratio 100/1.

Table 5—shows ATH of acetophenone using (R,R) 4-methoxy, (R,R) 3,5-dimethoxy, (R,R)/(S,S) 3C-teth and catalysts TEG 4-OMe in HCOONa/H$_2$O/MeOH at 60° C./40° C. using S/C ratio 100/1, 500/1.

Table 6—shows ATH of ketones using (R,R) 4-methoxy (R,R) 3,5-dimethoxy (R,R)/(S,S) 3C-teth and catalysts TEG 4-OMe in HCOONa/H$_2$O/MeOH at 60° C. using S/C ratio 100/1. Catalysts are as defined in Table 2. Noyori's catalyst is [Ru(p-cymene)(TsDPEN)Cl].

Table 7—shows ATH of amino acetophenone using (R,R) 4-methoxy, (R,R) 3,5-dimethoxy, (R,R)/(S,S) 3C-teth catalysts. Catalysts are as defined in Table 2. Noyori's catalyst is [Ru(p-cymene)(TsDPEN)Cl].

Table 8—shows ATH and APH of acetophenone using polymer supported tethered catalysts.

Table 9—shows ATH of acetophenone using polymer supported ruthenium complexes.

Table 3b—shows comparative results for hydrogenation for p-OMe and di-OMe 3C tethered (R,R) catalysts.

Figure 1:
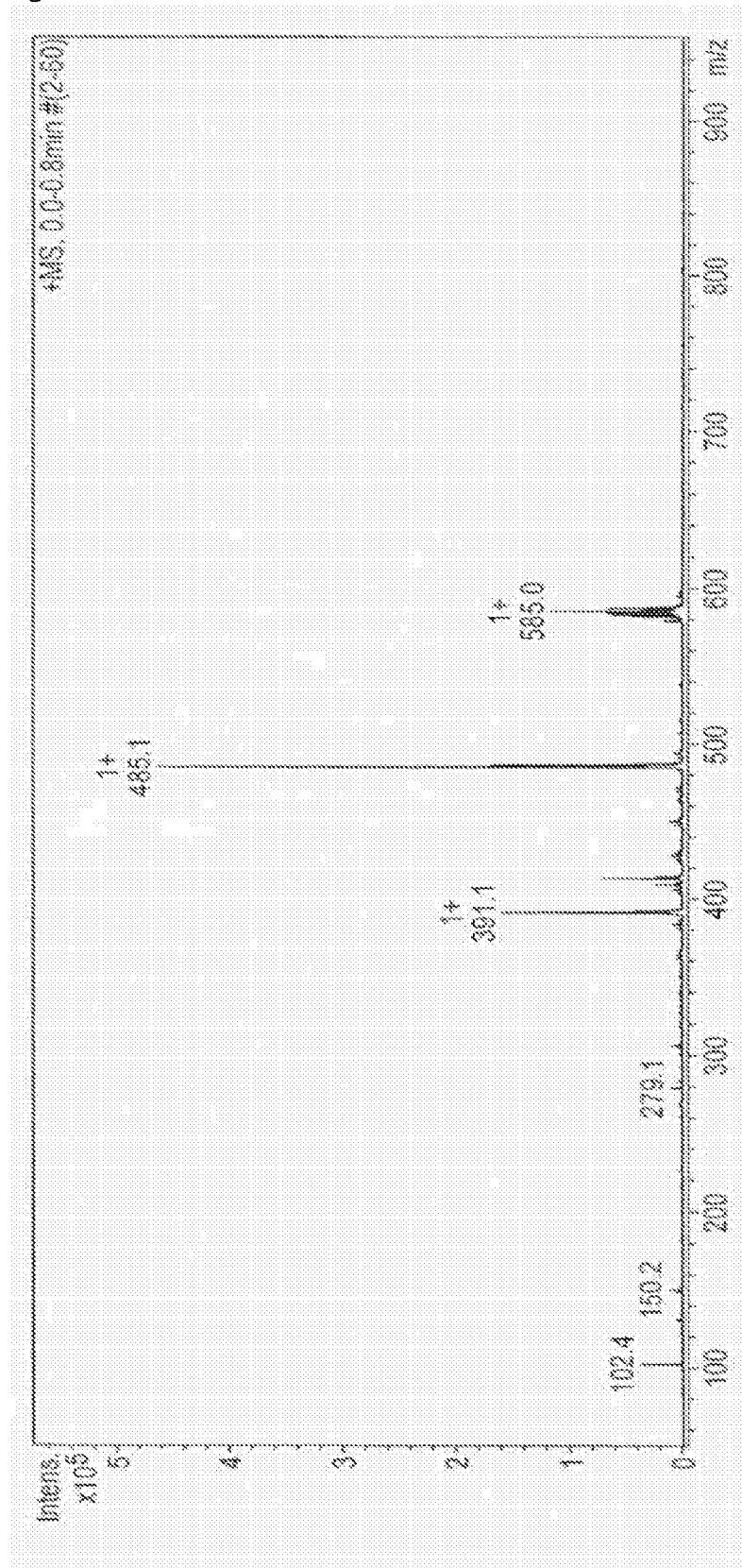

FIG. 1—shows an ESI-MS which illustrates the conversion of ligand to tethered complex, without formation of the unwanted bidentate complex described on page 35.

Figure 2:
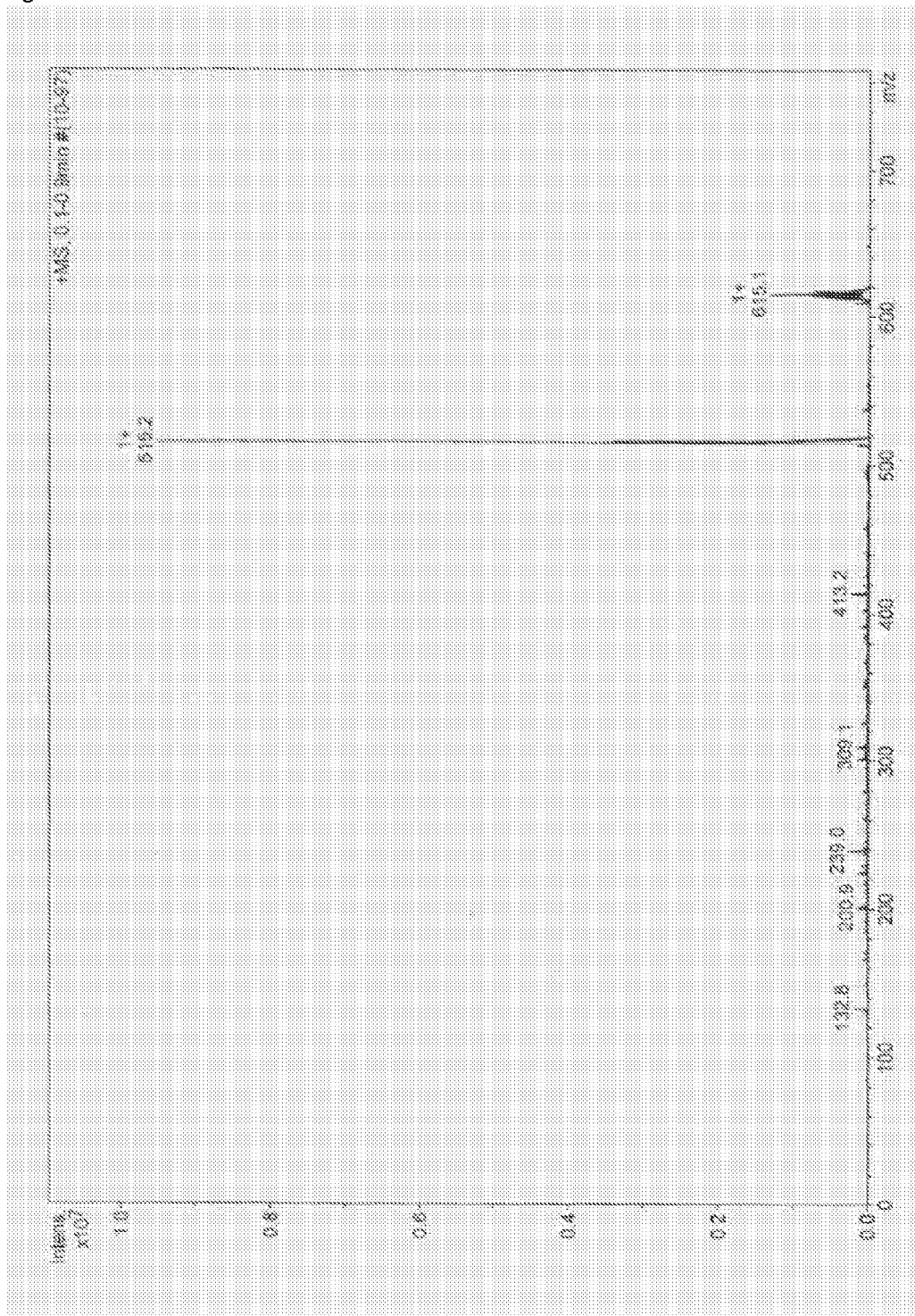

FIG. 2—shows an ESI-MS of an example of 4-methoxy compound after 51.5 h—heating in DCM, 90° C. described on page 35.

Figure 3:
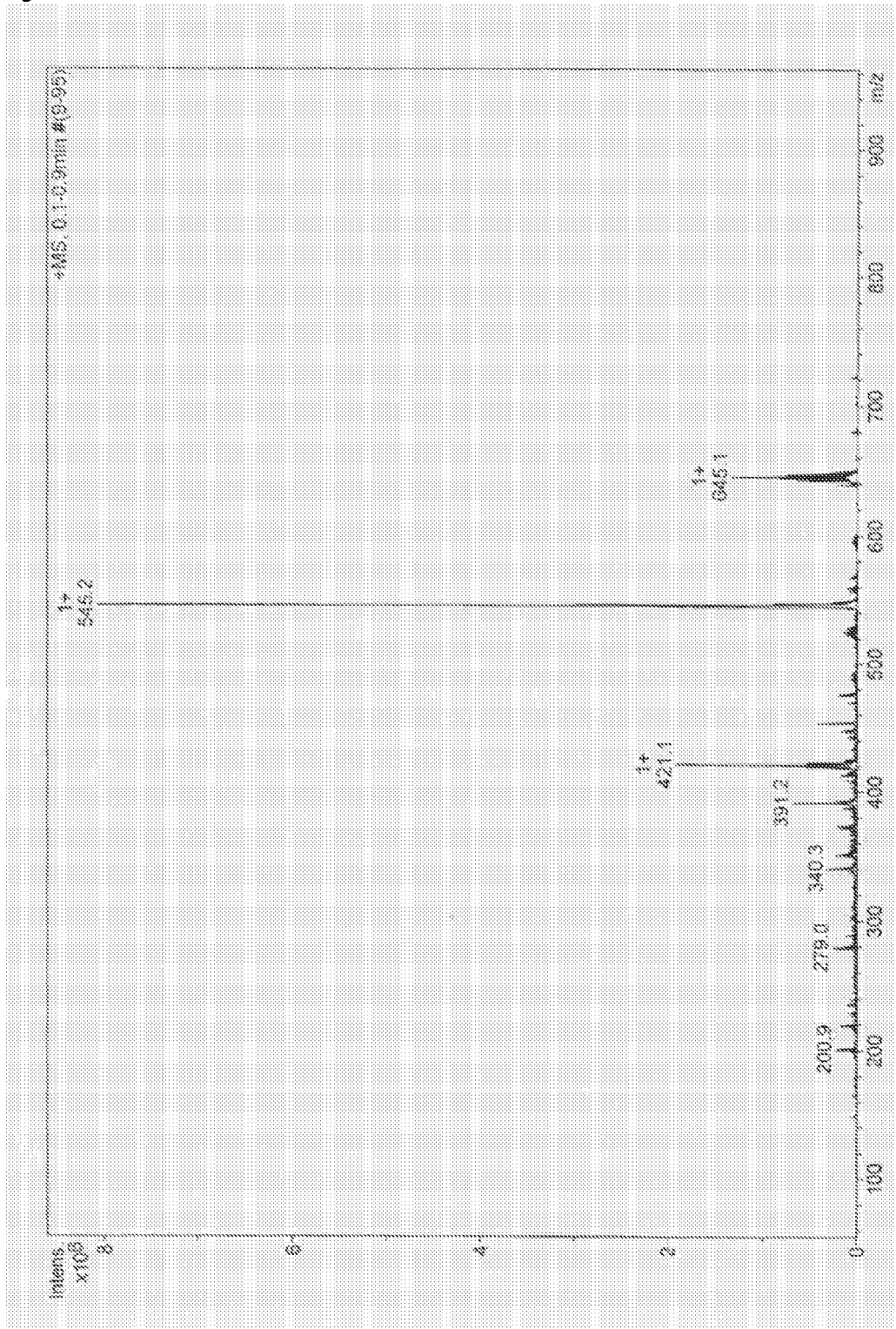

FIG. 3—shows an ESI-MS of an example of 2,4-Dimethoxy ESI-MS after 48 h heating in DCM, 90° C. described on page 36.

Figure 4:
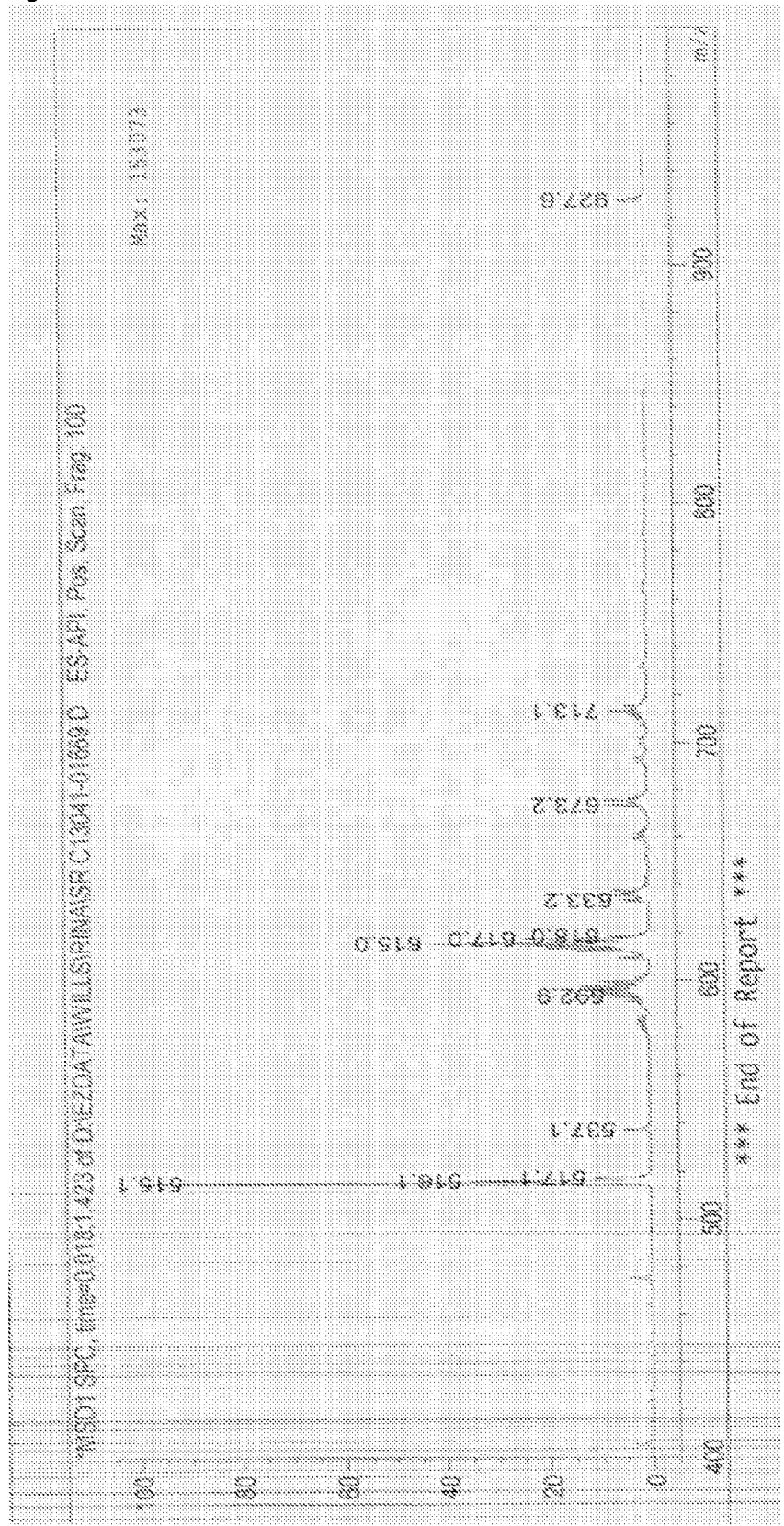

FIG. 4—shows an ESI-MS of a 1st run of the reaction on page 62 under the following conditions: Power=40 W, Temp=90° C., RAMP=1 min, Hold=10 min.

Figure 5:
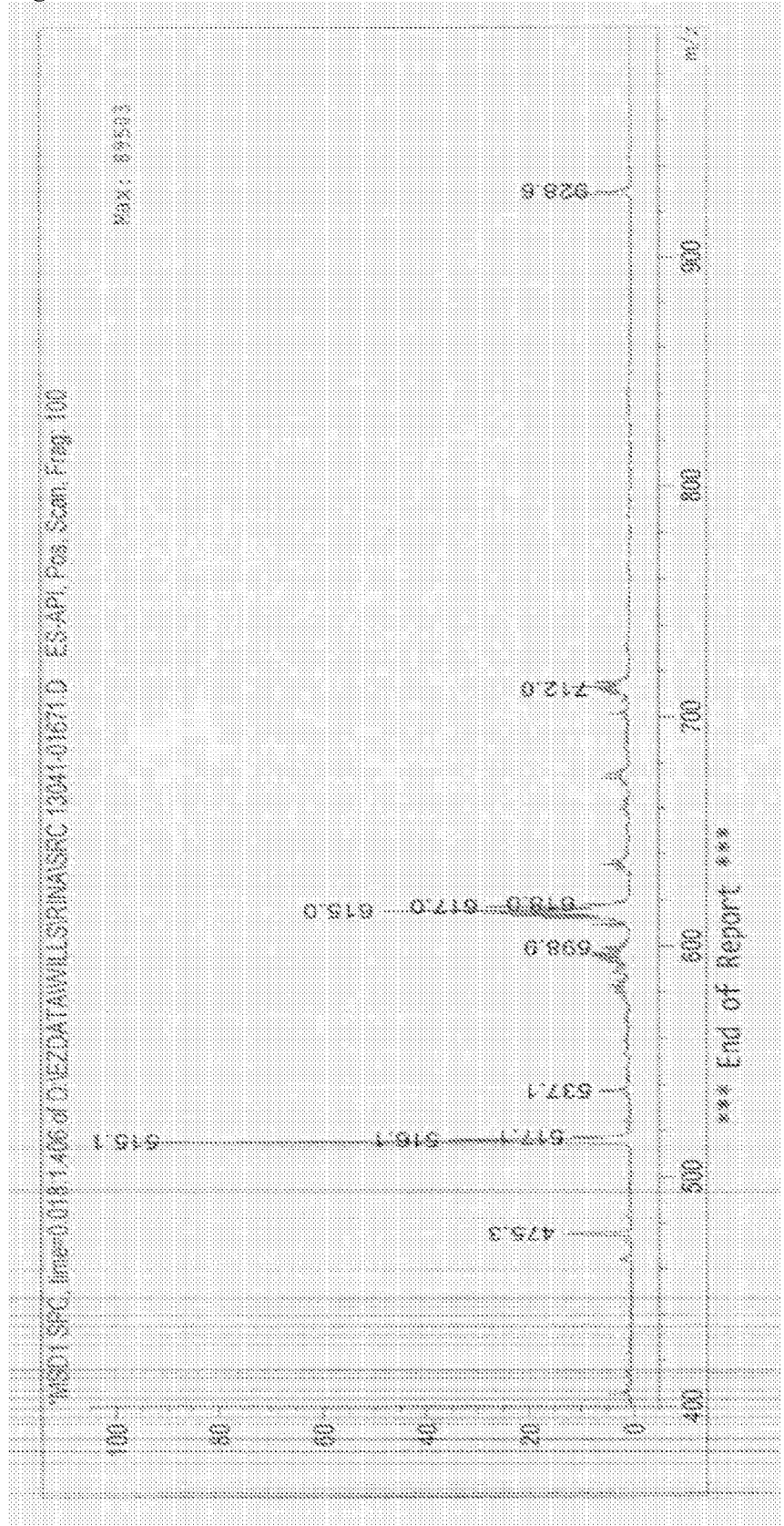

FIG. 5—shows an ESI-MS of a 2nd run of the reaction on page 63 under the following conditions: Power=40 W, Temp=90° C., RAMP=1 min, Hold=10 min.

Figure 6:
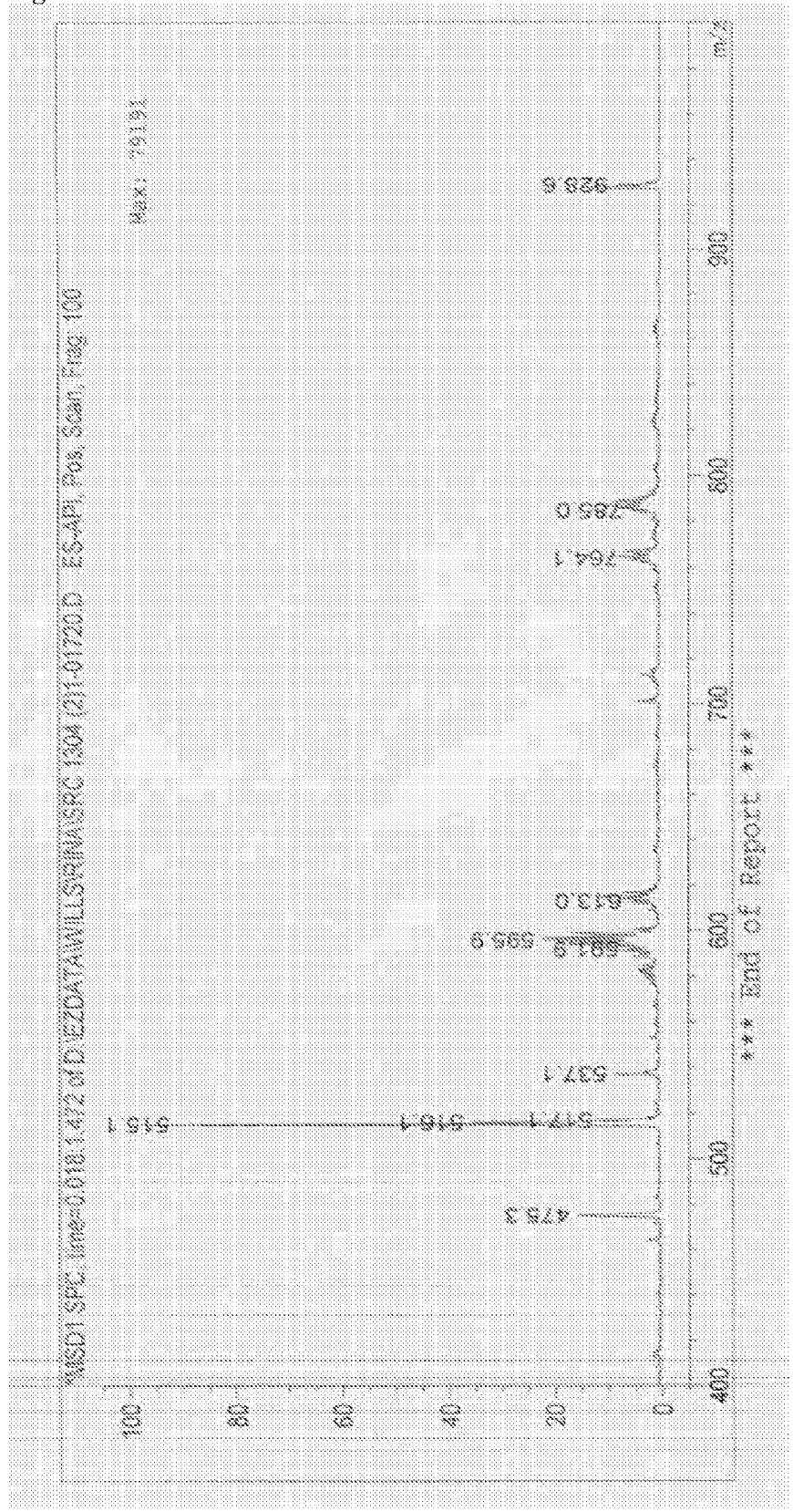

FIG. 6—shows an ESI-MS of a 1st run of the reaction on page 63 under the following conditions: Power=40 W, Temp=90° C., RAMP=1 min, Hold=10 min.

Figure 7:
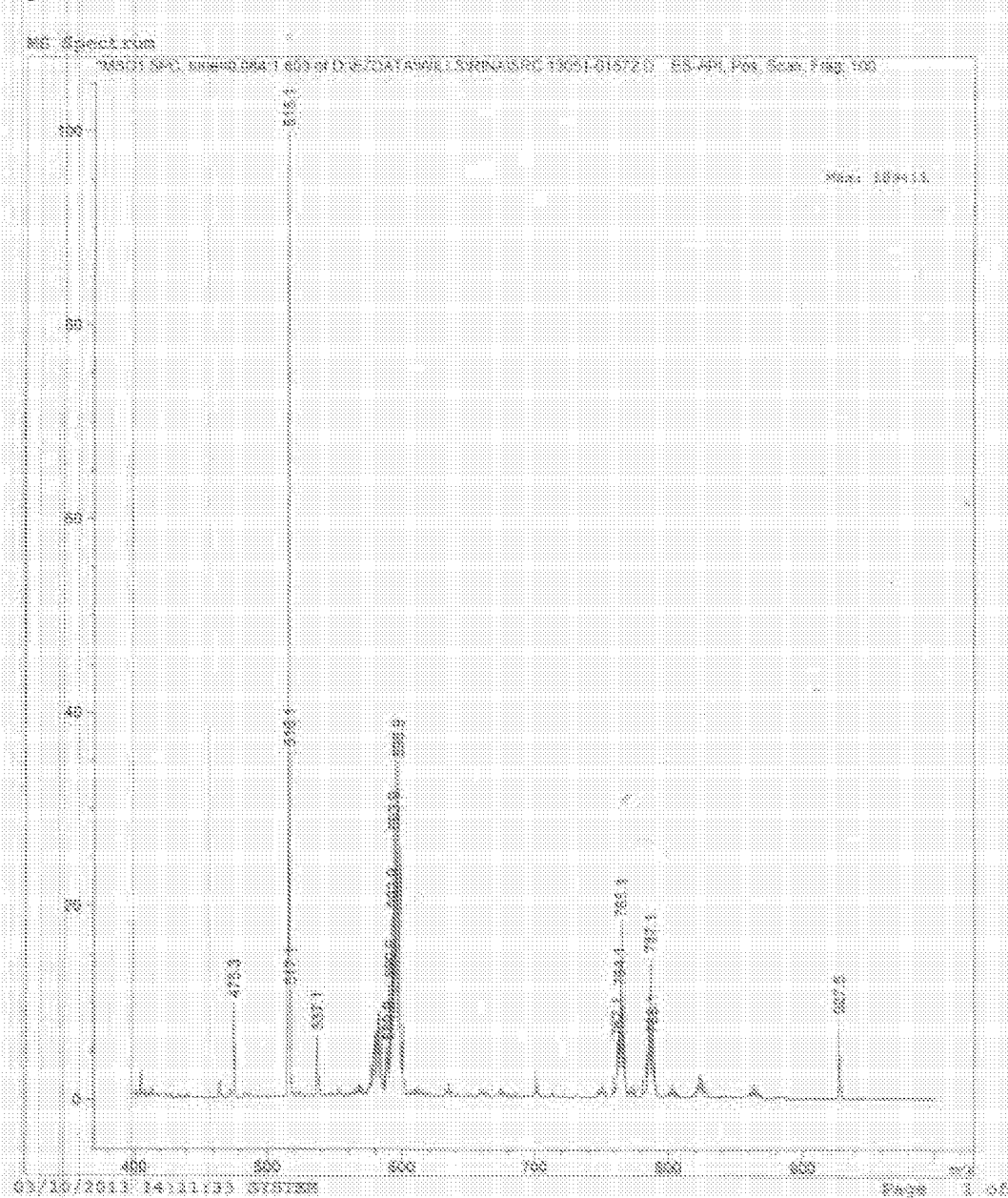

FIG. 7—shows an ESI-MS of a 1st run of the reaction on page 63 under the following conditions: Power=40 W, Temp=50° C., RAMP=2 min, Hold=10 min, Pressure=60 psi.

Figure 8:
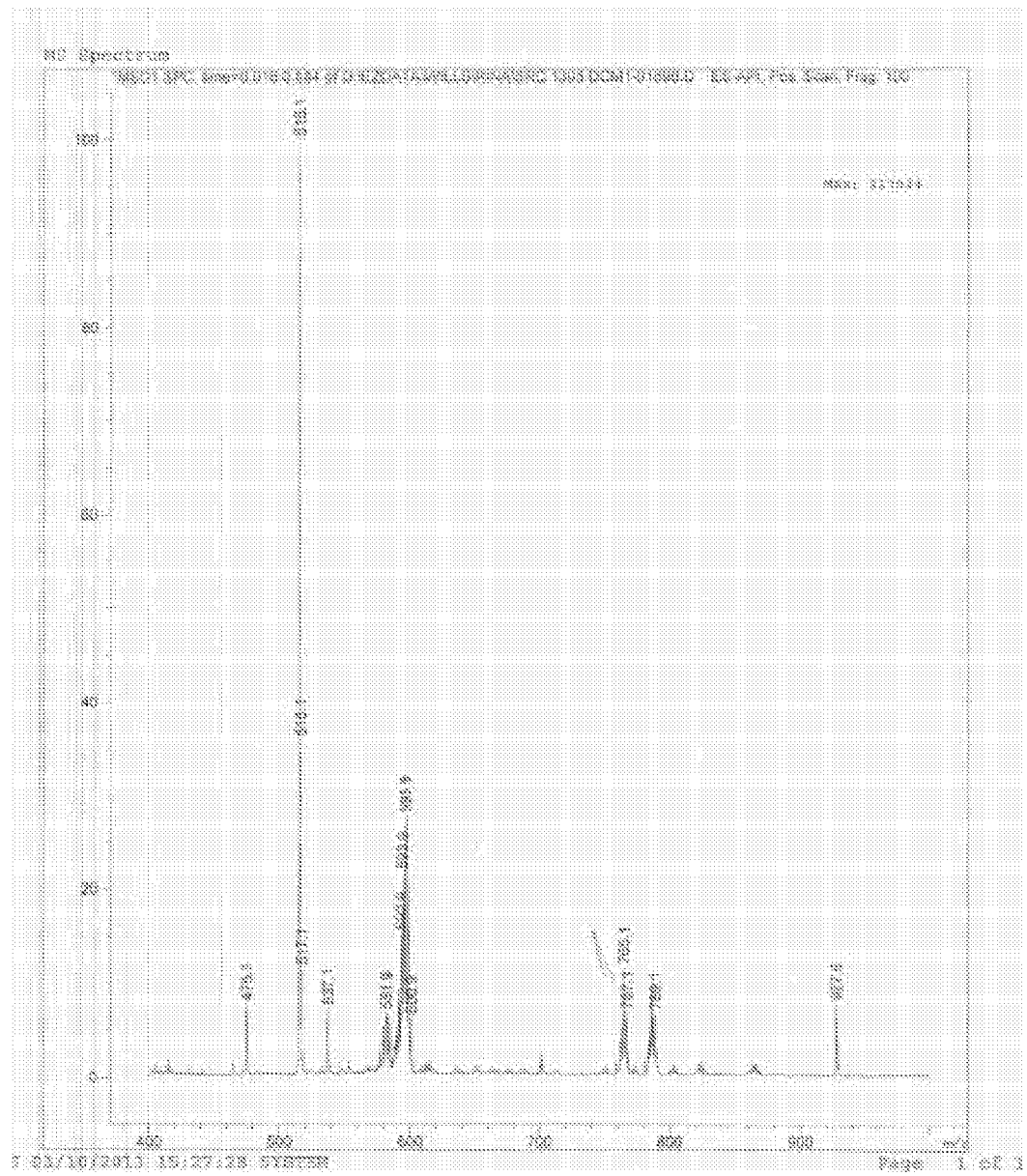

FIG. 8—shows an ESI-MS of a 3rd run of the reaction on page 63 under the following conditions: Power=80 W, Temp=75° C., RAMP=2 min, Hold=10 min, Pressure=100 psi FIG. 9—shows an ESI-MS of a 1st run of the reaction on page 64 under the following conditions: 80 W, Temp=80° C., RAMP=2 min, Hold=10 min, Pressure=60 psi.

Figure 10:
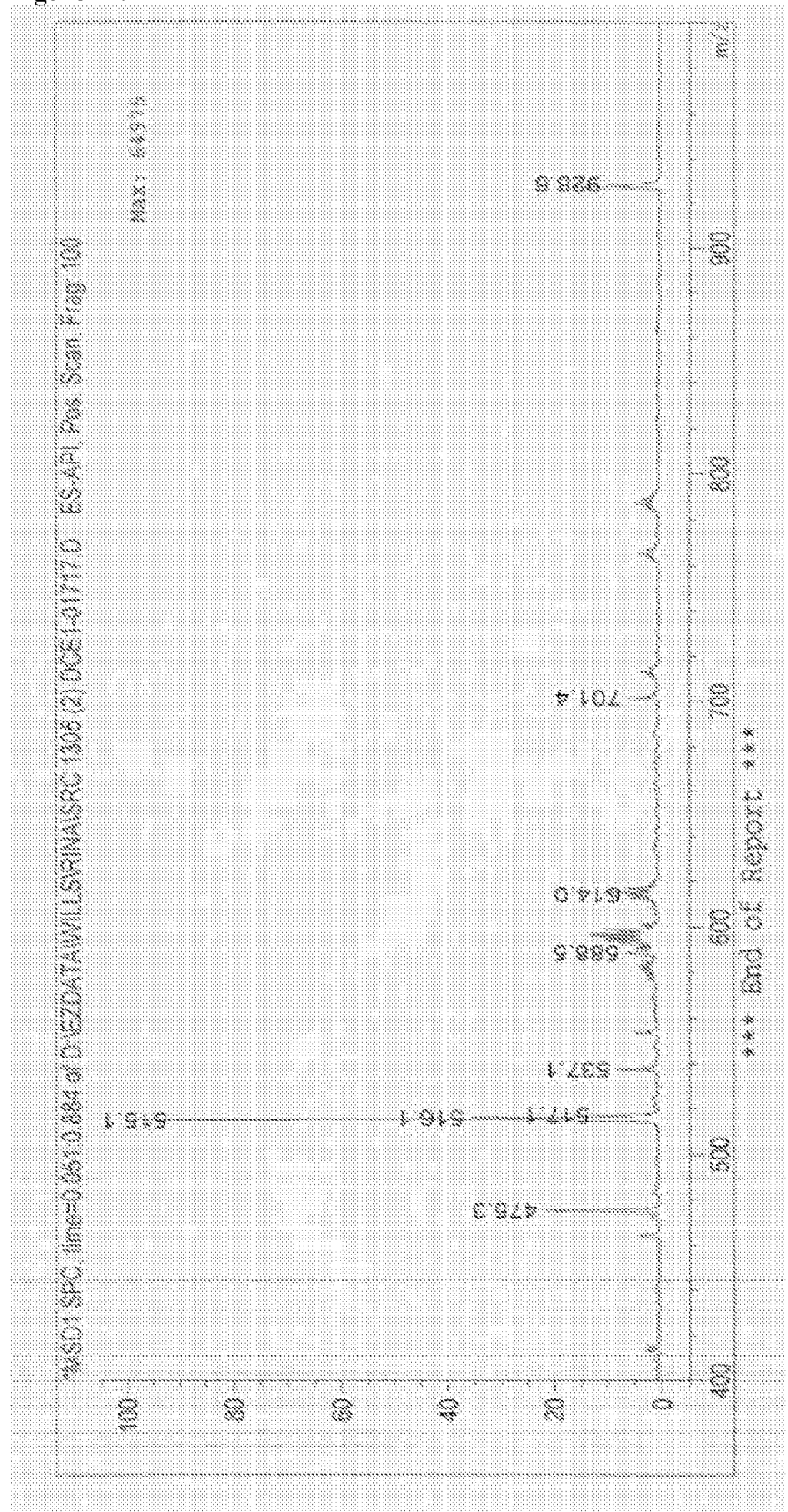

FIG. 10—shows an ESI-MS of a 2nd run of the reaction on page 64 under the following conditions: Power=80 W, Temp=100° C., RAMP=2 min, Hold=10 min, Pressure=60 psi.

Figure 11:
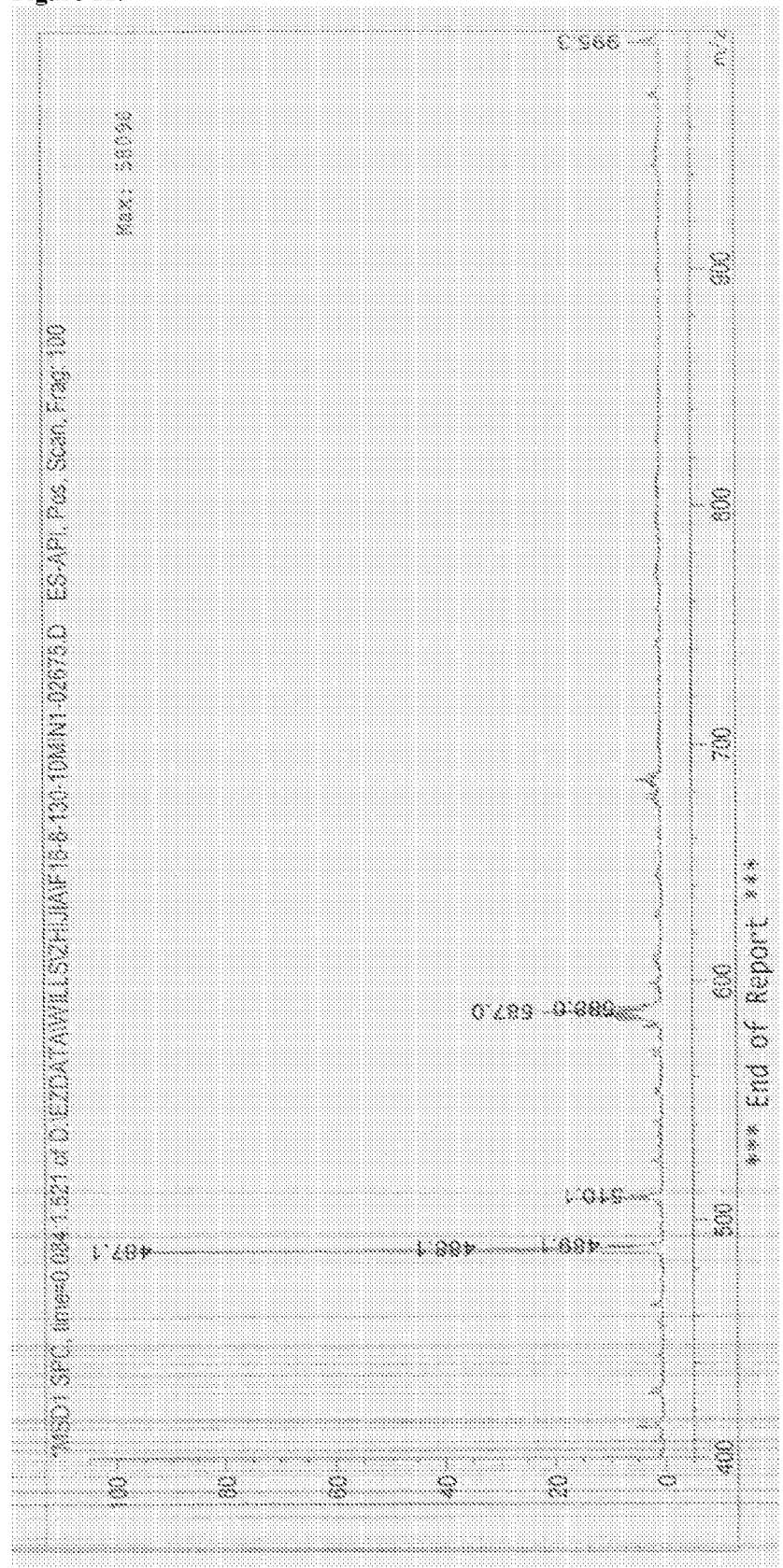

FIG. 11—shows the a ESI-MS of the compound of page 64 formed by MS under 130° C. in MW for 10 min.

Figure 12:
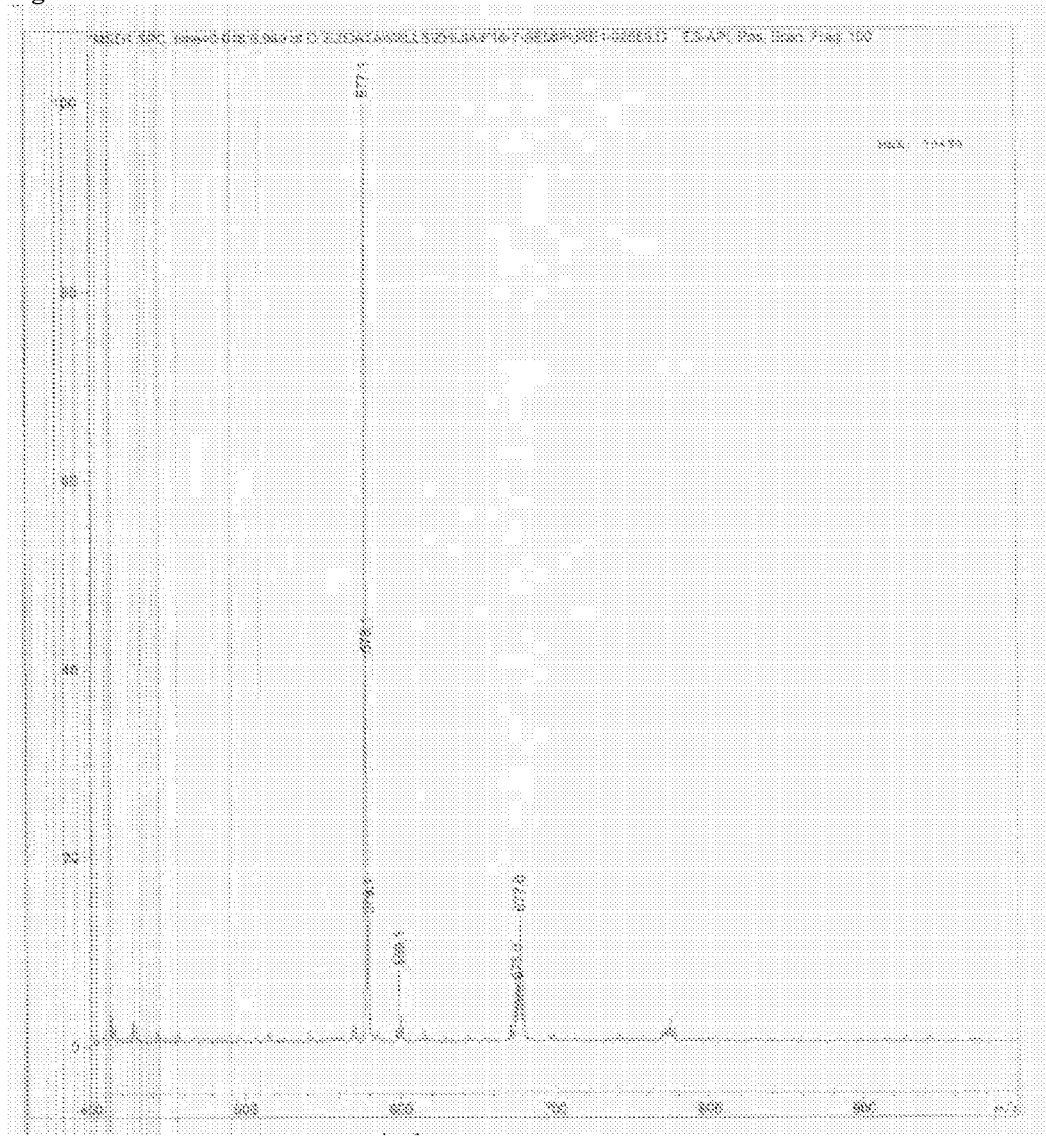

FIG. 12—shows the a ESI-MS of the compound of page 64 formed by MS under 130° C. in MW for 10 min.

Figure 13:
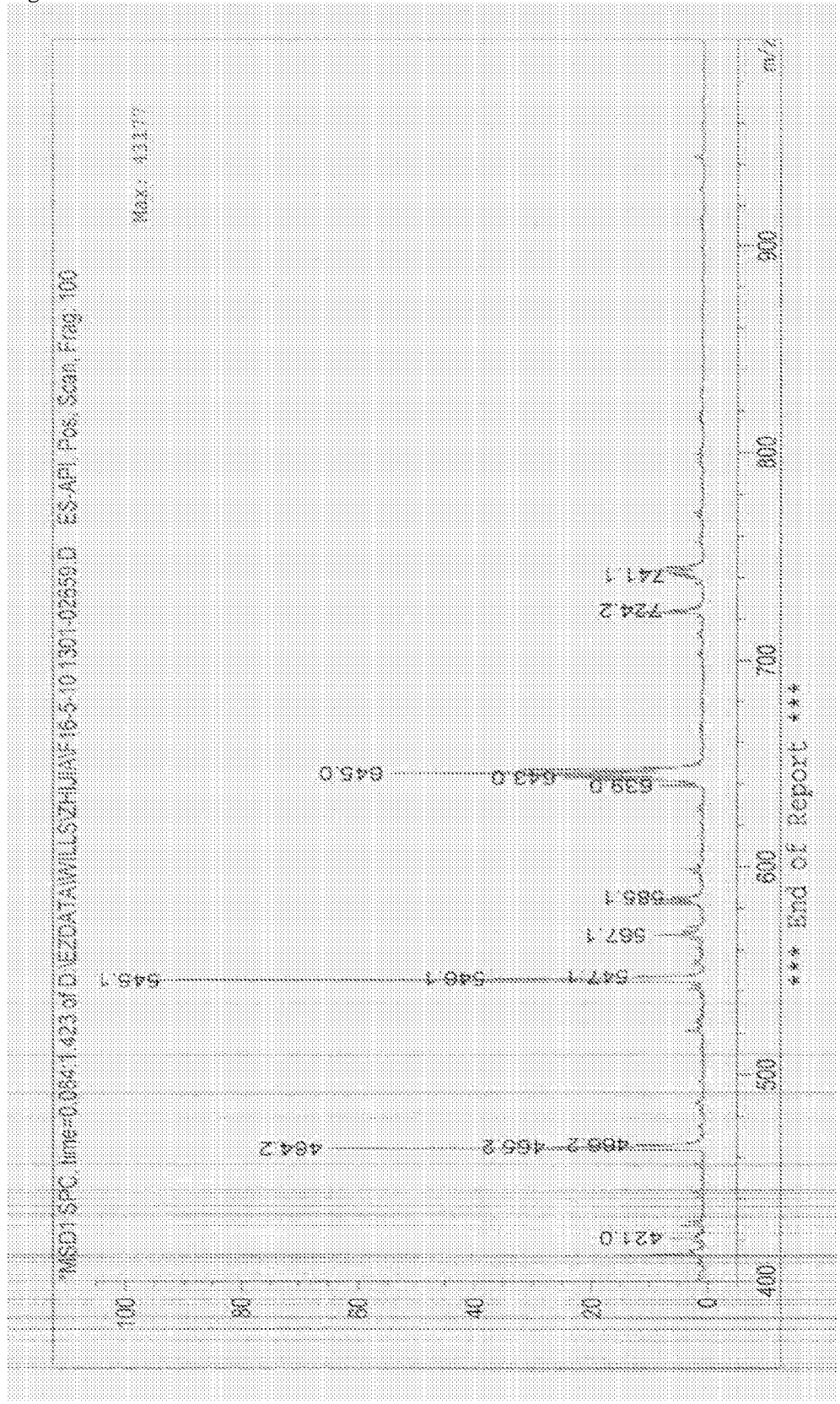

FIG. 13—shows the a ESI-MS of the compound of page 65 formed by MS under 130° C. in MW for 10 min.

Figure 14:
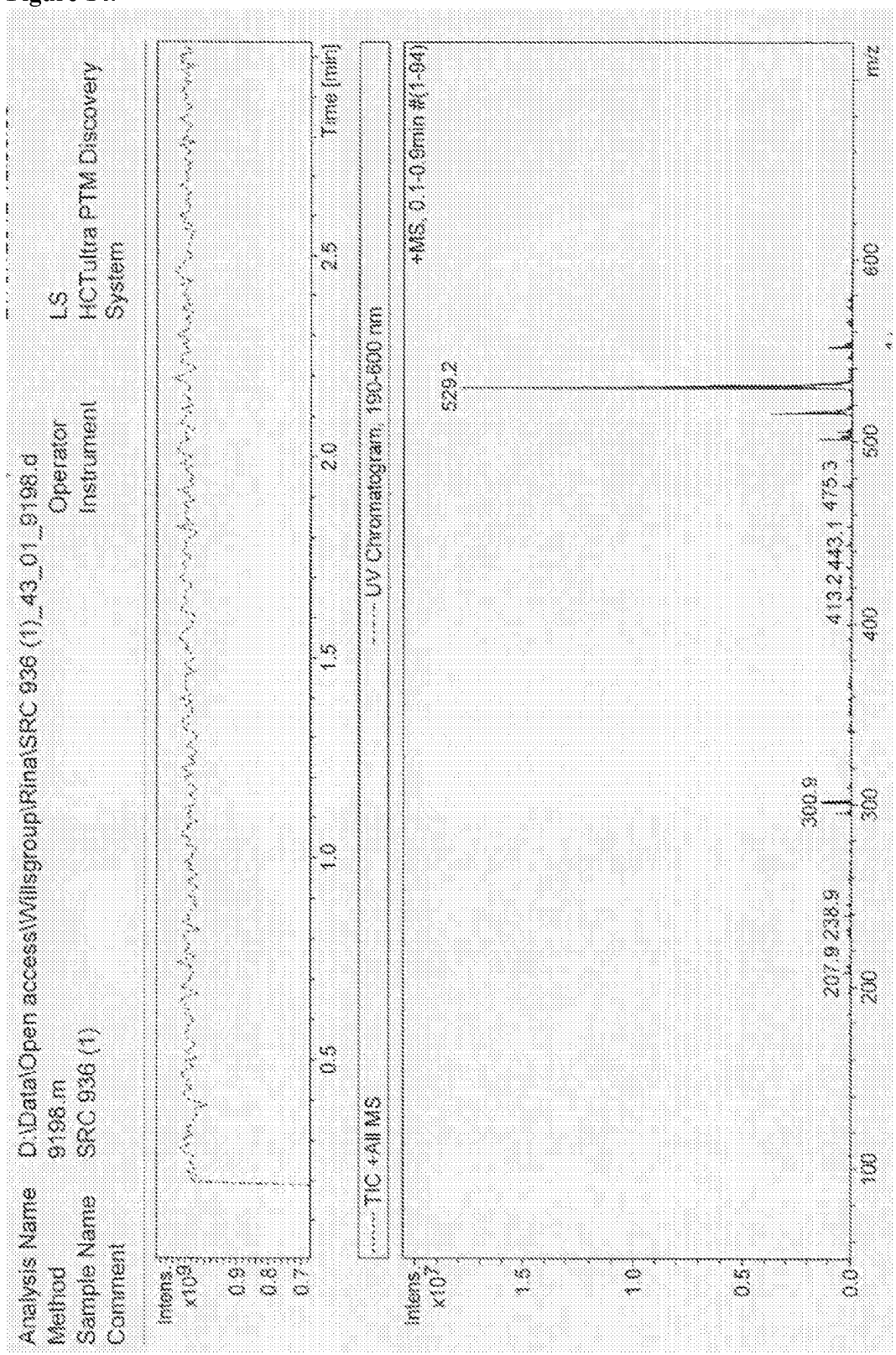

FIG. 14—shows an ESI-MS of the compound complied with aromatised starting described as SRC 936, 26 Jul. 2012 on page 69.

Figure 15:
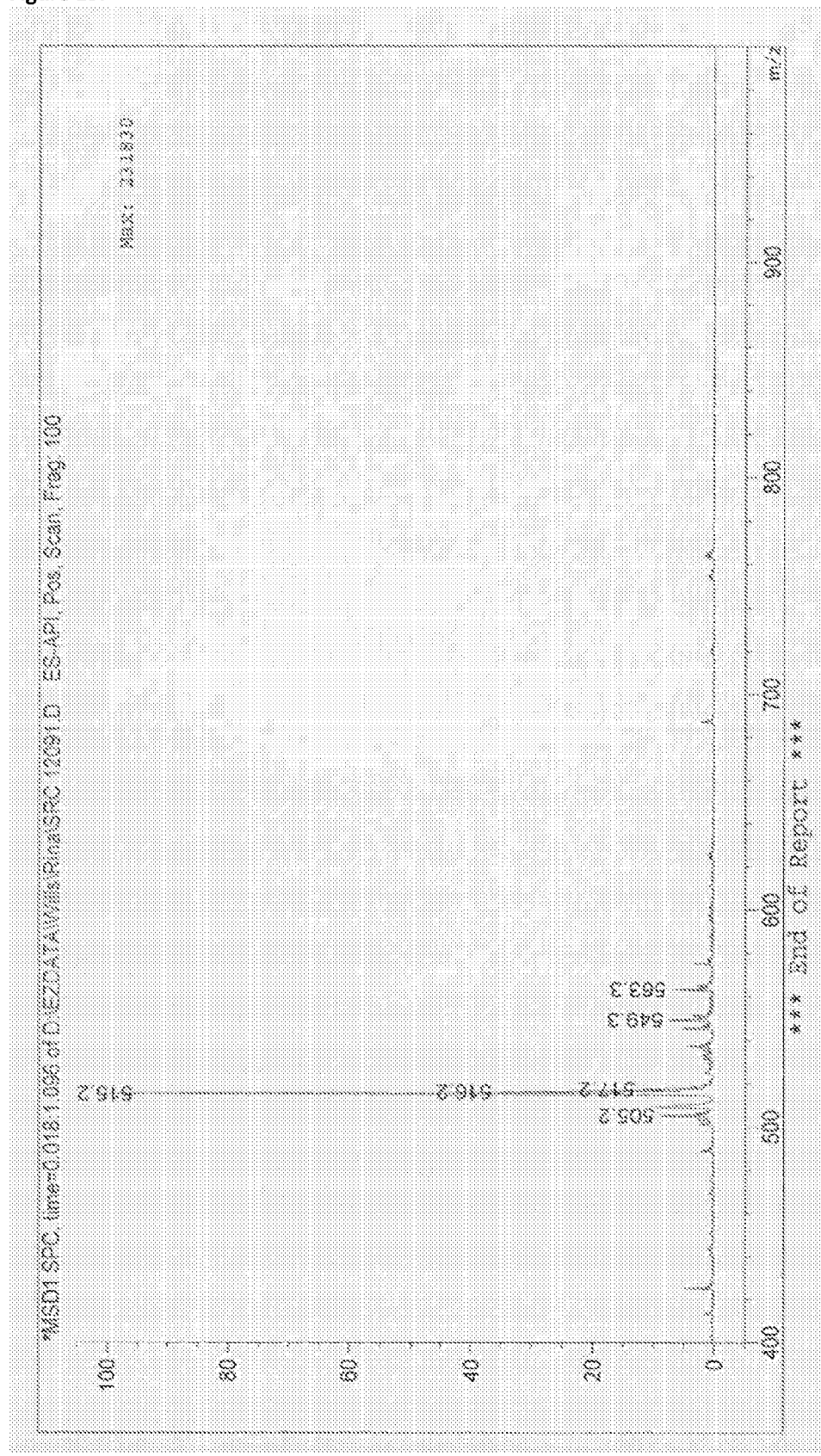

FIG. 15—shows an ESI-MS of the compound complied with aromatised starting described as SRC 1209, 11 Jun. 2013 on page 69.

Figure 16:
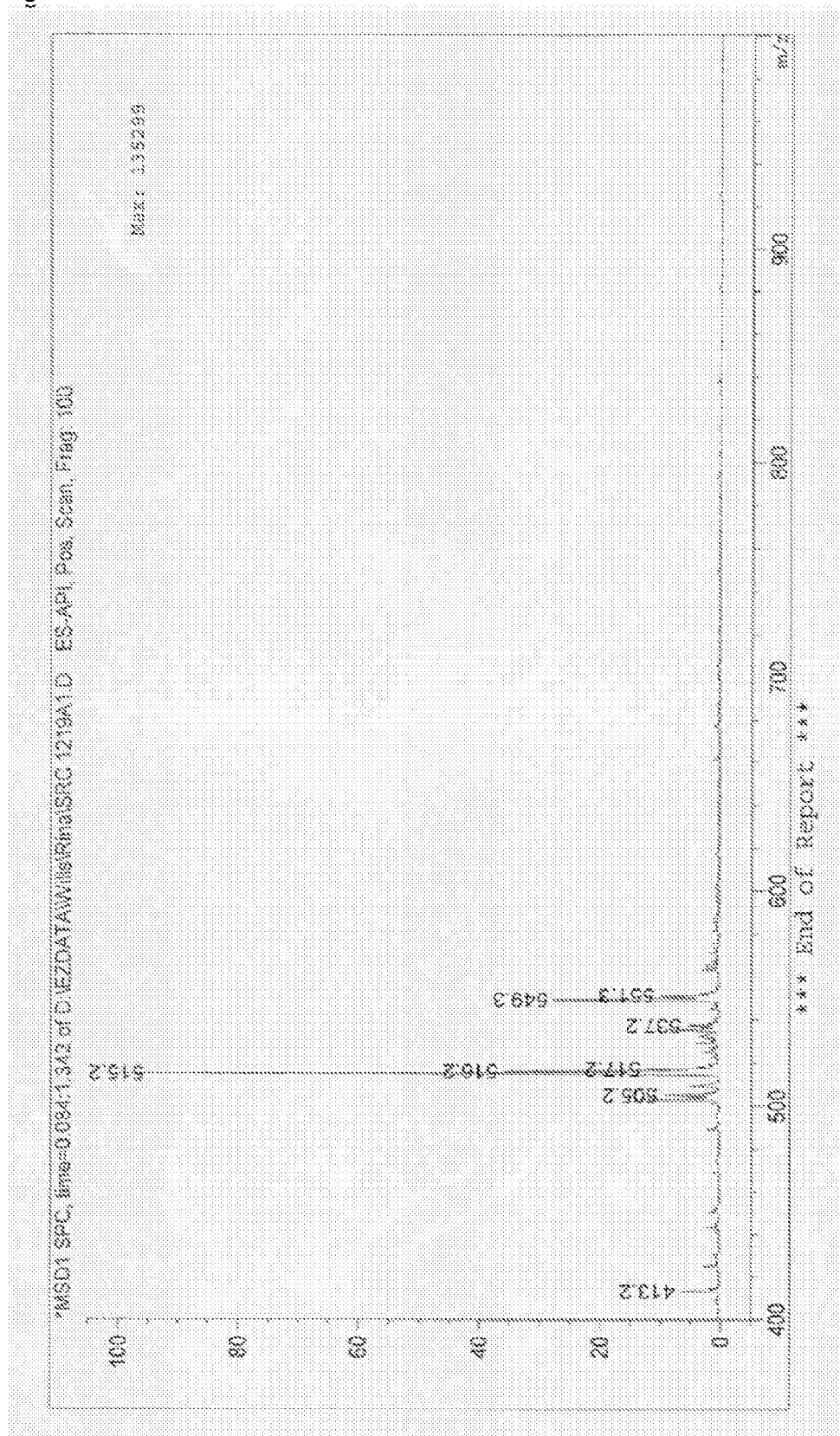

FIG. 16—shows an ESI-MS of the compound complied with aromatised starting described as SRC 1219a, 19 Jun. 2013 on page 69.

Figure 17:
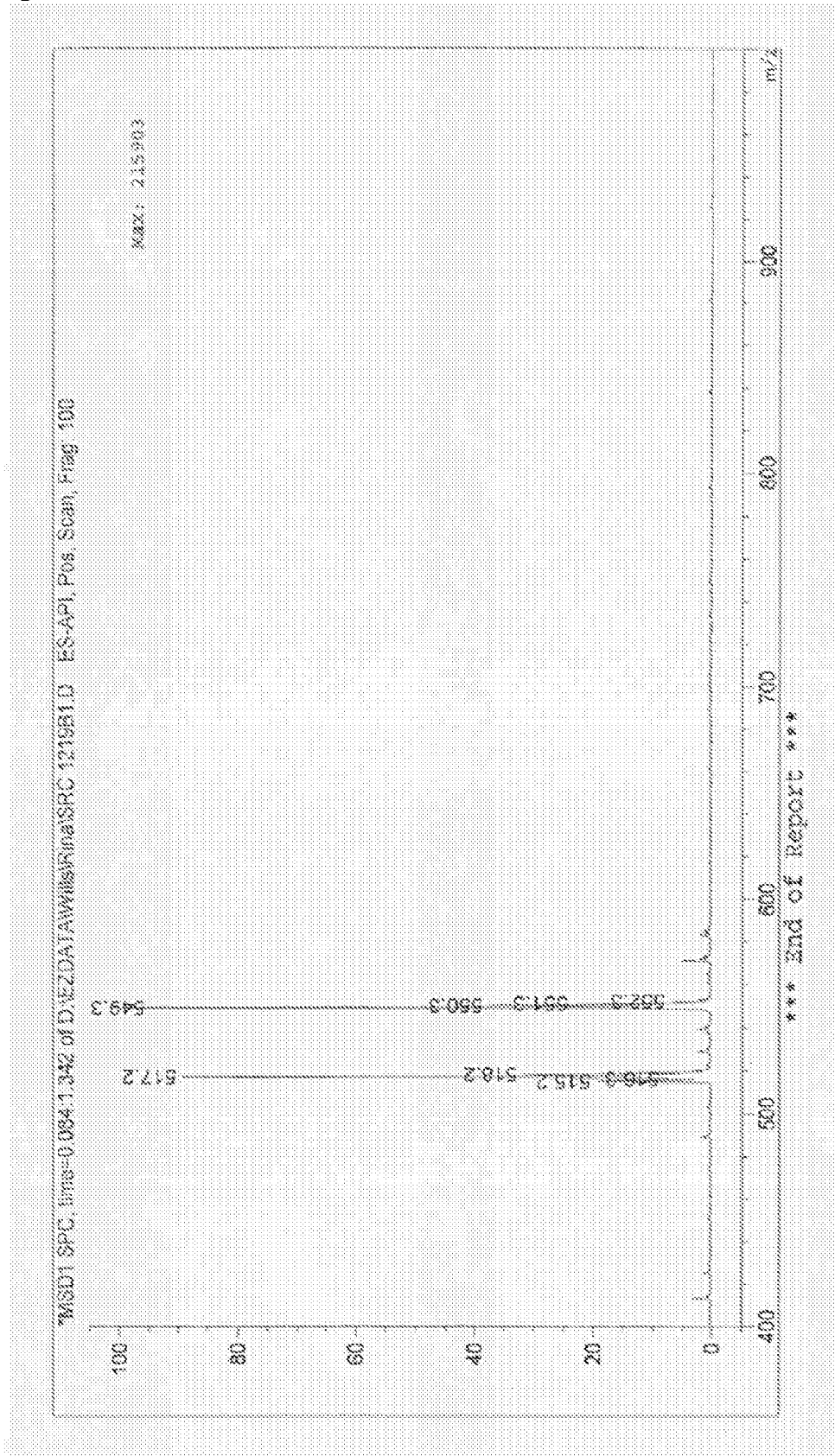

FIG. 17—shows an ESI-MS of the compound complied with aromatised starting described as SRC 1219b, 19 Jun. 2013 on page 70.

Figure 18:
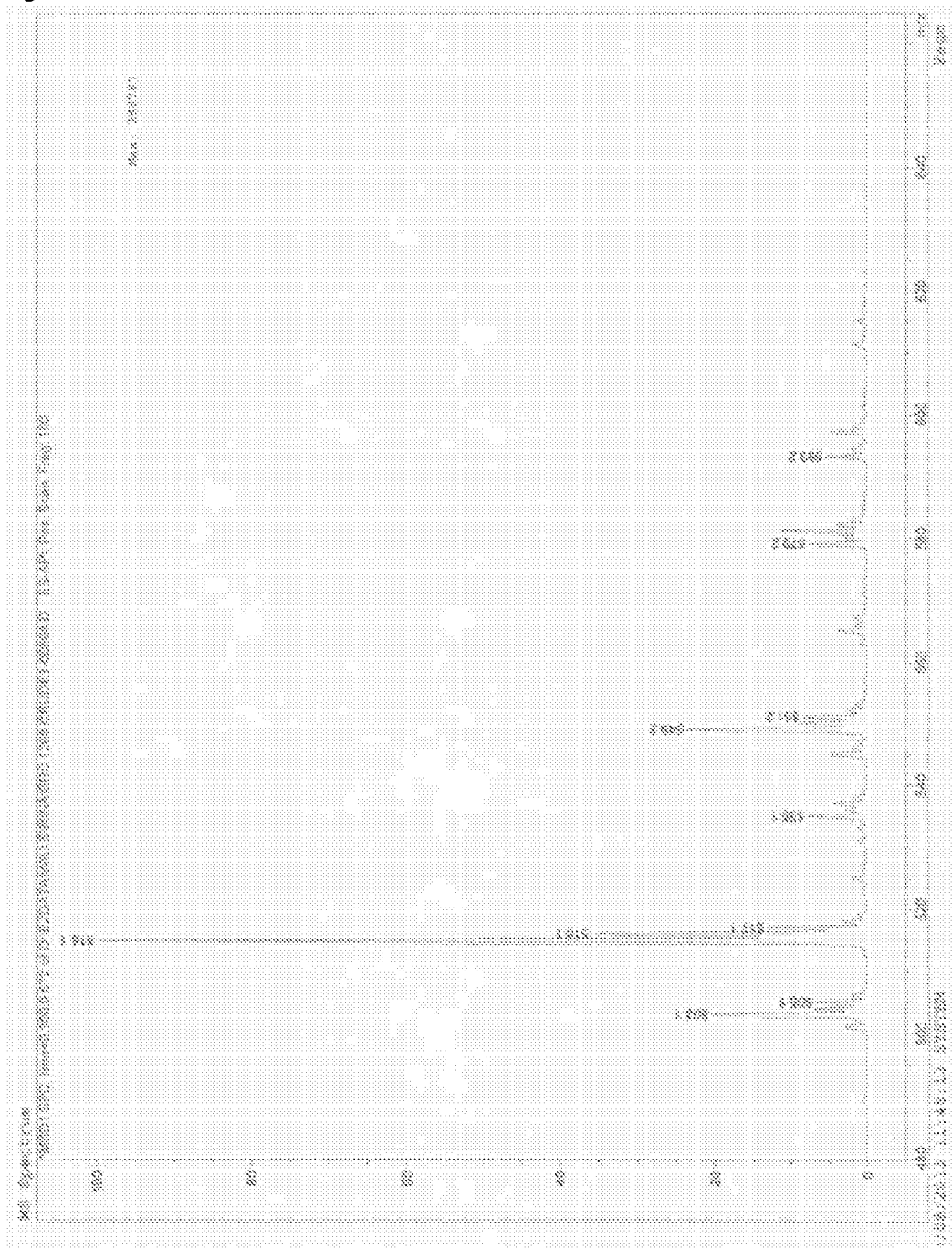

FIG. 18—shows an ESI-MS of the compound complied with aromatised starting described as 1268, 29 Aug. 2013 on page 70.

Figure 19:
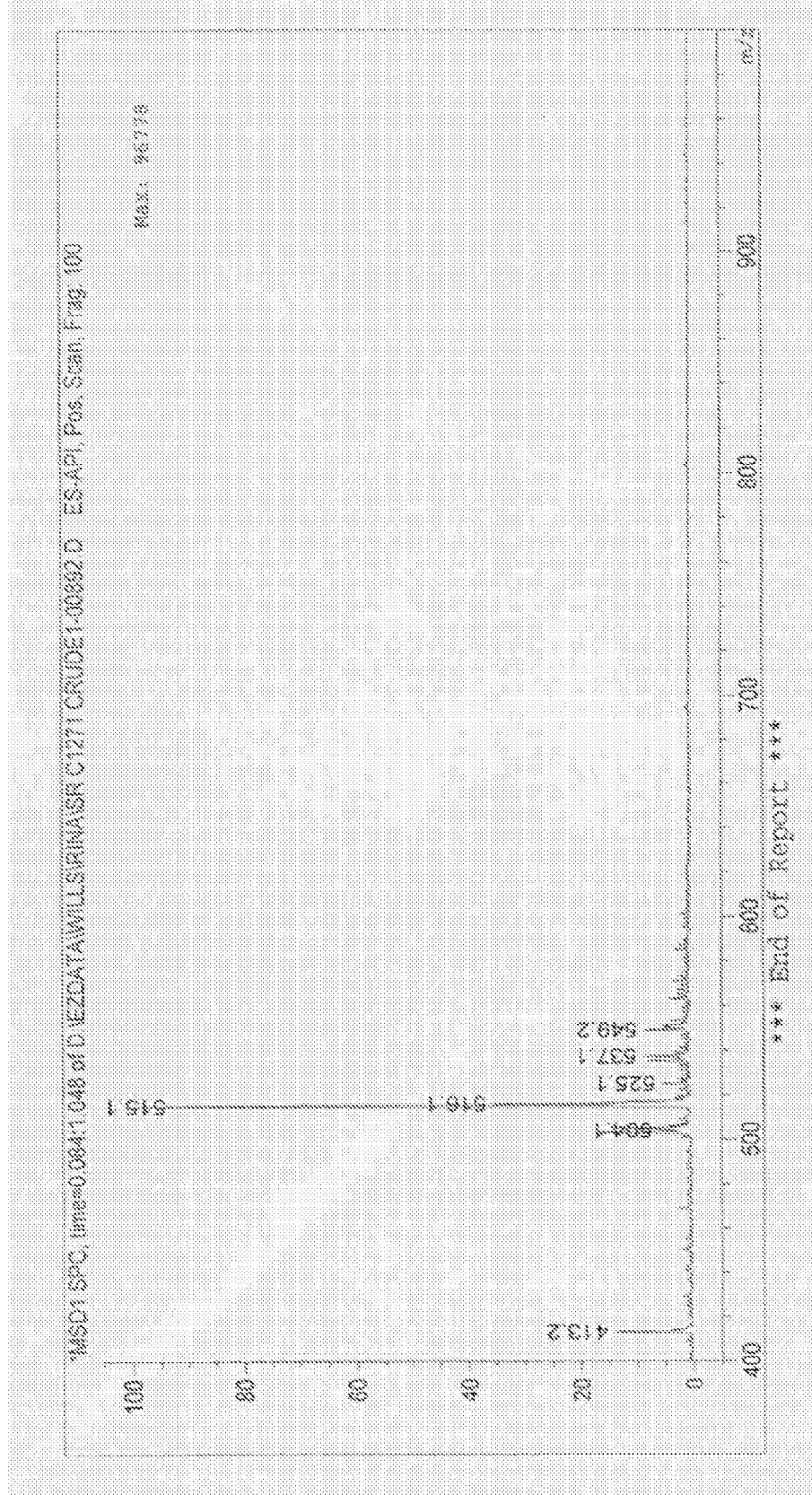

FIG. 19—shows an ESI-MS of the compound complied with aromatised starting described as 1271, 2 Sep. 2013 on page 70.

Figure 20:
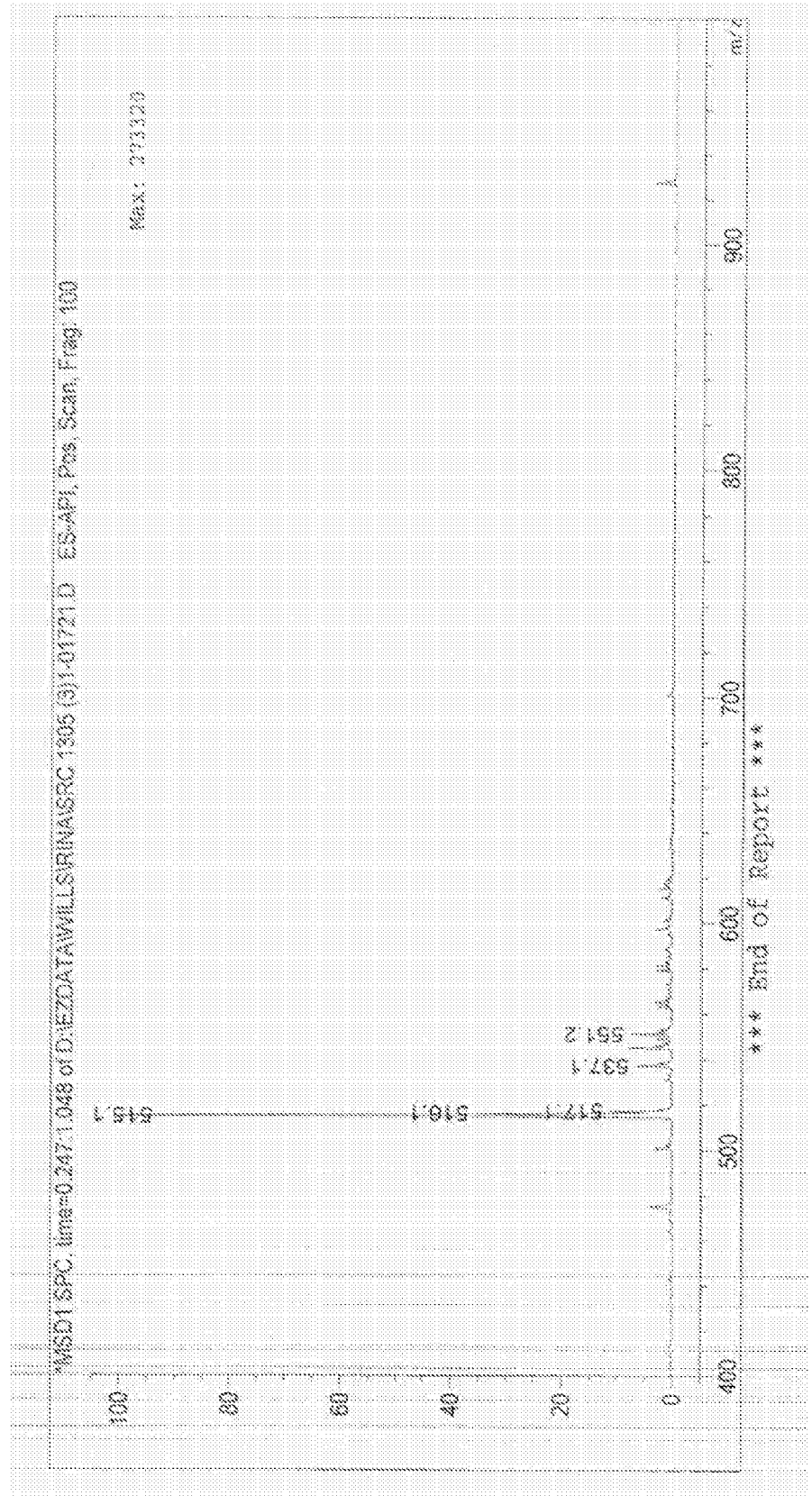

FIG. 20—shows an ESI-MS of the compound complied with aromatised starting described as 1305(3), 3 Oct. 2013 on page 70.

Figure 21:
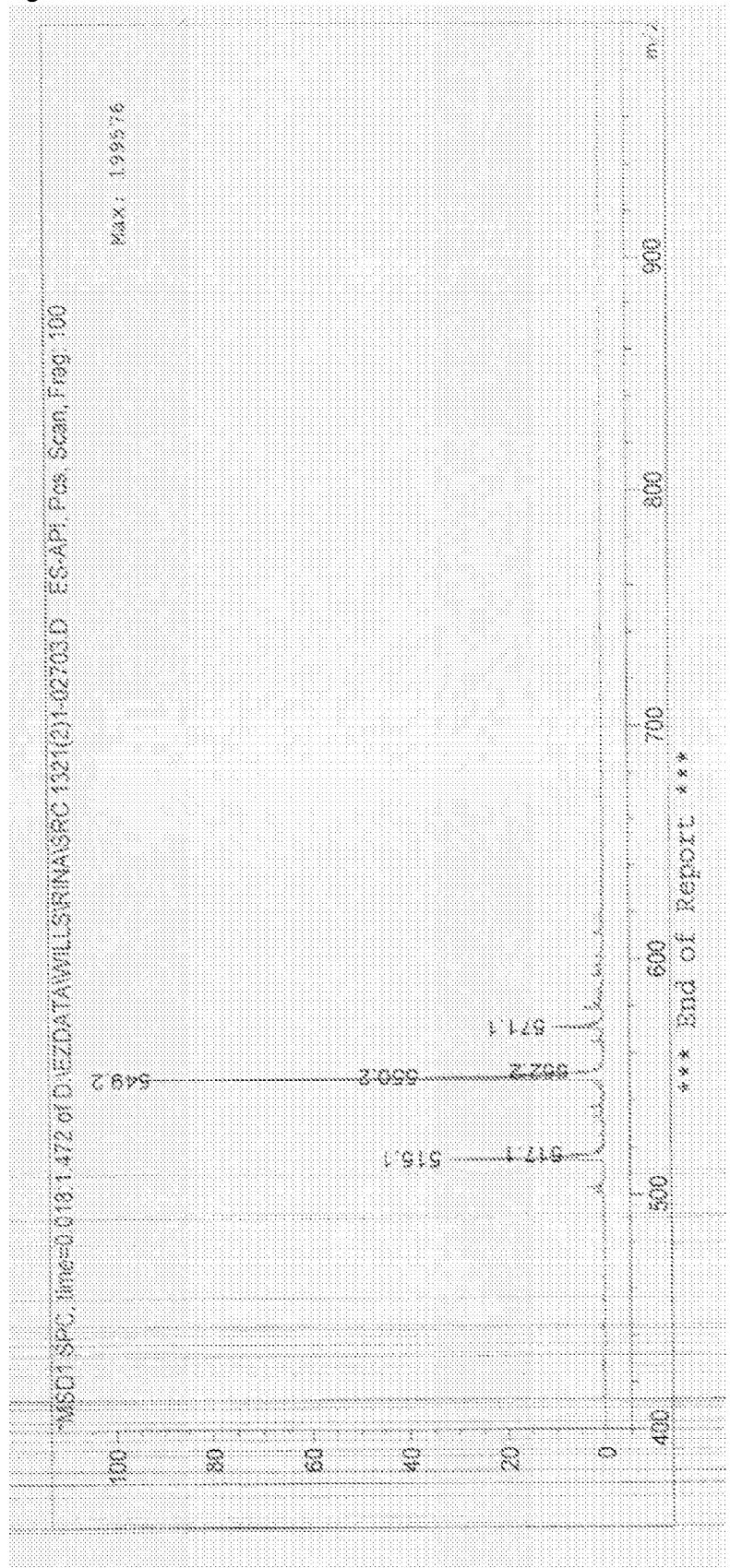

FIG. 21—shows an ESI-MS of the compound complied with aromatised starting described as 1321(2), 29 Oct. 2013 on page 70.

EXAMPLES

Synthesis of η-6 Arene Ruthenium Precursor

Compounds according to general formula (IIa) and (IIb) are well known in the art and were synthesised using known synthetic routes (see references [11]-[11c]). The reaction scheme is represented below:

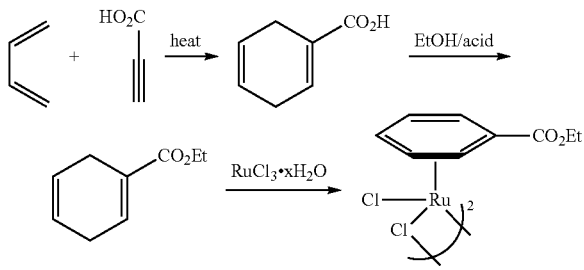

Synthesis of Catalyst

Example 1

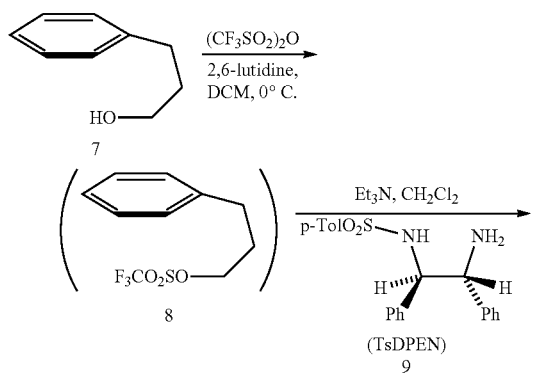

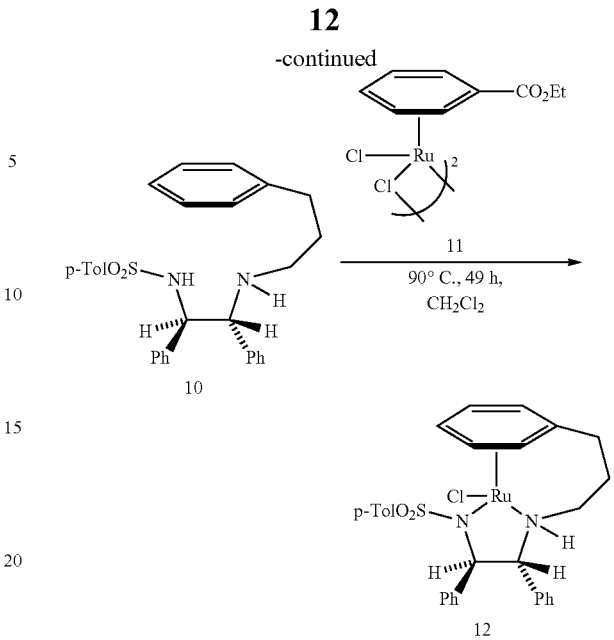

Procedure for the Preparation of 10 from 7.

To a mixture of 3-phenyl-1-propanol (0.149 mL, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) into dry DCM (1.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R) TsDPEN (0.250 g, 0.683 mmol, 1.0 eq) and triethylamine (TEA) (0.228 mL, 1.639 mmol, 2.4 eq) in dry DCM (1.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×10 mL). The organic layer was separated, washed with H$_2$O (2×10 mL), brine (10 mL), dried over anhydrous Na$_2$SO$_4$, filtered and concentrated to give a crude compound. The crude compound was purified by column chromatography over silica gel using EtOAc:Pet. ether (25:75) as an eluent to give a residue. The residue was triturated in n-pentane (to remove traces of 2,6-lutidine) to give a solid. The solid was filtered, washed with n-pentane and dried under vacuum to give pure compound 10 as white solid (0.280 g, 0.579 mmol, 84.7%).

$\delta_H$ (300 MHz, CDCl$_3$) 7.36 (2H, d, J 8.4, —CH of phenyl), 7.28-7.23 (2H, m, —CH of phenyl), 7.19-7.09 (5H, m, —CH of phenyl), 7.07-7.00 (6H, m, —CH of phenyl), 6.95-6.87 (4H, m, —CH of phenyl), 6.25 (1H, br s, —NHTs), 4.25 (1H, d, J 7.8, —CHNHTs), 3.59 (1H, d, J 7.8, —CHNH(CH$_2$)$_3$—), 2.61-2.49 (2H, m, —NH—CH$_2$CH$_2$CH$_2$—), 2.47-2.39 (1H, m, —NH—CHHCH$_2$CH$_2$—), 2.34-2.25 (1H, m, —NH—CHHCH$_2$CH$_2$—), 2.32 (3H, s, —CH$_3$), 1.80-1.62 (2H, m, —NH—CH$_2$CH$_2$CH$_2$—), 1.29 (1H, br s, —NH(CH$_2$)$_3$—).

m/z ESI-MS [M+H]$^+$ 485.1; HRMS found 485.2259 (C$_{30}$H$_{32}$N$_2$O$_2$S H+ requires 485.2257, error=0.1 ppm).

Procedure for the Preparation of 12 from 10.

Compound 10 (C$_{30}$H$_{32}$N$_2$O$_2$S, 0.050 g, 0.103 mmol, 1.0 eq) was added to [RuCl$_2$(C$_9$H$_{10}$O$_2$)]$_2$ 11 (0.033 g, 0.052 mmol, 0.5 eq) in dry DCM (1.5 mL) in a glass tube under N$_2$. The tube was sealed and the mixture was stirred at room temp for 30 min to give a brick red solution and then heated at 90° C. for 49 h. The reaction was followed by TLC and mass spectra analysis. The reaction mixture was cooled to room temperature and concentrated to give a dark brown residue. The residue was precipitated from diethyl ether, filtered and dried to give a dark brown solid. The solid was purified by column chromatography over Florisil using DCM:MeOH (97:3 to 88:12) to give 12 as a brown solid (0.034 g, 0.055 mmol, 53%).

$\delta_H$ (300 MHz, CDCl$_3$) 7.24 (2H, d, J 7.2, —CH of phenyl), 7.11-7.04 (4H, m, —CH of phenyl), 6.86-6.69 (6H, m, —CH of phenyl), 6.61-6.59 (2H, m, —CH of phenyl), 6.23-6.16 (3H, m, —CH of Ru—Ar), 5.22 (1H, s, —CH of Ru—Ar), 5.03 (1H, m, —CH of Ru—Ar), 4.43 (1H, br d, —NH(CH$_2$)$_3$—), 4.03 (1H, d, J 10.8, —CHNTs), 3.65-3.62 (1H, m, —CHNH(CH$_2$)$_3$—), 2.87-2.75 (1H, m, —NH—CHHCH$_2$CH$_2$—), 2.70-2.46 (2H, m, —NH—CHHCH$_2$CHH—), 2.34-2.26 (1H, m, —NH—CH$_2$CH$_2$CHH—), 2.25 (3H, s, —CH$_3$), 2.19-2.10 (2H, m, —NH—CH$_2$CH$_2$CH$_2$—).

m/z ESI-MS [M-Cl]$^+$ 585.1

Example 2

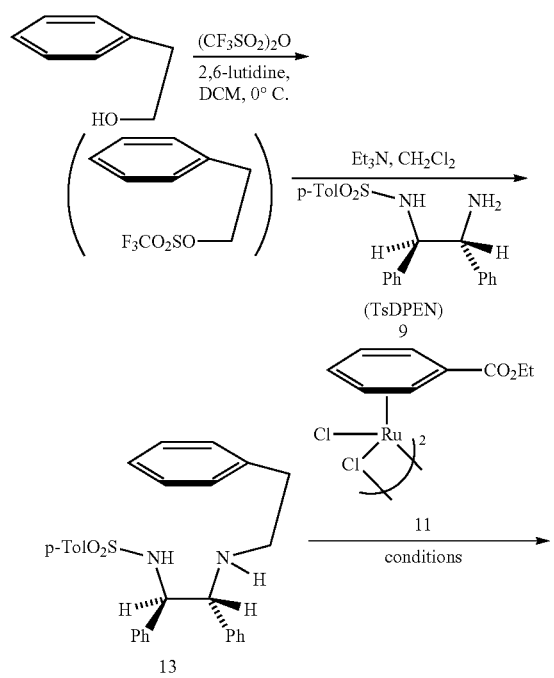

Procedure for the Preparation of 13 from 2-phenylethanol.

To a mixture of 2-phenyl-1-ethanol (0.131 mL, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) in dry DCM (1.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R) TsDPEN 9 (0.250 g, 0.683 mmol, 1.0 eq) and TEA (0.228 mL, 1.639 mmol, 2.4 eq) in dry DCM (1.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×10 mL). The organic layer was separated, washed with H$_2$O (2×10 mL), brine (10 mL), dried over anhydrous Na$_2$SO$_4$, filtered and concentrated to give crude compound. The crude compound was purified by column chromatography over silica gel using EtOAc:Pet. ether (25:75) as an eluent to give a residue. The residue was triturated in n-pentane (to remove traces of 2,6-lutidine) to give a solid. The solid was filtered, washed with n-pentane and dried under vacuum to give pure compound 13 as white solid (0.275 g, 0.585 mmol, 85.7%).

$\delta_H$ (300 MHz, CDCl$_3$) 7.34 (2H, d, J 8.4, o-CH of —SO$_2$C$_6$H$_4$CH$_3$), 7.28-7.16 (3H, m, —CH of phenyl), 7.12-6.97 (10H, m, —CH of phenyl), 6.90-6.86 (2H, m, —CH of phenyl), 6.80-6.77 (2H, m, —CH of phenyl), 6.24 (1H, br s, —NHTs), 4.16 (1H, d, J 7.8, —CHNHTs), 3.60 (1H, d, J 7.8, —CHNH(CH$_2$)$_2$—), 2.78-2.50 (4H, m, —NH—CH$_2$CH$_2$—), 2.33 (3H, s, —CH$_3$), 1.32 (1H, br s, —NH(CH$_2$)$_3$—).

m/z ESI-MS [M+H]$^+$ 471.6; HRMS found 471.2101 (C$_{29}$H$_{30}$N$_2$O$_2$S H+ requires 471.2101, error=0.4 ppm).

Procedure for the Preparation of 14 from 13.

Compound 13 (C$_{29}$H$_{30}$N$_2$O$_2$S, 0.050 g, 0.103 mmol, 1.0 eq) and [RuCl$_2$(C$_9$H$_{10}$O$_2$)]$_2$ 11 (0.033 g, 0.052 mmol, 0.5 eq) into dry DCM (1.5 mL) in a glass tube under N$_2$. The tube was sealed and mixture was stirred at room temp for 30 min to give brick red solution and heated at 90° C. for 49 h. The reaction was followed by TLC and mass spectra analysis. The reaction mixture was cooled to room temperature and concentrated to give dark brown residue. The residue was scratched in diethyl ether, filtered and dried to give dark brown solid. The solid was purified by column chromatography over Florisil using DCM:MeOH (97:3 to 88:12) to give 14 as a brown solid (0.034 g, 0.055 mmol, 53%). Characterised by ESI-MS very low conv. The product was difficult to fully purify due to the formation of a number of impurities.

m/z ESI-MS [M-Cl]$^+$ 571.0

Example 3

Preparation of '4-methoxy' or 'p-OMe' Catalyst

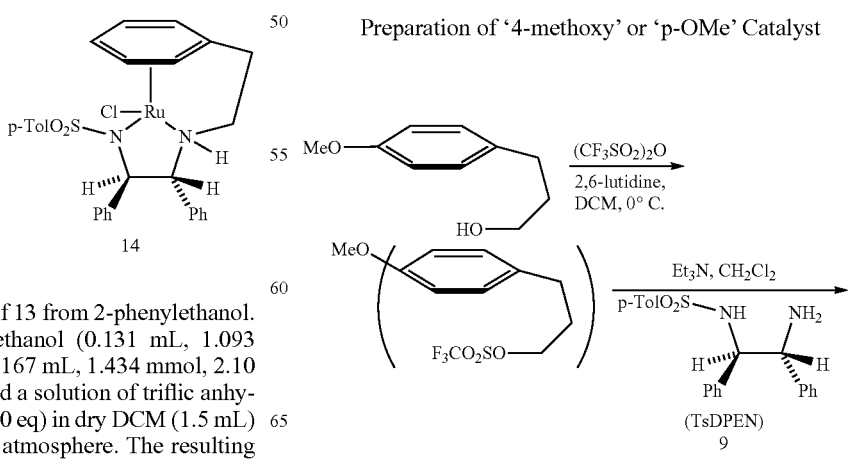

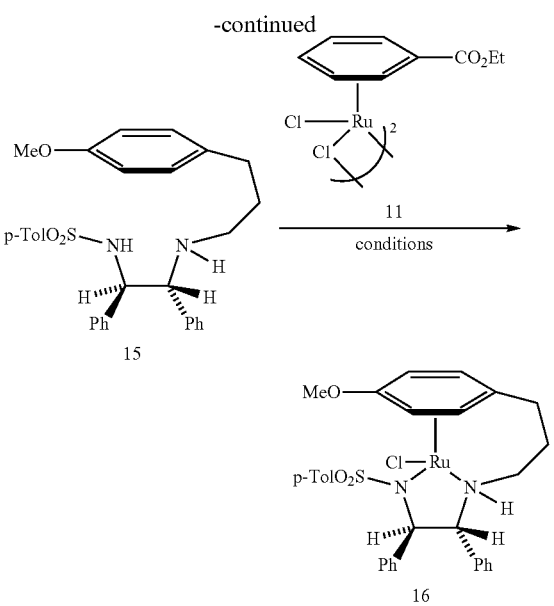

Procedure for the Preparation of 15 from 3-(4-methoxyphenyl)-1-propanol.

To a mixture of 3-(4-methoxyphenyl)-1-propanol (0.362 g, 2.186 mmol, 1.6 eq) and 2,6-lutidine (0.334 mL, 2.869 mmol, 2.10 eq) in dry DCM (10 mL) was added a solution of triflic anhydride (0.390 mL, 2.322 mmol, 1.70 eq) in dry DCM (2.5 mL) dropwise at 0° C. under an inert atmosphere. The resulting light pink solution was stirred at 0° C. for 30 min and at room temperature for 60 min. The mixture was again cooled down to 0° C. To this, a solution of (1R,2R)TsDPEN (0.500 g, 1.366 mmol, 1.0 eq) and TEA (0.456 mL, 3.278 mmol, 2.4 eq) in dry DCM (2.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×25 mL). The organic layer was separated, washed with H$_2$O (2×15 mL), brine (25 mL), dried over anhydrous Na$_2$SO$_4$, filtered and concentrated to give crude compound. The crude compound was purified by column chromatography over silica gel using EtOAc:Pet. ether (25:75) as an eluent to give a residue. The residue was triturated in n-pentane (to remove traces of 2,6-lutidine) to give a solid. The solid was filtered, washed with n-pentane and dried under vacuum to give pure compound 15 as white solid (0.625 g, 1.216 mmol, 89%).

$\delta_H$ (300 MHz, CDCl$_3$) 7.36 (2H, d, J 8.1, —CH of phenyl), 7.14-7.11 (3H, m, —CH of phenyl), 7.07-6.98 (7H, m, —CH of phenyl), 6.94-6.87 (4H, m, —CH of phenyl), 6.80 (2H, d, J 8.7, —CH of phenyl), 6.27 (1H, br s, —NHTs), 4.24 (1H, d, J 8.0, —CHNHTs), 3.78 (3H, S, —OCH$_3$), 3.58 (1H, d, J 7.8, —CHNH(CH$_2$)$_3$—), 2.55-2.37 (3H, m, —NH—CHHCH$_2$CH$_2$—), 2.32 (3H, s, —CH$_3$), 2.29-2.23 (1H, m, —NH—CHHCH$_2$CH$_2$—), 1.74-1.60 (2H, m, —NH—CH$_2$CH$_2$CH$_2$—), 1.32 (1H, br s, —NH(CH$_2$)$_3$—).

m/z ESI-MS [M+H]$^+$ 515.1; HRMS found 515.2377 (C$_{31}$H$_{34}$N$_2$O$_3$S H+ requires 515.2363, error=−2.7 ppm).

Procedure for the Preparation of 16 from 15.

Compound 15 (C$_{31}$H$_{34}$N$_2$O$_3$S, 0.200 g, 0.389 mmol, 1.0 eq) and [RuCl$_2$(C$_9$H$_{10}$O$_2$)]$_2$ 11 (0.125 g, 0.195 mmol, 0.5 eq) dissolved in dry DCM (5 mL) in a glass tube under N$_2$. The tube was sealed and mixture was stirred at room temp for 30 min to a give brick red solution and heated at 90° C. for 54 h. The reaction was followed by TLC and mass spectra analysis. The reaction mixture was cooled to room temperature and concentrated to give a dark brown residue. The residue was precipitated from diethyl ether, filtered and dried to give a dark brown solid. The solid was purified by column chromatography over Florisil using DCM:MeOH (97:3 to 90:10) to give brown solid. The solid was recrystallized from MeOH to give 16 as a golden orange solid (0.108 g, 0.166 mmol, 42.7%).

$\delta_H$ (300 MHz, CDCl$_3$) 7.27 (2H, d, J 8.1, —CH of phenyl), 7.18-7.07 (3H, m, —CH of phenyl), 6.84-6.77 (2H, m, —CH of phenyl), 6.73 (2H, d, J 8.1, m-CH of —SO$_2$C$_6$H$_4$CH$_3$), 6.63-6.58 (3H, m, —CH of phenyl), 6.54 (2H, d, J 7.2, —CH of phenyl), 5.55 (1H, dd, J 6.0, 1.2, —CH of Ru—Ar), 5.47 (1H, d, J 6.0, —CH of Ru—Ar), 5.34 (1H, dd, J 6.0, 1.2, —CH of Ru—Ar), 5.27 (1H, dd, J 6.0, —CH of Ru—Ar), 4.32 (1H, d, J 11.1, —CHNTs), 4.05 (1H, br d, —NH(CH$_2$)$_3$—), 3.98 (3H, s, —OCH$_3$), 3.61-3.53 (1H, m, —CHNH(CH$_2$)$_3$—), 2.81-2.73 (1H, m, —NH—CHHCH$_2$CH$_2$—), 2.53-2.25 (3H, m, —NH—CHHCH$_2$CH$_2$—), 2.20 (3H, s, —CH$_3$), 2.12-1.98 (2H, m, —NH—CH$_2$CH$_2$CH$_2$—).

m/z ESI-MS [M-Cl]$^+$ 615.1; HRMS found 615.1258 (C$_{31}$H$_{33}$N$_2$O$_3$RuS—Cl+ requires 615.1257, error=−0.2 ppm).

Alternative Procedures for the Preparation of 16 from 15

Reaction of 15 with 11 in DCM at room temperature for 30 minutes followed by reaction in chlorobenzene (13 mL per 100 mg 15) at 140° C. for 2 h, provided complex 15 (0.105 g 0.164 mmol, 41.5%).

Example 4

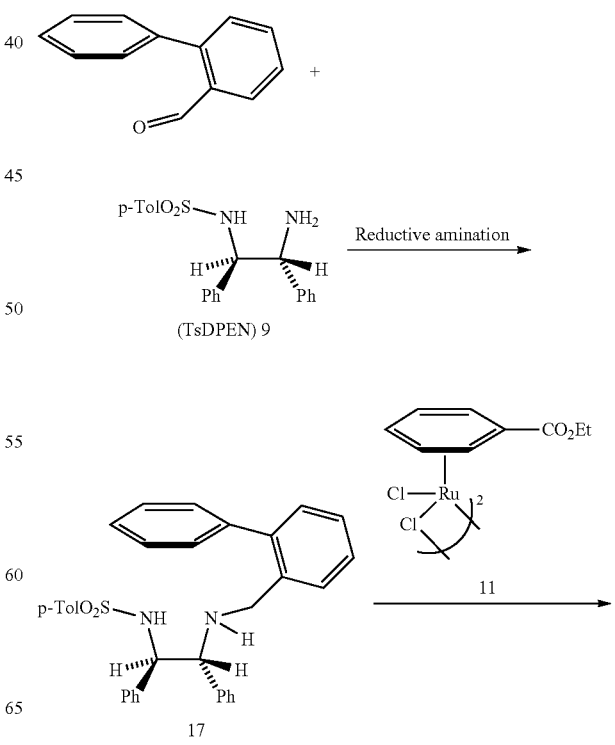

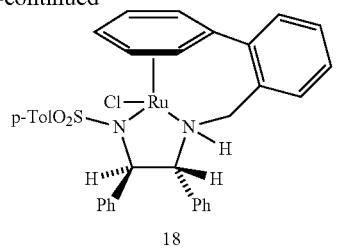

18

Procedure for the Preparation of 17 from biphenyl-2-carboxaldehyde and 9.

To a mixture of (1R,2R)-TsDPEN 9 (0.200 g, 0.546 mmol, 1.0 eq) and MS 4A (0.4 g) in dry methanol (10 mL) was added biphenyl-2-carboxaldehyde (0.101 mL, 0.628 mmol, 1.15 eq) followed by acetic acid (2-3 drops). The mixture was stirred at room temperature under an inert atmosphere for 4.5 h to form the imine To this, NaBH$_3$CN (0.142 g, 2.266 mmol, 4.15 eq) was added and resulting mixture was stirred at room temperature for 18 h. The reaction mixture was filtered and concentrated to give a residue. This was dissolved in DCM (20 mL) and washed with 1M NaOH (2×15 mL), dried over anhydrous Na$_2$SO$_4$, filtered and evaporated on a rotavapor to give the crude product. The crude compound was purified by flash column chromatography over silica gel using EtOAc:Pet. ether (7:3) to give compound 17 as white solid (0.195 g, 0.367 mmol, 67%).

δ$_H$ (400 MHz, CDCl$_3$) 7.33-7.27 (7H, m, —CH of phenyl), 7.21-7.17 (2H, m, —CH of phenyl), 7.12-7.09 (4H, m, —CH of phenyl), 7.05-7.01 (4H, m, —CH of phenyl), 6.96 (2H, d, J 8.4, —CH of phenyl), 6.88-6.86 (2H, m, —CH of phenyl), 6.75-6.73 (2H, m, —CH of phenyl), 6.28 (1H, br d, J 3.4, —NHTs), 4.17 (1H, dd, J 6.6, 3.4, —CHNHTs), 3.52 (1H, d, J 12.6, —CHNHCHH—), 3.51 (1H, d, J 6.6, —CHNHCH$_2$—), 3.29 (1H, d, J 12.6, —CHNHCHH—), 2.31 (3H, s, —CH$_3$), 1.39 (1H, br s, —NH—CH$_2$—).

m/z ESI-MS [M+H]$^+$ 533.2; HRMS found 533.2262 (C$_{34}$H$_{32}$N$_2$O$_2$S H+ requires 533.2257, error=−0.3 ppm).

Procedure for the Preparation of 18 from 17.

Compound 17 (C$_{34}$H$_{32}$N$_2$O$_2$S, 0.050 g, 0.094 mmol, 1.0 eq) and [RuCl$_2$(C$_9$H$_{10}$O$_2$)]$_2$ 11 (0.030 g, 0.047 mmol, 0.5 eq) in dry DCM (1.5 mL) was placed in a glass tube under N$_2$. The tube was sealed and mixture was stirred at room temp for 30 min to give a brick red solution and heated at 90° C. for 49 h. The reaction was followed by TLC and mass spectra analysis. The reaction mixture was cooled to room temperature and concentrated to give dark brown residue. The residue was precipitated from diethyl ether, filtered and dried to give dark brown solid. The solid was purified by column chromatography over Florisil using DCM:MeOH (97:3 to 85:15) to give 18 as a brown solid (0.030 g, 0.045 mmol, 47.8%).

δ$_H$ (300 MHz, CDCl$_3$) 7.61-7.53 (2H, m, —CH of phenyl), 7.42-7.37 (1H, m, —CH of phenyl), 7.21 (2H, d, J 8.1, m-CH of —SO$_2$C$_6$H$_4$CH$_3$), 7.16-7.10 (3H, m, —CH of phenyl), 6.91 (1H, d, J 7.5, —CH of phenyl), 6.79 (2H, d, J 8.1, o-CH of —SO$_2$C$_6$H$_4$CH$_3$), 6.75-6.70 (3H, m, 2-CH of phenyl, —CH of Ru—Ar), 6.62-6.57 (3H, m, —CH of phenyl), 6.44 (2H, d, J 7.2, —CH of phenyl), 6.11-6.02 (2H, m, —CH of Ru—Ar), 4.78 (1H, d, J 5.1, —CH of Ru—Ar), 5.20 (1H, d, J 5.7, —CH of Ru—Ar), 4.95 (1H, d, J 12.0, —CHNH—CH$_2$—), 4.74 (1H, d, J 13.5, —NH—CHH—), 4.10 (1H, d, J 11.3, —CHNTs), 3.85 (1H, d, J 13.5, —NH—CHH—), 3.33-3.25 (1H, dd, J 12.0, 11.3, —CHNH—CH$_2$—), 2.21 (3H, s, —CH$_3$).

m/z ESI-MS [M-Cl]$^+$ 633.1; HRMS found 633.1159 (C$_{34}$H$_{31}$N$_2$O$_2$RuS—Cl+ requires 615.1257, error=−1.4 ppm).

Example 5

Preparation of '3,5-dimethoxy' or 'di-OMe' Catalyst

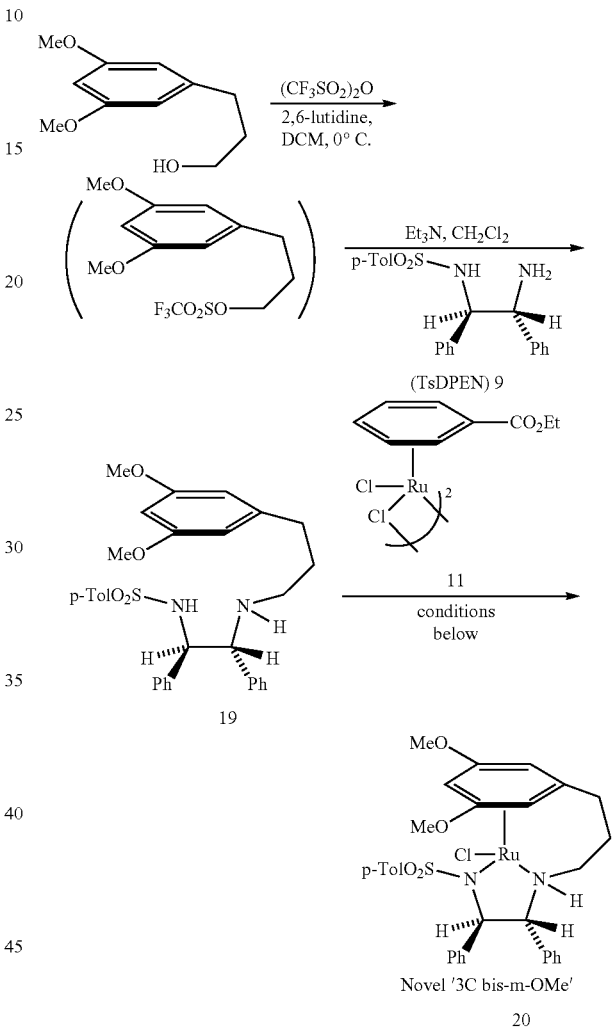

Procedure for the Preparation of 19 from 3-(3,5-(dimethoxy)phenyl)propanol.

To a mixture of 3-(3,5-(dimethoxy)phenyl)propanol (C$_{11}$H$_{16}$O$_3$, 0.428 g, 2.186 mmol, 1.6 eq) and 2,6-lutidine (0.334 mL, 2.869 mmol, 2.10 eq) in dry DCM (10 mL) was added a solution of triflic anhydride (0.390 mL, 2.322 mmol, 1.70 eq) in dry DCM (2.5 mL) dropwise at 0° C. under an inert atmosphere. The resulting light pink solution was stirred at 0° C. for 30 min and at room temperature for 60 min. The mixture was again cooled down to 0° C. To this, a solution of (1R,2R)TsDPEN (0.500 g, 1.366 mmol, 1.0 eq) and TEA (0.456 mL, 3.278 mmol, 2.4 eq) in dry DCM (2.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×25 mL). The organic layer was separated, washed with H$_2$O (2×15 mL), brine (25 mL), dried over anhydrous Na₂SO₄, filtered and concentrated to give crude compound. The crude compound was purified by column chromatography on silica gel using EtOAc:Pet. ether (25:75) as an eluent to give residue. The residue was triturated in n-pentane (to remove traces of 2,6-lutidine) to give solid. The solid was filtered, washed with n-pentane and dried under vacuum to give pure compound 19 as an oil (0.610 g, 1.121 mmol, 82%).

$\delta_H$ (400 MHz, CDCl₃) 7.36 (2H, d, J 8.4, o-CH of —SO₂C₆H₄CH₃), 7.14-7.09 (3H, m, —CH of phenyl), 7.06-7.00 (5H, m, —CH of phenyl), 6.93-6.88 (4H, m, —CH of phenyl), 6.29 (1H, t, J 2.2, —CH of —C₆H₃ (OCH₃)₂), 6.27 (2H, d, J 2.2, —CH of —C₆H₃ (OCH₃)₂), 6.25 (1H, br s, —NHTs), 4.24 (1H, d, J 7.8, —CHNHTs), 3.78 (6H, S, (—OCH₃)₂), 3.59 (1H, d, J 7.8, —CHNH(CH₂)₃—), 2.55-2.40 (3H, m, —NH—CHHCH₂CH₂—), 2.34-2.28 (1H, m, —NH—CHHCH₂CH₂—), 2.32 (3H, s, —CH₃), 1.76-1.62 (2H, m, —NH—CH₂CH₂CH₂—), 1.35 (1H, br s, —NH (CH₂)₃—).

m/z ESI-MS [M+H]⁺ 545.2; HRMS found 545.2475 (C₃₂H₃₆N₂O₄S H+ requires 545.2469, error=−1.1 ppm).

Procedure for the Preparation of 20 from 19.

Compound 19 (C₃₂H₃₆N₂O₄S, 0.125 g, 0.230 mmol, 1.0 eq) and [RuCl₂(C₉H₁₀O₂)]₂ (0.074 g, 0.115 mmol, 0.5 eq) were dissolved in dry DCM (4.5 mL) in a glass tube under N₂. The tube was sealed and mixture was stirred at room temp for 30 min to give brick red solution and heated at 90° C. for 49 h. The reaction was followed by TLC and mass spectra analysis. The reaction mixture was cooled to room temperature and concentrated to give a dark brown residue. The residue was precipitated from diethyl ether, filtered and dried to give a dark brown solid. The solid was purified by column chromatography over Florisil using DCM:MeOH (97:3 to 88:12) to give brown solid. The solid was recrystallized from MeOH to give 20 as a golden orange solid (0.075 g, 0.110 mmol, 48%).

$\delta_H$ (400 MHz, CDCl₃) 7.45 (2H, d, J 8.4, o-CH of —SO₂C₆H₄CH₃), 7.12-7.07 (3H, m, —CH of phenyl), 6.86-6.84 (3H, m, —CH of phenyl), 6.77-6.73 (4H, m, —CH of phenyl), 6.64 (2H, d, J 7.2, —CH of phenyl), 5.89 (1H, s, —CH of Ru—Ar), 4.78 (1H, s, —CH of Ru—Ar), 4.76 (1H, s, —CH of Ru—Ar), 4.39 (1H, d, J 12.6, —NH(CH₂)₃—), 4.17 (3H, s, OCH₃), 4.15 (3H, s, OCH₃), 4.07 (1H, d, J 10.3, —CHNTs), 3.59 (1H, m, —CHNH(CH₂)₃—), 2.70-2.65 (2H, m, —NH—CH₂CH₂CH₂—), 2.62-2.58 (1H, m, —NH—CHHCH₂CH₂—), 2.24 (3H, s, —CH₃), 2.20-2.15 (1H, m, —NH—CHHCH₂CH₂—), 2.11-2.03 (1H, m, —NH—CH₂CHHCH₂—), 1.90-1.85 (1H, m, —NH—CH₂CHHCH₂—).

m/z ESI-MS [M-Cl]⁺ 645.1; HRMS found 645.1365 (C₃₂H₃₅N₂O₄RuS—Cl+ requires 645.1363, error=−0.2 ppm).

Example 6

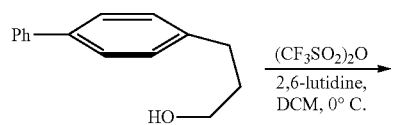

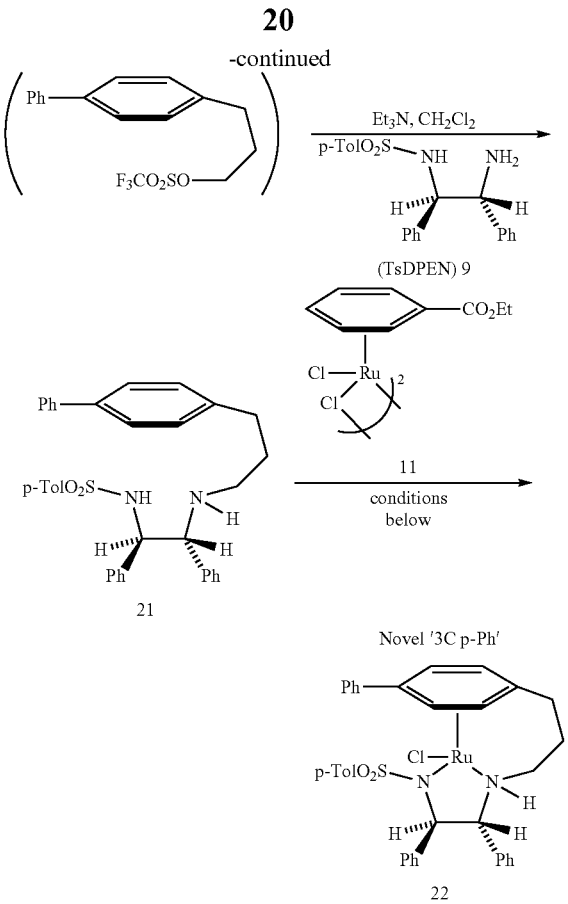

Procedure for the Preparation of 21 from 3-(4-phenylphenyl)propanol.

To a mixture of 3-(4-phenylphenyl)propanol (C₁₅H₁₆O, 0.232 g, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) in dry DCM (1.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R) TsDPEN (0.250 g, 0.683 mmol, 1.0 eq) and TEA (0.228 mL, 1.639 mmol, 2.4 eq) in dry DCM (1.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO₃ solution (3×10 mL). The organic layer was separated, washed with H₂O (2×10 mL), brine (10 mL), dried over anhydrous Na₂SO₄, filtered and concentrated to give crude compound. The crude compound was purified by column chromatography over silica gel using EtOAc:Pet. ether (25:75) as an eluent to give a residue. The residue was triturated in n-pentane (to remove traces of 2,6-lutidine) to give a solid. The solid was filtered, washed with n-pentane and dried under vacuum to give pure compound 21 as a white solid (0.318 g, 0.568 mmol, 83%).

$\delta_H$ (300 MHz, CDCl₃) 7.59-7.56 (2H, m, —CH of phenyl), 7.36 (2H, d, J 8.1, o-CH of —SO₂C₆H₄CH₃), 7.45-7.30 (5H, m, —CH of phenyl), 7.17-7.11 (5H, m, —CH of phenyl), 7.07-6.99 (5H, m, —CH of phenyl), 6.96-6.89 (4H, m, —CH of phenyl), 6.27 (1H, br s, —NHTs), 4.26 (1H, d, J 7.8, —CHNHTs), 3.61 (1H, d, J 7.8, —CHNH(CH₂)₃—), 2.66-2.52 (2H, m, —NH—CH₂CH₂CH₂—), 2.50-2.42 (1H, m, —NH—CHHCH$_2$CH$_2$—), 2.36-2.28 (1H, m, —NH—CHHCH$_2$CH$_2$—), 2.32 (3H, s, —CH$_3$), 1.81-1.66 (2H, m, —NH—CH$_2$CH$_2$CH$_2$—), 1.37 (1H, br s, —NH(CH$_2$)$_3$—).

m/z ESI-MS [M+H]$^+$ 561.2; HRMS found 561.2571 (C$_{36}$H$_{36}$N$_2$O$_2$S H+ requires 561.2570, error=0.3 ppm).

Procedure for the Preparation of 22 from 21.

Compound 21 (C$_{36}$H$_{36}$N$_2$O$_2$S, 0.200 g, 0.357 mmol, 1.0 eq) and [RuCl$_2$(C$_9$H$_{10}$O$_2$)]$_2$ 11 (0.115 g, 0.179 mmol, 0.5 eq) were added to dry DCM (6.0 mL) in a glass tube under N$_2$. The tube was sealed and the mixture was stirred at room temp for 30 min to give brick red solution and heated at 90° C. for 49 h. The reaction was followed by TLC and mass spectra analysis. The reaction mixture was cooled to room temperature and concentrated to give a dark brown residue. The residue was precipitated from diethyl ether, filtered and dried to give a dark brown solid. The solid was purified by column chromatography over Florisil using DCM:MeOH (97:3 to 88:12) to give 22 as a brown solid (0.079 g, 0.114 mmol, 31.8%) as a mixture of isomers with ratio 0.75:0.25 (A:B by $^1$H-NMR in CDCl$_3$).

δ$_H$ (400 MHz, CDCl$_3$) 7.98 (1.5H, d, J 7.6, A —CH of phenyl), 7.81 (0.5H, d, J 6.4, B —CH of phenyl), 7.49-7.38 (4H, m, A+B —CH of phenyl, A —CH of Ru—Ar), 7.23 (0.25H, d, J 7.8, A —CH of phenyl), 7.18-7.04 (5H, m, A+B —CH of phenyl, A —CH of Ru—Ar), 6.89-6.72 (2H, m, A+B —CH of phenyl, B —CH of Ru—Ar), 6.80-6.72 (4H, m, A+B —CH of phenyl), 6.67-6.62 (2H, m, A+B —CH of phenyl), 6.57 (0.75H, d, J 7.8, A —CH of phenyl), 6.26 (0.75H, d, J 5.6, A —CH of Ru—Ar), 5.86 (0.25H, d, J 5.2, B —CH of Ru—Ar), 5.62 (0.25H, br s, B —CH of Ru—Ar), 5.41 (0.75H, d, J 5.2, A —CH of Ru—Ar), 5.23 (0.25H, br d, B —CHNTs), 5.15 (0.75H, d, J 5.6, A —CH of Ru—Ar), 4.99 (0.25H, br d, B —CHNH(CH$_2$)$_3$—), 4.73 (0.75H, d, J 12.0, A —NH(CH$_2$)$_3$—), 4.06 (0.75H, d, J 10.8, A —CHNTs), 3.64-3.58 (0.75H, m, A —CHNH(CH$_2$)$_3$—), 2.91-2.60 (3H, m, A+B —NH—CHHCH$_2$CH$_2$—), 2.36-2.25 (1H, m, A+B —NH—CHHCH$_2$CH$_2$—), 2.20 (2.25H, s, A —CH$_3$), 2.12 (0.75H, s, B —CH$_3$), 2.11-2.04 (2H, m, -A+B NH—CH$_2$CH$_2$CH$_2$—), (peak not identified for (0.25H) B —NH(CH$_2$)$_3$—).

m/z ESI-MS [M-Cl]$^+$ 661.1; HRMS found 661.1458 (C$_{36}$H$_{35}$N$_2$O$_2$RuS—Cl+ requires 661.1466, error=1.5 ppm).

Example 7

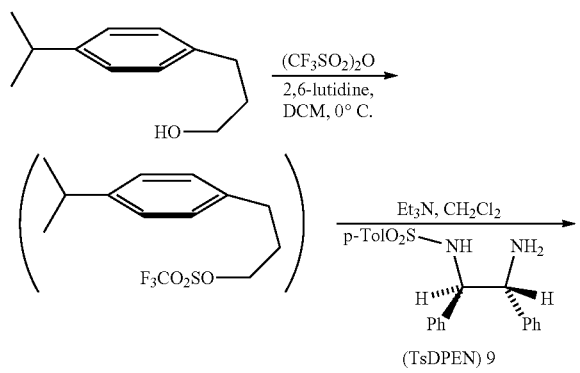

(TsDPEN) 9

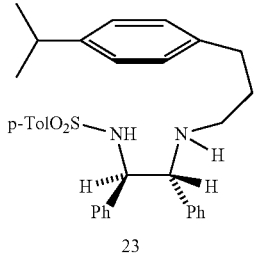

23

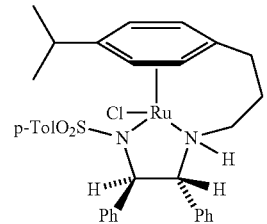

Novel '3C p-iPr'

24

Procedure for the Preparation of 23 from 3-(4-isopropylphenyl)propanol.

To a mixture of 3-(4-isopropylphenyl)propanol (C$_{12}$H$_{18}$O, 0.195 g, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) in dry DCM (1.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R) TsDPEN (0.250 g, 0.683 mmol, 1.0 eq) and TEA (0.228 mL, 1.639 mmol, 2.4 eq) into dry DCM (1.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×10 mL). The organic layer was separated, washed with H$_2$O (2×10 mL), brine (10 mL), dried over anhydrous Na$_2$SO$_4$, filtered and concentrated to give a crude compound. The crude compound was purified by column chromatography over silica gel using EtOAc:Pet. ether (25:75) as an eluent to give residue. The residue was triturated in n-pentane (to remove traces of 2,6-lutidine) to give a solid. The solid was filtered, washed with n-pentane and dried under vacuum to give pure compound 23 as a white solid (0.340 g, 0.646 mmol, 94.6%).

δ$_H$ (300 MHz, CDCl$_3$) 7.37 (2H, d, J 8.1, o-CH of —SO$_2$C$_6$H$_4$CH$_3$), 7.14-7.09 (5H, m, —CH of phenyl), 7.07-6.99 (7H, m, —CH of phenyl), 6.96-6.87 (4H, m, —CH of phenyl), 6.28 (1H, br s, —NHTs), 4.24 (1H, d, J 7.7, —CHNHTs), 3.59 (1H, d, J 7.7, —CHNH(CH$_2$)$_3$—), 2.94-2.80 (1H, m, —CH(CH$_3$)$_2$), 2.57-2.39 (3H, m, —NH—CHHCH$_2$CH$_2$—), 2.34-2.25 (1H, m, —NH—CHHCH$_2$CH$_2$—), 2.32 (3H, s, —CH$_3$), 1.78-1.60 (2H, m, —NH—CH$_2$CH$_2$CH$_2$—), 1.23 (6H, d, J 6.9, —CH(CH$_3$)$_2$), (peak not identified for —NH(CH$_2$)$_3$—).

m/z ESI-MS [M+H]$^+$ 527.2; HRMS found 527.2735 (C$_{33}$H$_{38}$N$_2$O$_2$S H+ requires 527.2727, error=−0.6 ppm).

Procedure for the Preparation of 24 from 23.

Compound 23 (C$_{33}$H$_{38}$N$_2$O$_2$S, 0.200 g, 0.380 mmol, 1.0 eq) and [RuCl$_2$(C$_9$H$_{10}$O$_2$)]$_2$ 11 (0.122 g, 0.190 mmol, 0.5 eq)

were dissolved in dry DCM (6.0 mL) in a glass tube under N₂. The tube was sealed and the mixture was stirred at room temp for 30 min to give brick red solution and heated at 90° C. for 49 h. The reaction was followed by TLC and mass spectra analysis. The reaction mixture was cooled to room temperature and concentrated to give a brown residue. The solid was precipitated from diethyl ether, filtered and dried to give a dark brown solid. The solid was purified by column chromatography over Florisil using DCM:MeOH (97:3 to 88:12) to give 24 as a brown solid (0.073 g, 0.110 mmol, 28%) as a mixture of isomers with ratio 0.8:0.2 (A:B by ¹H-NMR in CDCl₃).

$\delta_H$ (400 MHz, CDCl₃) 7.39-7.29 (2H, m, A+B —CH of phenyl), 7.18-7.04 (4H, m, A+B —CH of phenyl), 6.87-6.77 (4H, m, A+B —CH of phenyl), 6.75-6.65 (2H, m, A+B —CH of phenyl), 6.60-6.58 (2H, m, A+B —CH of phenyl), 6.44 (0.2H, d, J 4.8, B —CH of Ru—Ar), 6.36 (0.8H, d, J 5.6, A —CH of Ru—Ar), 5.96 (0.8H, d, J 6.0, A —CH of Ru—Ar), 5.91 (0.2H, d, J 5.6, B —CH of Ru—Ar), 5.46 (0.2H, br d, B —CH of Ru—Ar), 5.36 (0.2H, br d, B —CH of Ru—Ar), 5.18 (1H, d, J 5.6, A —CH of Ru—Ar, B —CHNTs), 4.99 (0.8H, d, J 6.0, A —CH of Ru—Ar), 4.83 (0.2H, d, J 12, B —CHNH(CH₂)₃—), 4.53 (0.8H, d, J 12.0, A —NH(CH₂)₃—), 4.10 (0.8H, d, J 10.8, A —CHNTs), 3.73-3.67 (0.8H, m, A —CHNH(CH₂)₃—), 3.62-3.52 (0.8H, m, A —CH(CH₃)₂), 3.19-3.10 (0.2H, m, B —CH(CH₃)₂), 2.87-2.59 (3H, m, A+B —NH—CHHCH₂CH₂—), 2.29-2.13 (2H, m, A+B —NH—CHHCHHCH₂—), 2.24 (2.4H, s, A —CH₃), 2.15 (0.6H, s, B —CH₃), 2.08-2.02 (1H, m, -A+B NH—CH₂CHHCH₂—), 1.58 (2.4H, d, J 6.8, A —CH(CH₃)₂), 1.40 (0.6H, d, J 6.4, B —CH(CH₃)₂), 1.58 (0.6H, d, J 6.8, B —CH(CH₃)₂), 1.25 (2.4H, d, J 6.8, A —CH(CH₃)₂), (peak not identified for (0.2H) B —NH(CH₂)₃—).

m/z ESI-MS [M-Cl]⁺ 627.1; HRMS found 627.1611 (C₃₃H₃₇N₂O₂RuS—Cl+ requires 627.1622, error=1.3 ppm).

Example 8

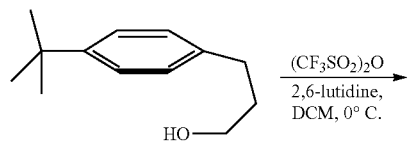

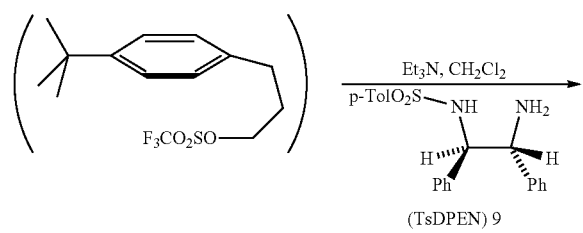

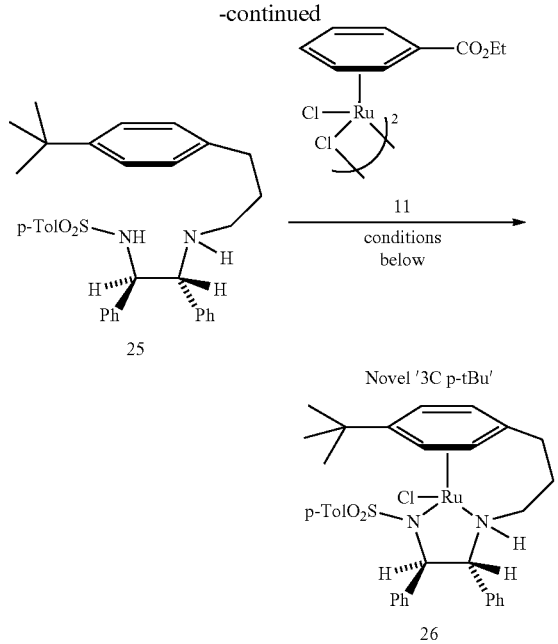

Procedure for the Preparation of 25 from 3-(4-tertbutylphenyl)propanol.

To a mixture of 3-(4-tertbutylphenyl)propanol (C₁₃H₂₀O, 0.210 g, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) in dry DCM (1.5 mL) dropwise at 0° C. under an inert atmosphere. The resulting light pink solution was stirred at 0° C. for 30 min and at room temperature for 60 min. The mixture was again cooled down to 0° C. To this, a solution of (1R,2R) TsDPEN 9 (0.250 g, 0.683 mmol, 1.0 eq) and TEA (0.228 mL, 1.639 mmol, 2.4 eq) in dry DCM (1.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO₃ solution (3×10 mL). The organic layer was separated, washed with H₂O (2×10 mL), brine (10 mL), dried over anhydrous Na₂SO₄, filtered and concentrated to give a crude compound. The crude compound was purified by column chromatography over silica gel using EtOAc:Pet. ether (25:75) as an eluent to give a residue. The residue was triturated in n-pentane (to remove traces of 2,6-lutidine) to give solid. The solid was filtered, washed with n-pentane and dried under vacuum to give pure compound 25 as a white solid (0.312 g, 0.578 mmol, 84.6%).

$\delta_H$ (300 MHz, CDCl₃) 7.37 (2H, d, J 8.4, o-CH of —SO₂C₆H₄CH₃), 7.29-7.25 (2H, m, —CH of phenyl), 7.14-7.11 (3H, m, —CH of phenyl), 7.05-7.00 (7H, m, —CH of phenyl), 6.96-6.87 (4H, m, —CH of phenyl), 6.28 (1H, br s, —NHTs), 4.24 (1H, d, J 8.0, —CHNHTs), 3.59 (1H, d, J 8.0, —CHNH(CH₂)₃—), 2.57-2.39 (3H, m, —NH—CHHCH₂CH₂—), 2.34-2.26 (1H, m, —NH—CHHCH₂CH₂—), 2.32 (3H, s, —CH₃), 1.76-1.63 (2H, m, —NH—CH₂CH₂CH₂—), 1.30 (10H, br s, —C(CH₃)₃ and —NH(CH₂)₃—).

m/z ESI-MS [M+H]⁺ 541.2; HRMS found 541.2888 (C₃₄H₄₀N₂O₂S H+ requires 541.2883, error=-0.6 ppm).

Procedure for the Preparation of 26 from 25.

Compound 25 (C₃₄H₄₀N₂O₂S, 0.200 g, 0.370 mmol, 1.0 eq) and [RuCl₂(C₉H₁₀O₂)]₂ 11 (0.119 g, 0.185 mmol, 0.5 eq)

into dry DCM (6.0 mL) in a glass tube under $N_2$. The tube was sealed and mixture was stirred at room temp for 30 min to a give brick red solution and heated at 90° C. for 49 h. The reaction mixture was cooled to room temperature and concentrated to give a dark brown residue. The residue was precipitated from diethyl ether, filtered and dried to give brown solid. The solid was purified by column chromatography over Florisil using DCM:MeOH (97:3 to 88:12) to give 26 as a brown solid (0.052 g, 0.078 mmol, 20.8%) as a mixture of isomers with ratio 0.55:0.45 (A:B by $^1$H-NMR in $CDCl_3$).

$\delta_H$ (400 MHz, $CDCl_3$) 7.30 (1.1H, d, J 8.0, A —CH of phenyl), 7.22 (0.9H, d, J 8.0, B —CH of phenyl), 7.17-7.11 (2H, m, A+B —CH of phenyl, A+B —CH of Ru—Ar), 7.09-7.02 (3H, m, A+B —CH of phenyl), 6.99-6.98 (1H, m, A+B —CH of phenyl), 6.77-6.75 (2H, m, A+B —CH of phenyl), 6.71-6.33 (3H, m, A+B —CH of phenyl, A+B —CH of Ru—Ar), 6.58-6.54 (2H, m, A+B —CH of phenyl), 5.87-5.84 (1H, m, A+B —CH of Ru—Ar), 5.69 (0.45H, br s, B —CH of Ru—Ar), 5.60 (0.55H, d, J 5.2, A —CH of Ru—Ar), 5.48 (0.45H, br s, B —CH of Ru—Ar), 5.21-5.17 (1H, m, A —CH of Ru—Ar, B —CHNTs), 4.78 (0.45H, br d, B —CHNH$(CH_2)_3$—), 4.68 (0.55H, d, J 10.8, A —CHNTs), 4.30 (0.55H, br d, A NH$(CH_2)_3$—), 3.87-3.81 (0.55H, m, A —CHNH$(CH_2)_3$—), 2.85-2.54 (3H, m, A+B —NH—CHHCH$_2$CH$_2$—), 2.37-2.27 (1H, m, A+B —NH—CHHCH$_2$CH$_2$—), 2.16-2.08 (2H, m, A+B —NH—CH$_2$CH$_2$CH$_2$—), 2.19 (1.65H, s, A —CH$_3$), 2.13 (1.35H, s, B —CH$_3$), 1.60 (4.95H, s, A —C(CH$_3$)$_3$), 1.55 (4.05H, s, B —C(CH$_3$)$_3$), (peak not identified for (0.45H) B —NH$(CH_2)_3$—).

m/z ESI-MS [M-Cl]$^+$ 641.1; HRMS found 641.1777 ($C_{34}H_{39}N_2O_2RuS$—Cl+ requires 641.1778, error=0.3 ppm).

Example 9

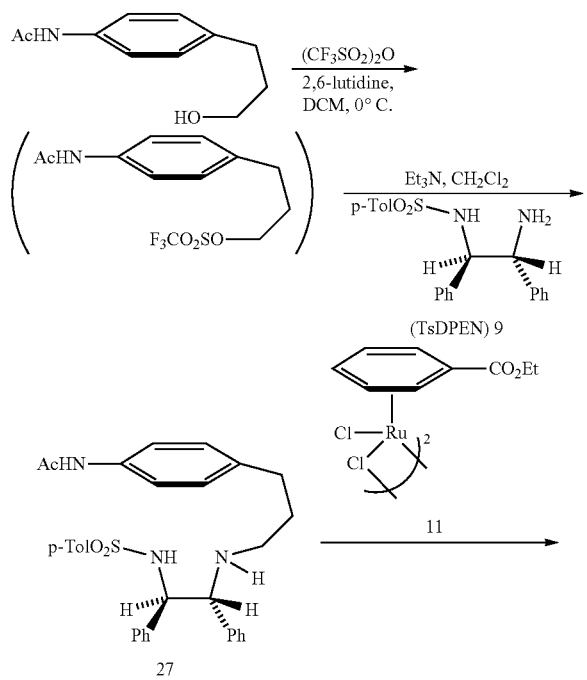

-continued

Novel '3C NAc'

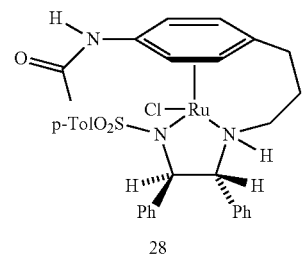

28

To a mixture of (1R,2R)-TsDPEN 9 (0.318 g, 0.870 mmol, 1.0 eq) and MS 4A (0.5 g) in dry methanol (10 mL) was added 3-(4-acetylaminophenyl)propanol ($C_{11}H_{13}NO_2$, 0.191 g, 1.0 mmol, 1.15 eq) followed by acetic acid (2-3 drops). The mixture was stirred at room temperature under an inert atmosphere for 4.5 h to form the imine. To this, NaBH$_3$CN (0.227 g, 3.611 mmol, 4.15 eq) was added and resulting mixture was stirred at room temperature for 24 h. The reaction mixture was filtered and concentrated to give a residue. This was dissolved in DCM (20 mL) and washed with 1M NaOH (2×15 mL), dried over anhydrous Na$_2$SO$_4$, filtered and evaporated on a rotavapor to give the crude product. The crude compound was purified by flash column chromatography over silica gel using EtOAc:Pet. ether (7:3) to give compound 27 as a white solid (0.380 g, 0.702 mmol, 80.8%).

$\delta_H$ (300 MHz, $CDCl_3$) 7.39-7.34 (5H, m, —CH of phenyl), 7.12-7.10 (3H, m, —CH of phenyl), 7.05-7.00 (6H, m, —CH of phenyl), 6.92-6.87 (4H, m, —CH of phenyl), 6.26 (1H, br s, —NHTs), 4.22 (1H, d, J 7.8, —CHNHTs), 3.57 (1H, d, J 7.8, —CHNH(CH$_2$)$_3$—), 2.56-2.38 (3H, m, —NH—CHHCH$_2$CH$_2$—), 2.33-2.22 (1H, m, —NH—CHHCH$_2$CH$_2$—), 2.32 (3H, s, —CH$_3$), 2.13 (3H, s, —COCH$_3$), 1.71-1.60 (2H, m, —NH—CH$_2$CH$_2$CH$_2$—), 1.48 (1H, br s, —NH(CH$_2$)$_3$—).

m/z ESI-MS [M+H]$^+$ 542.2; HRMS found 542.2476 ($C_{32}H_{35}N_3O_3S$ H+ requires 542.2472, error=0.2 ppm).

Procedure for the Preparation of 28 ('3C p-NAc') from 27.

Compound 27 ($C_{32}H_{33}N_3O_2S$, 0.100 g, 0.185 mmol, 1.0 eq) and [RuCl$_2$(C$_9$H$_{10}$O$_2$)]$_2$ 11 (0.060 g, 0.093 mmol, 0.5 eq) were dissolved in dry DCM (4.5 mL) under N$_2$, and stirred at room temp for 60 min to give a brick red solution. The mixture was concentrated on a rotavpor to give dark orange residue. To this, chlorobenzene (12 mL) was added and mixture heated at 100° C. for 5 h. The reaction mixture was cooled to room temperature and concentrated to give dark brown residue. The solid was scratched in diethyl ether, filtered and dried to give dark brown solid. The solid was purified by column chromatography over Florisil using DCM:MeOH (97:3 to 88:12) to give 28 as a brown solid. (0.033 mg, 0.049 mmol, 26%).

$\delta_H$ (400 MHz, $CDCl_3$) 9.39 (1H, s, —NHCOCH$_3$), 7.25 (2H, d, J 8.0, —CH of phenyl), 7.13-7.02 (3H, m, —CH of phenyl), 6.89-6.84 (2H, m, —CH of phenyl), 6.82-6.75 (3H, m, —CH of phenyl), 6.71-6.67 (2H, m, —CH of phenyl), 6.62-6.52 (3H, m, —CH of phenyl, —CH of Ru—Ar), 6.25 (1H, d, J 5.6, —CH of Ru—Ar), 5.26 (1H, d, J 5.6, —CH of Ru—Ar), 5.22 (1H, m, —CH of Ru—Ar), 4.44 (1H, br d, —NH(CH$_2$)$_3$—), 4.09 (1H, d, J 10.8, —CHNTs), 3.69 (1H, m, —CHNH(CH$_2$)$_3$—), 2.82-2.55 (3H, m, —NH—CHHCH$_2$CH$_2$—), 2.36-2.28 (1H, m, —NH—CHHCH$_2$CH$_2$—), 2.24 (3H, s, —CH$_3$), 2.07 (3H, s, —NH-COCH$_3$), 2.06-1.98 (2H, m, —NH—CH$_2$CH$_2$CH$_2$—).

m/z ESI-MS [M-Cl]+ 642.1; HRMS found 642.1374 ($C_{32}H_{34}N_3O_3RuS$—Cl+ requires 642.1366, error=−1.5 ppm).

Example 10

Asymmetric Transfer Hydrogenation (ATH) Reduction with Formic Acid/Triethylamine The asymmetric reduction of prochiral ketones to alcohols through the process of asymmetric transfer hydrogenation (ATH) has been studied. ATH requires the use of an organic molecule as the source of hydrogen in the reduction reaction. Typically this is formic acid, isopropanol or sodium formate. In our investigation we have used the most common reagent; a 5:2 formic acid:triethylamine mixture.

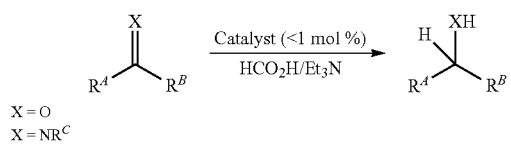

X = O
X = $NR^C$

To a mixture of catalyst (0.002 mmol) in FA:TEA (5:2) (1.0 mL) was added ketone/imine (2.0 mmol) and stirred at 60° C. for 1 h-31 h under an inert atmosphere. The reaction was monitored by chiral GC. For chiral GC analysis, the small sample from reaction mixture was filtered through a plug of silica using hexane:EtOAc (1:1). The filtrate was analysed by chiral GC. After completion of reaction, (i) for ketone reduction:reaction mixture was filtered through silica using EtOAc. The filtrate was concentrated to give a crude alcohol. The crude compound was purified by flash column chromatography over silica gel to give pure alcohol; (ii) for imine reduction:reaction mixture was concentrated, diluted with DCM and washed with sat. $NaHCO_3$ solution. The organic layer was separated, dried over anhydrous $Na_2SO_4$, filtered and concentrated to give amine.

Example 11

Asymmetric Hydrogenation (AH) Reduction with Hydrogen Gas

The asymmetric reduction of prochiral ketones to alcohols through the process of pressure hydrogenation (AH) has been studied. AH requires the use of hydrogen gas as the source of hydrogen in the reduction reaction. The results below contrast the results obtained using the new complexes with those reported previously for a series of other catalysts which have been reported previously (A. M. Hayes, D. J. Morris, G. J. Clarkson and M. Wills, *Am. Chem Soc*, 2005, vol 127, 7318-7319)

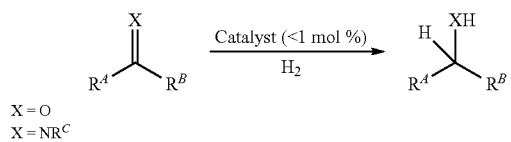

X = O
X = $NR^C$

To a Pyrex test tube was added the substrate (1 mmol) followed by the catalyst (0.002 mmol). To this was then added MeOH (2 mL). The test tube was then placed into a Parr reactor which was sealed and purged with hydrogen gas. The reactor was then charged to a pressure of 30 bar hydrogen gas, heated to the required temperature (60° C.) and stirred for the required time. Once complete the reactor was allowed to cool to room temperature and the pressure released. The reaction solution was filtered through silica with 1:1 EtOAc:petroleum ether 40-60 solution to remove the catalyst. The filtrate was dried by rotary evaporation to give the product which was analysed by gas chromatography or HPLC.

The p-OMe catalyst 16 is capable of generating high enantiomeric inductions in reductions of a range of prochiral ketones, often giving improved results in terms of conversion and/or enantioselectivity compared to published catalysts.

Alternative Conditions for Complexations via Arene Exchange using Complexes

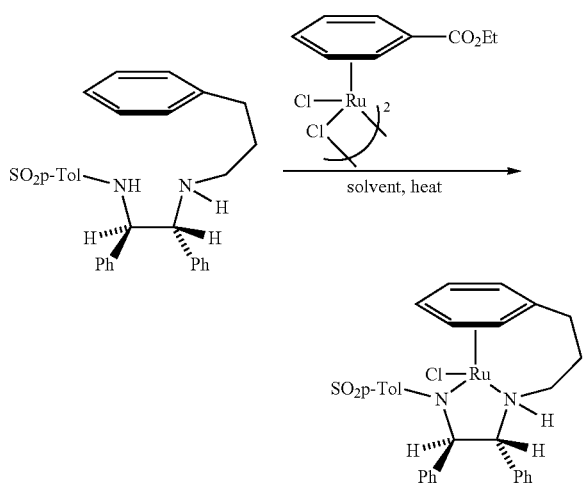

The reaction can be followed by mass spectrometry. The peak at m/z 485 is the ligand and the product ([M-Cl]+) is at ca. m/z 585. ESI-MS illustrates the conversion of ligand to tethered complex, without formation of the unwanted bidentate complex. An example of an ESI-MS after 46 h—heating in DCM, 90° C. is shown in FIG. 1.

Selected alternative variations: (i) Ligand and [$RuCl_2$(1,4-($EtO_2C$)$_2C_6H_4$)]$_2$ in DCM at rt for 30 min and heated at 90° C. for 49 h; formation of required complex. (ii) Ligand and [$RuCl_2$(1,4-($EtO_2C$)($CH_3$)$C_6H_4$)]$_2$ in DCM at rt for 30 min and heated at 90° C. for 49 h; formation of complex in lower conversion. (iii) Ligand and [Ru($C_6H_5CO_2Et$)$Cl_2$]$_2$ in DCM at rt for 30 min followed by heating in chlorobenzene at 140° C. for 2 h; formation of required complex. Thin layer chromatography (TLC) on silica gel can also be used to follow the reactions.

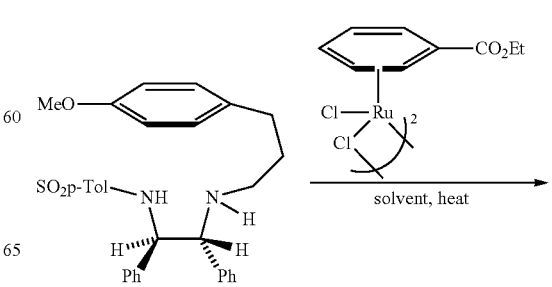

Novel '3C p-OMe'

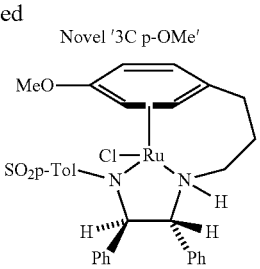

The reaction can be followed by mass spectrometry. An example of 4-methoxy ESI-MS after 51.5 h—heating in DCM, 90° C.; ligand is at m/z 515, complex [M-Cl] is at m/z 615 is shown in FIG. 2.

Selected alternative variations: (i) Ligand and [RuCl$_2$(1,4-(EtO$_2$C)$_2$C$_6$H$_4$)]$_2$ in DCM at rt for 30 min and heated at 90° C. for 49 h; formation of required complex; (ii) Ligand and [RuCl$_2$(1,4-(EtO$_2$C)(CH$_3$)C$_6$H$_4$)]$_2$ in DCM at rt for 30 min and heated at 90° C. for 49 h; formation of required complex in lower conversion; (iii) Ligand and [Ru(C$_6$H$_5$CO$_2$Et)Cl$_2$]$_2$ in DCM at rt for 30 min then reaction in chlorobenzene at 140° C. for 2 h; formation of the required complex. Ligand and [Ru(C$_6$H$_5$CO$_2$Et)Cl$_2$]$_2$ stirred for 1 hour in DCM which was then replaced with chlorobenzene, and heated for 6 h at 90° C.: 100 mg ligand gave 90 mg product from column (69%), which was recrystallized to give 50 mg solid (38%). At 75° C., reaction appeared complete after 6 hours in chlorobenzene. Also complete after 5 h heating in chlorobenzene at 90° C., or 3 h in chlorobenzene at 100° C. Thin layer chromatography (TLC) on silica gel can also be used to follow the reactions. The combination of ligand and [Ru(C$_6$H$_5$CO$_2$Et)Cl$_2$]$_2$ in DCM at rt formed only a bidentate complex. The following bases —Ca(OH)$_2$, NaHCO$_3$, K$_2$CO$_3$, Mg(OH)$_2$ can be added to the reaction however strong NaOH and Et$_3$N are detrimental, leading to formation of an unwanted bidentate complex. Mass spectrometry traces of reactions with added base were recorded.

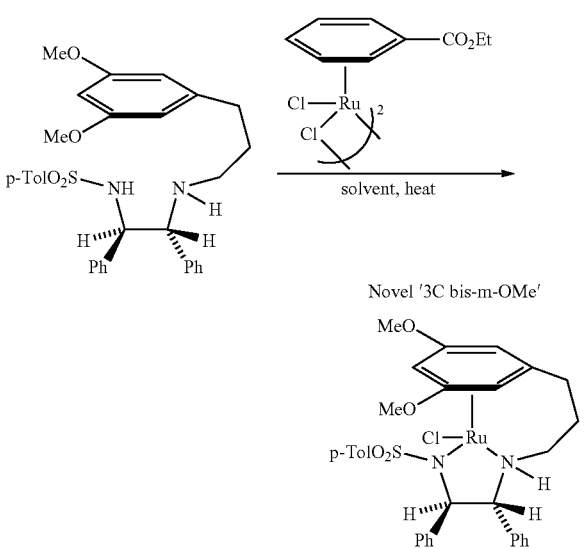

Novel '3C bis-m-OMe'

The reaction can be followed by mass spectrometry. An example of 2,4-Dimethoxy ESI-MS after 48 h heating in DCM, 90° C.; ligand is at m/z 545, complex is at m/z 645 ([M-Cl]+ is shown in FIG. 3.

Reaction of ligand with [Ru(C$_6$H$_5$CO$_2$Et)Cl$_2$]$_2$ in DCM at room temperature for 30 min followed by in chlorobenzene at 140° C. for 2 h, resulted in the formation of required complex in 32% isolated yield.

Additional Complexes which have been Prepared and Tested

4-Iodo-N-((1R,2R)-2-(3-(4-methoxyphenyl)propylamino)-1,2-diphenylethyl)benzenesulfonamide SRC 1130/1150

To a mixture of alcohol C$_{10}$H$_{14}$O$_2$ (0.278 g, 1.67 mmol, 1.6 eq) and 2,6-lutidine (0.255 mL, 2.197 mmol, 2.10 eq) into dry DCM (10 mL) was added a solution of triflic anhydride (1M in DCM) (1.78 mL, 1.778 mmol, 1.70 eq) dropwise at 0° C. under an inert atmosphere. The resulting light pink solution was stirred at 0° C. for 30 min and at room temperature for 60 min. The mixture was again cooled to 0° C. To this, a solution of diamine C$_{20}$H$_{19}$IN$_2$O$_2$S (0.500 g, 1.046 mmol, 1.0 eq) and TEA (0.349 mL, 2.510 mmol, 2.4 eq) in dry DCM (5 mL) was added dropwise at 0° C. The resulting yellow coloured mixture was stirred at 0° C. for 30 min and then at room temperature for 17 h. The reaction mixture was diluted with DCM (15 mL) and washed with sat. NaHCO$_3$ solution (3×10 mL). The organic layer was separated, washed with H$_2$O (2×10 mL), brine (10 mL), dried over anhy. Na$_2$SO$_4$, filtered and concentrated to give the crude compound. The crude compound was purified by column chromatography on silica gel using EtOAc:Pet. ether (30:70) as an eluent to give a product. The product was triturated in n-pentane (to remove traces of 2,6-lutidine). The solvent was evaporated to give the pure compound as white solid (0.439 g, 0.701 mmol, 67%). Mp 122-124° C.; [α]$_D^{28}$=+8.7 (c 0.505 in CHCl$_3$); ν$_{max}$ 3305, 3028, 2997, 2926, 2831, 1611, 1567, 1510, 1493, 1459, 1161, 811, 727, 701 cm$^{-1}$; δ$_H$ (400 MHz, CDCl$_3$) 7.52 (2H, d, J 8.4, —CH of —SO$_2$C$_6$H$_4$I), 7.18-7.04 (8H, m, —CH of phenyl, —CH of —SO$_2$C$_6$H$_4$I), 6.98 (2H, d, J 8.8, —CH of —C$_6$H$_4$(OCH$_3$)), 6.96-6.91 (4H, m, —CH of phenyl), 6.79 (2H, d, J 8.8, —CH of —C$_6$H$_4$(OCH$_3$)), 6.33 (1H, br s, —NHTs), 4.30 (1H, d, J 7.4, —CHNHTs), 3.78 (3H, s, —OCH$_3$), 3.61 (1H, d, J 7.4, —CHNH(CH$_2$)$_3$—), 2.53-2.40 (3H, m, —NH—CHHCH$_2$CH$_2$—), 2.31-2.26 (1H, m, —NH—CHHCH$_2$CH$_2$—), 1.74-1.59 (2H, m, —NH—CH$_2$CH$_2$CH$_2$—), 1.28 (1H, br s, —NH(CH$_2$)$_3$—); δc (100 MHz, CDCl$_3$) 157.75 (C), 139.83 (C), 139.05 (C), 137.94 (C), 137.56 (2CH), 133.70 (C), 129.17 (2CH), 128.38 (4CH), 128.08 (2CH), 127.57 (CH), 127.48 (3CH), 127.24 (2CH), 113.75 (2CH), 99.29 (C), 67.49 (CH), 63.09 (CH), 55.24 (OCH$_3$), 46.40 (CH$_2$), 32.32 (CH$_2$), 31.60 (CH$_2$); m/z ESI-MS [M+H]$^+$ 627.1; HRMS found 627.1174 (C$_{30}$H$_{31}$IN$_2$O$_3$S H+ requires 627.1173, error=–0.1 ppm).

{4-Iodo-N-((1R,2R)-2-(3-(4-methoxyphenyl)propylamino)-1,2-diphenylethyl)benzenesulfonamide}-ruthenium chloride SRC 1135/1312

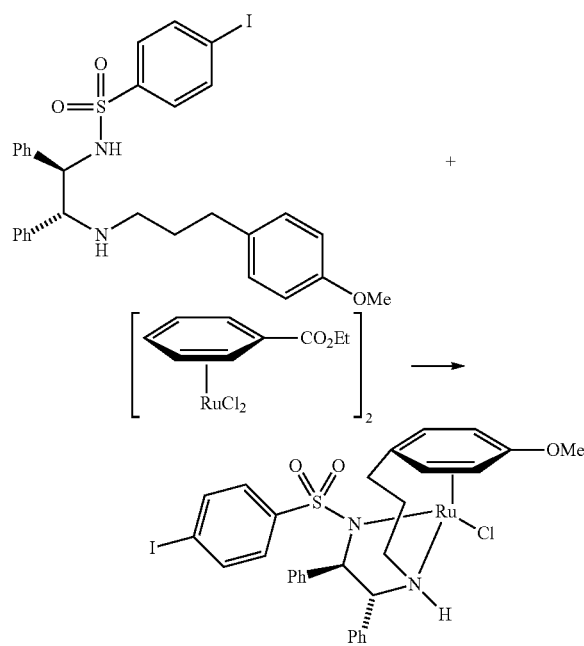

Compound C$_{30}$H$_{31}$IN$_2$O$_3$S (0.300 g, 0.479 mmol, 1.0 eq) and [RuCl$_2$(C$_9$H$_{10}$O$_2$)]$_2$ (0.154 g, 0.150 mmol, 0.5 eq) were dissolved in dry DCM (15 mL) under N$_2$ and stirred at room temp for 30 min to give a brick red solution. The mixture was concentrated on a rotavapor to give a dark orange residue. To this, chlorobenzene (30 mL) was added and mixture heated at 90° C. for 5 h. The reaction mixture was cooled to room temperature and concentrated to give a dark brown residue. The solid was scratched in diethyl ether, filtered and dried to give dark brown solid. The solid was purified by column chromatography over Florisil using DCM:MeOH (97:3 to 86:14) to give compound as a brown solid. The solid was recrystallized from MeOH to give pure product as an orange solid (0.125 g, 0.164 mmol, 34%). Mp decomposition>280° C.; [α]$_D^{28}$=–164.54 (c 0.055 in CHCl$_3$); ν$_{max}$ 3198, 3051, 3027, 2925, 2872, 1572, 1533, 1509, 1465, 1454, 1279, 1266, 1255, 835, 796, 725, 694 cm$^{-1}$; δ$_H$ (500 MHz, CD$_2$Cl$_2$) 7.34 (2H, d, J 8.3, —CH of —SO$_2$C$_6$H$_4$I), 7.23-7.16 (3H, m, —CH of phenyl), 7.10 (2H, d, J 8.3, —CH of —SO$_2$C$_6$H$_4$I), 6.96-6.86 (3H, m, —CH of phenyl), 6.73-6.70 (2H, m, —CH of phenyl), 6.60 (2H, d, J 7.5, —CH of phenyl), 5.55 (1H, d, J 5.8, —CH of Ru—Ar), 5.51 (1H, d, J 5.8, —CH of Ru—Ar), 5.37 (1H, d, J 6.0, —CH of Ru—Ar), 5.31 (1H, d, J 6.0, —CH of Ru—Ar), 4.27 (1H, d, J 11.0, —CHNTs), 4.00-3.96 (1H, m, —NH(CH$_2$)$_3$—), 3.96 (3H, s, —OCH$_3$), 3.68-3.63 (1H, m, —CHNH(CH$_2$)$_3$—), 2.80-2.75 (1H, m, —NH—CHHCH$_2$CH$_2$—), 2.53-2.44 (2H, m, —NH—CHHCH$_2$CHH—), 2.34-2.29 (1H, m, —NH—CH$_2$CH$_2$CHH—), 2.16-2.10 (1H, m, —NH—CH$_2$CHHCH$_2$—), 2.02-1.93 (1H, m, —NH—CH$_2$CHHCH$_2$—); δc (125 MHz, CD$_2$Cl$_2$) 147.61 (C), 138.96 (C), 136.87 (2CH), 136.80 (C), 135.27 (C), 129.45 (2CH), 129.21 (CH), 129.09 (4CH), 128.96 (CH), 127.64 (2CH), 126.83 (2CH), 95.45 (C), 91.85 (C), 85.34 (CH), 81.68 (CH), 79.63 (CH), 72.19 (CH), 69.13 (CH), 65.75 (CH), 57.19 (OCH$_3$), 50.08 (CH$_2$), 31.09 (CH$_2$), 27.63 (CH$_2$); m/z ESI-MS [M-Cl]$^+$ 727.0; HRMS found 727.0072 (C$_{30}$H$_{30}$N$_2$O$_3$RuS—Cl+ requires 727.0067, error=–1.4 ppm).

N-((1R,2R)-2-(3-(4-Methoxyphenyl)propylamino)-1,2-diphenylethyl)-4-(2-(trimethylsilyl)ethynyl)benzenesulfonamide SRC 1134/1156

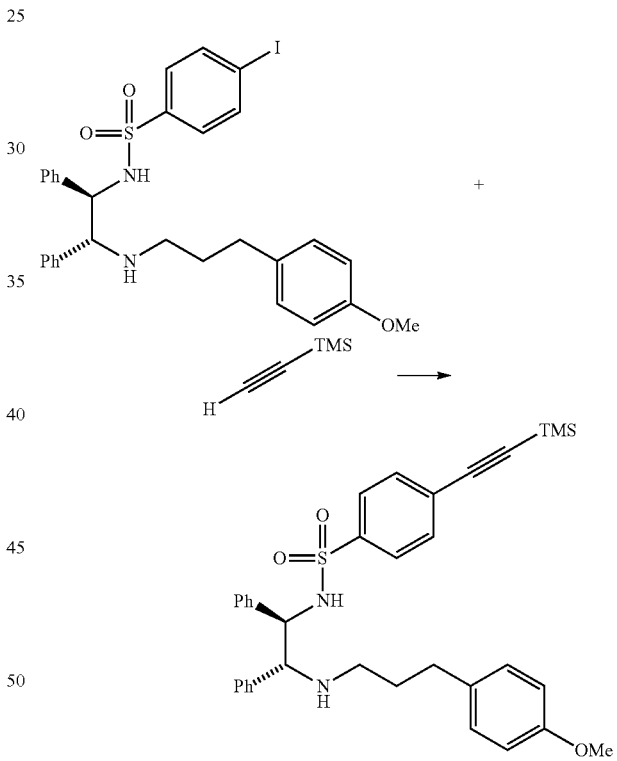

In glass tube diamine C$_{30}$H$_{31}$IN$_2$O$_3$S (0.501 g, 0.8 mmol, 1.0 eq), PdCl$_2$(PPh$_3$)$_4$ (28 mg, 0.040 mmol, 0.05 eq) and CuI (15.3 mg, 0.080 mmol, 0.1 eq) were dissolved in dry THF (10 mL) under an inert atmosphere followed by TEA (2.5 mL). The resulting mixture was stirred for 5 min followed by addition of trimethylsilylacetylene (0.382 mL, 2.71 mmol, 3.89 eq). The glass tube was sealed under an inert atmosphere and stirred at room temperature for 22 h. The reaction mixture was filtered through Celite and washed with EtOAc (2×20 mL). The filtrate was concentrated on a rotavapor to give a residue. The crude compound was purified by column chromatography over silica gel using EtOAc:Pet. ether (26:74) as an eluent to give the pure product as a light green solid (0.426 g, 0.714 mmol, 89%). Mp 48-50° C.; $[\alpha]_D^{28}$=+9.29 (c 0.280 in CHCl$_3$); $\nu_{max}$ 3263, 3060, 3030, 2931, 2834, 2159, 1611, 1590, 1510, 1453, 1395, 1244, 1153, 838, 758, 697 cm$^{-1}$; $\delta_H$ (400 MHz, CDCl$_3$) 7.37 (2H, d, J 8.4, —CH of —SO$_2$C$_6$H$_4$—), 7.28 (2H, d, J 8.4, —CH of —SO$_2$C$_6$H$_4$—), 7.15-7.02 (6H, m, —CH of phenyl), 6.99 (2H, d, J 8.4, —CH of —C$_6$H$_4$(OCH$_3$)), 6.95-6.89 (4H, m, —CH of phenyl), 6.80 (2H, d, J 8.4, —CH of —C$_6$H$_4$(OCH$_3$)), 6.37 (1H, br s, —NHTs), 4.27 (1H, d, J 8.0, —CHNHTs), 3.78 (3H, s, —OCH$_3$), 3.59 (1H, d, J 8.0, —CHNH(CH$_2$)$_3$—), 2.55-2.40 (3H, m, —NH—CHHCH$_2$CH$_2$—), 2.32-2.26 (1H, m, —NH—CHHCH$_2$CH$_2$—), 1.75-1.61 (2H, m, —NH—CH$_2$CH$_2$CH$_2$—), 1.37 (1H, br s, —NH(CH$_2$)$_3$—), 0.26 (9H, s, —Si(CH$_3$)$_3$); $\delta_C$ (100 MHz, CDCl$_3$) 157.75 (C), 139.59 (C), 139.06 (C), 137.96 (C), 133.72 (C), 131.82 (2CH), 129.18 (2CH), 128.37 (2CH), 128.01 (2CH), 127.58 (CH), 127.53 (2CH), 127.50 (CH), 127.28 (2CH), 127.01 (CH), 126.83 (2CH), 113.76 (2CH), 103.38 (C), 97.76 (C), 67.71 (CH), 63.31 (CH), 55.23 (OCH$_3$), 46.42 (CH$_2$), 32.33 (CH$_2$), 31.63 (CH$_2$), -0.194 (Si(CH$_3$)$_3$); ESI-MS [M+H]$^+$ 597.2.

{N-((1R,2R)-2-(3-(4-Methoxyphenyl)propylamino)-1,2-diphenylethyl)-4-(2-(trimethylsilyl)ethynyl)benzenesulfonamide}-ruthenium chloride SRC 1139/1158

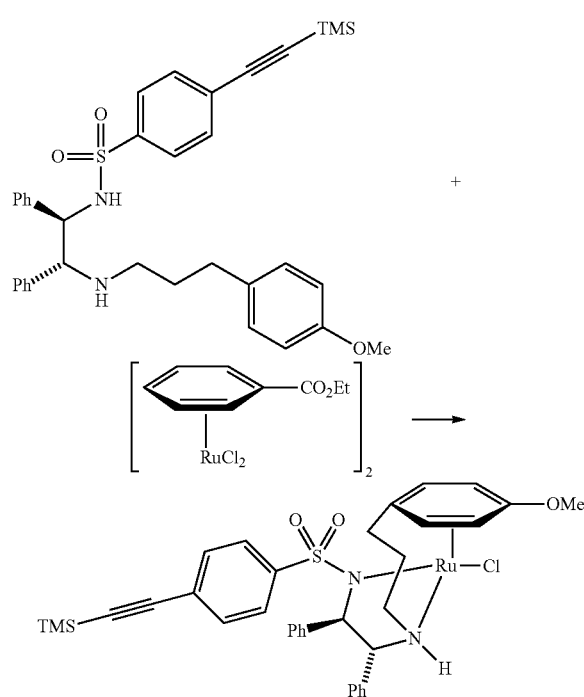

Diamine C$_{35}$H$_{40}$N$_2$O$_3$SSi (0.373 g, 0.626 mmol, 1.0 eq) and [RuCl$_2$(C$_9$H$_{10}$O$_2$)]$_2$ (0.202 g, 0.313 mmol, 0.5 eq) were dissolved in dry DCM (15 mL) under N$_2$ and stirred at room temp for 30 min to give a brick red solution. The mixture was concentrated on a rotavpor to give a dark orange residue. To this, chlorobenzene (30 mL) was added and mixture heated at 90° C. for 5.5 h. The reaction mixture was cooled to room temperature and concentrated to give a dark brown residue. The solid was scratched in diethyl ether, filtered and dried to give dark brown solid. The solid was purified by column chromatography over Florisil using DCM:MeOH (97:3 to 86:14) to give the crude compound as a brown solid. The solid was recrystallized from MeOH to give pure complex as orange solid (0.094 g, 0.128 mmol, 20%). Mp decomposition>280° C.; $[\alpha]_D^{28}$=-328.33 (c 0.03 in CHCl$_3$); $\nu_{max}$ 3190, 3051, 2936, 2917, 2156, 1533, 1465, 1454, 1257, 1181, 1041, 839, 814, 799, 760, 696 cm$^{-1}$; $\delta_H$ (400 MHz, CDCl$_3$) 7.31 (2H, d, J 8.2, —CH of —SO$_2$C$_6$H$_4$—), 7.165-7.07 (3H, m, —CH of phenyl), 7.03 (2H, d, J 8.4, —CH of —SO$_2$C$_6$H$_4$—), 6.83-6.79 (3H, m, —CH of phenyl), 6.68-6.64 (2H, m, —CH of phenyl), 6.55 (2H, d, J 7.6, —CH of phenyl), 5.55 (1H, d, J 5.6, —CH of Ru—Ar), 5.48 (1H, d, J 5.6, —CH of Ru—Ar), 5.32 (1H, d, J 6.0, —CH of Ru—Ar), 5.28 (1H, d, J 6.0, —CH of Ru—Ar), 4.30 (1H, d, J 11.2, —CHNTs), 4.06-3.99 (1H, m, —NH(CH$_2$)$_3$—), 3.96 (3H, s, —OCH$_3$), 3.62-3.56 (1H, m, —CHNH(CH$_2$)$_3$—), 2.81-2.75 (1H, m, —NH—CHHCH$_2$CH$_2$—), 2.52-2.42 (1H, m, —NH—CHHCH$_2$CH$_2$—), 2.24-2.48 (1H, m, —NH—CH$_2$CH$_2$CHH—), 2.34-2.26 (1H, m, —NH—CH$_2$CH$_2$CHH—), 2.13-1.95 (2H, m, —NH—CH$_2$CH$_2$CH$_2$—), 0.24 (9H, s, —Si(CH$_3$)$_3$); $\delta_C$ (100 MHz, CDCl$_3$) 146.67 (C), 138.45 (C), 136.21 (C), 134.65 (C), 130.72 (4CH), 128.72 (4CH), 128.41 (CH), 127.05 (2CH), 126.80 (2CH), 126.45 (CH), 123.15 (C), 104.97 (C), 96.68 (C), 91.18 (C), 84.62 (CH), 81.33 (CH), 78.79 (CH), 72.03 (CH), 68.84 (CH), 65.46 (CH), 56.80 (OCH$_3$), 49.43 (CH$_2$), 30.34 (CH$_2$), 27.27 (CH$_2$), -0.006 (Si(CH$_3$)$_3$); ESI-MS [M-Cl]$^+$ 697.1; HRMS found 697.1494 (C$_{35}$H$_{39}$N$_2$O$_3$RuSSi—Cl+ requires 697.1497, error=-0.1 ppm).

Ethoxyethoxy)ethoxy)ethoxy)benzenesulfonamide SRC 1215

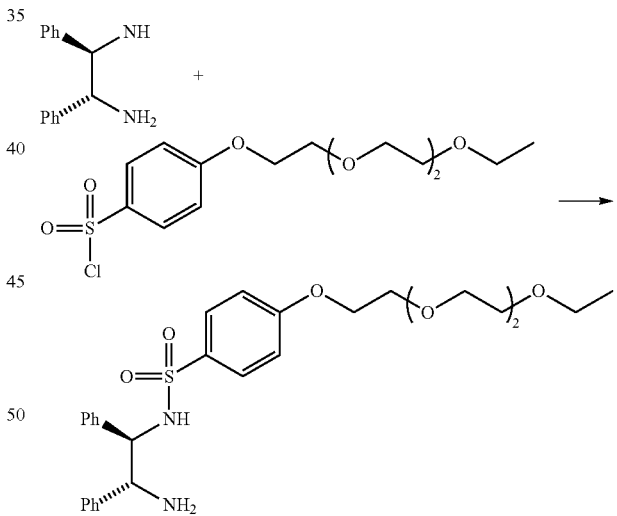

To a mixture of (R,R)-DPEN (0.637 g, 3.00 mmol) and TEA (0.760 mL, 5.460 mmol, 1.82 eq) in dry DCM (20 mL) was added a solution of chloride C$_{14}$H$_{21}$ClO$_6$S (1.056 g, 3.00 mmol, 1.0 eq) in dry DCM (10 mL) dropwise at 0° C. under an inert atmosphere. The resulting light pink solution was stirred at 0° C. for 30 min and at room temperature for 18 h. The mixture was concentrated on a rotavapor to give a crude compound. The crude compound was purified by column chromatography over silica gel using DCM:MeOH (95:5) as an eluent to give pure compound as an oil (1.380 g, 2.614 mmol, 87%). $[\alpha]_D^{28}$=-11.15 (c 0.740 in CHCl$_3$); $\nu_{max}$ 3280, 3062, 3030, 2972, 2868, 1594, 1580, 1495, 1453, 1323, 1301, 1255, 1179, 1094, 1054, 923, 832, 766, 698 cm$^{-1}$; $\delta_H$ (400 MHz, CDCl$_3$) 7.34 (2H, d, J 8.8, —CH of —SO$_2$C$_6$H$_4$—), 7.18-7.14 (6H, m, —CH of phenyl), 7.11-7.09 (4H, m, —CH of phenyl), 6.67 (2H, d, J 8.8, —CH of —SO$_2$C$_6$H$_4$—), 6.01 (1H, br s, —NHTs), 4.35 (1H, d, J 5.6, —CHNHTs), 4.11-4.08 (3H, m, —CHNH$_2$, —C$_6$H$_4$—OCH$_2$CH$_2$O—), 3.85 (2H, t, J 4.8, —C$_6$H$_4$—OCH$_2$CH$_2$O—), 3.75-3.72 (2H, m, —OCH$_2$CH$_2$O—CH$_2$CH$_2$OEt), 3.70-3.68 (2H, m, —OCH$_2$CH$_2$O—CH$_2$CH$_2$OEt), 3.67-3.64 (2H, m, —OCH$_2$CH$_2$O—CH$_2$CH$_2$OEt), 3.61-3.57 (2H, m, —OCH$_2$CH$_2$O—CH$_2$CH$_2$OEt), 3.52 (2H, q, J 7.1, —OCH$_2$CH$_3$), 1.51 (2H, br s, —NH$_2$), 1.20 (3H, t, J 7.1, —OCH$_2$CH$_3$); $\delta$c (100 MHz, CDCl$_3$) 161.49 (C), 141.46 (C), 139.18 (C), 131.93 (C), 128.86 (2CH), 128.41 (2CH), 128.21 (2CH), 127.51 (CH), 127.37 (CH), 127.01 (2CH), 126.51 (2CH), 114.25 (2CH), 70.88 (CH$_2$), 70.72 (CH$_2$), 70.63 (CH$_2$), 69.79 (CH$_2$), 69.41 (CH$_2$), 67.66 (CH$_2$), 66.61 (CH$_2$), 63.15 (CH), 60.52 (CH), 15.13 (CH$_3$); m/z ESI-MS [M+H]$^+$ 529.2; HRMS found 529.2354 (C$_{28}$H$_{36}$N$_2$O$_6$S H+ requires 529.2367, error=1.6 ppm).

4-(2-(2-(2-Ethoxyethoxy)ethoxy)ethoxy)-N-((1R, 2R)-2-(3-(4-methoxyphenyl)propylamino)-1,2-diphenylethyl)benzenesulfonamide SRC 1220

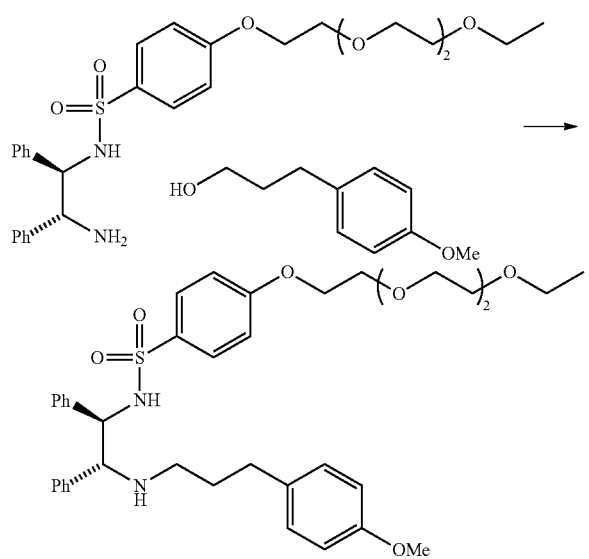

To a mixture of alcohol C$_{10}$H$_{14}$O$_2$ (0.266 g, 1.60 mmol, 1.6 eq) and 2,6-lutidine (0.245 mL, 2.10 mmol, 2.10 eq) in dry DCM (15 mL) was added a solution of triflic anhydride (1M in DCM) (1.7 mL, 1.70 mmol, 1.70 eq) dropwise at 0° C. under an inert atmosphere. The resulting light pink solution was stirred at 0° C. for 30 min and at room temperature for 60 min. The mixture was again cooled down to 0° C. To this, a solution of compound C$_{28}$H$_{36}$N$_2$O$_6$S (0.560 g, 1.0 mmol, 1.0 eq) and TEA (0.334 mL, 2.4 mmol, 2.4 eq) in dry DCM (10 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×20 mL). The organic layer was separated, washed with H$_2$O (2×20 mL), brine (15 mL), dried over anhy. Na$_2$SO$_4$, filtered and concentrated to give crude compound. The crude compound was purified by column chromatography over silica gel using EtOAc:Pet. ether (70:30) as an eluent to give a residue. The residue was triturated in n-pentane (to remove traces of 2,6-lutidine) but there was no any solid separation. The solvent was evaporated to give pure compound an oil (0.510 g, 0.754 mmol, 75%). [α]$_D^{28}$=−11.9 (c 0.470 in CHCl$_3$); $v_{max}$ 3262, 5062, 3029, 2864, 1594, 1580, 1511, 1495, 1453, 1300, 1244, 1149, 1093, 1030, 924, 830, 770, 698 cm$^{-1}$; $\delta_H$ (400 MHz, CDCl$_3$) 7.39 (2H, d, J 8.8, —CH of —SO$_2$C$_6$H$_4$—), 7.15-7.12 (3H, m, —CH of phenyl), 7.06-7.02 (3H, m, —CH of phenyl), 7.00 (2H, d, J 8.6, —CH of —C$_6$H$_4$OCH$_3$), 6.94-6.88 (4H, m, —CH of phenyl), 6.80 (2H, d, J 8.6, —CH of —C$_6$H$_4$OCH$_3$), 6.70 (2H, d, J 8.8, —CH of —SO$_2$C$_6$H$_4$—), 6.26 (1H, br s, —NHTs), 4.22 (1H, d, J 8.0, —CHNHTs), 4.11-4.08 (2H, m, —C$_6$H$_4$—OCH$_2$CH$_2$O—), 3.85 (2H, t, J 5.0, —C$_6$H$_4$—OCH$_2$CH$_2$O—), 3.78 (3H, s, —OCH$_3$), 3.74-3.72 (2H, m, —OCH$_2$CH$_2$O—CH$_2$CH$_2$OEt), 3.70-3.68 (2H, m, —OCH$_2$CH$_2$O—CH$_2$CH$_2$OEt), 3.67-3.64 (2H, m, —OCH$_2$CH$_2$O—CH$_2$CH$_2$OEt), 3.60-3.56 (3H, m, —CHNH(CH$_2$)$_3$—, —OCH$_2$CH$_2$O—CH$_2$CH$_2$OEt), 3.52 (2H, q, J 7.2, —OCH$_2$CH$_3$), 2.54-2.40 (3H, m, —NH—CHHCH$_2$CH$_2$—), 2.32-2.25 (1H, m, —NH—CHHCH$_2$CH$_2$—), 1.73-1.61 (2H, m, —NH—CH$_2$CH$_2$CH$_2$—), 1.45 (1H, br s, —NH(CH$_2$)$_3$—), 1.20 (3H, t, J 7.2, —OCH$_2$CH$_3$); $\delta$c (100 MHz, CDCl$_3$) 161.59 (C), 157.72 (C), 139.26 (C), 138.26 (C), 133.78 (C), 131.86 (C), 129.17 (2CH), 129.12 (2CH), 128.28 (2CH), 127.90 (2CH), 127.55 (2CH), 127.46 (CH), 127.35 (2CH), 127.28 (CH), 114.20 (2CH), 113.73 (2CH), 70.88 (CH$_2$), 70.71 (CH$_2$), 70.62 (CH$_2$), 69.79 (CH$_2$), 69.41 (CH$_2$), 67.73 (CH), 67.68 (CH$_2$), 66.61 (CH$_2$), 63.04 (CH), 55.22 (OCH$_3$), 46.42 (CH$_2$), 32.33 (CH$_2$), 31.68 (CH$_2$), 15.13 (CH$_3$); m/z ESI-MS [M+H]$^+$ 677.3; HRMS found 677.3254 (C$_{38}$H$_{48}$N$_2$O$_7$S H+ requires 677.3255, error=0.3 ppm).

{4-(2-(2-(2-Ethoxyethoxy)ethoxy)ethoxy)-N-((1R, 2R)-2-(3-(4-methoxyphenyl)propylamino)-1,2-diphenylethyl)benzenesulfonamide}-ruthenium chloride SRC 1221/1238/1303

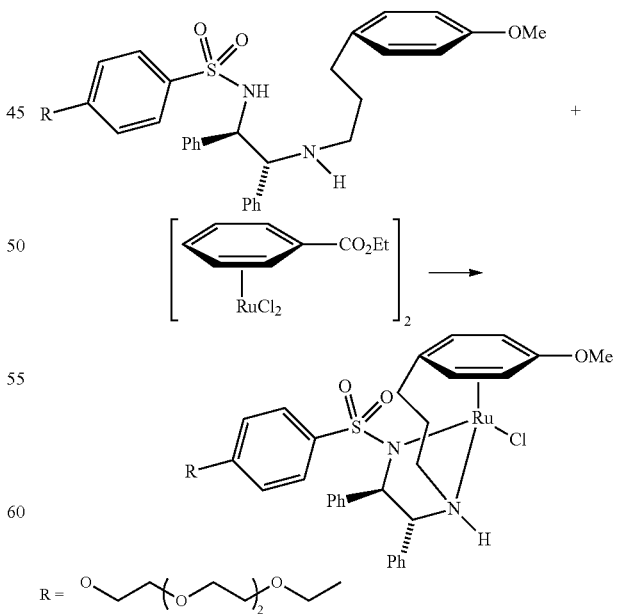

Compound C$_{38}$H$_{48}$N$_2$O$_7$S (0.203 g, 0.300 mmol, 1.0 eq) and [RuCl$_2$(C$_9$H$_{10}$O$_2$)]$_2$ (0.097 g, 0.150 mmol, 0.5 eq) were dissolved in dry DCM (15 mL) under $N_2$ and stirred at room temp for 30 min to give a brick red solution. The mixture was concentrated on a rotavapor to give dark orange residue. To this, chlorobenzene (20 mL) was added and mixture heated at 90° C. for 6 h. The reaction mixture was cooled to room temperature and concentrated to give a dark brown residue. The solid was scratched in diethyl ether, filtered and dried to give a dark brown solid. The solid was purified by column chromatography over Florisil using DCM:MeOH (97:3 to 86:14) to give the compound as a brown solid. The solid was recrystallized from MeOH to give pure complex as orange brown solid (0.075 g, 0.092 mmol, 30%). Mp decomposition>180° C.; $[\alpha]_D^{29}$=+646.7 (c 0.003 in $CHCl_3$); $\upsilon_{max}$ 3191, 3059, 3027, 2865, 1725, 1594, 1536, 1510, 1494, 1453, 1248, 1124, 1081, 1038, 1011, 938, 906, 815, 801.698 $cm^{-1}$; $\delta_H$ (400 MHz, $CDCl_3$) 7.31 (2H, d, J 8.6, —CH of —$SO_2C_6H_4$—), 7.17-7.06 (3H, m, —CH of phenyl), 6.85-6.74 (3H, m, —CH of phenyl), 6.68-6.64 (2H, m, —CH of phenyl), 6.55 (2H, d, J 7.2, —CH of phenyl), 6.46 (2H, d, J 8.6, —CH of —$SO_2C_6H_4$—), 5.55 (1H, d, J 4.2, —CH of Ru—Ar), 5.47 (1H, d, J 4.2, —CH of Ru—Ar), 5.34 (1H, d, J 5.4, —CH of Ru—Ar), 5.26 (1H, d, J 5.4, —CH of Ru—Ar), 4.30 (1H, d, J 10.8, —CHNTs), 4.06-3.94 (6H, m, —$C_6H_4$—$OCH_2CH_2O$—, —$OCH_3$, —$NH(CH_2)_3$—), 3.81 (2H, t, J 4.8, —$C_6H_4$—$OCH_2CH_2O$—), 3.72-3.65 (6H, m, —$OCH_2CH_2O$—$CH_2CH_2OEt$), 3.61-3.57 (2H, m, —$OCH_2CH_2O$—$CH_2CH_2OEt$, —$CHNH(CH_2)_3$—), 3.52 (2H, q, J 7.0, —$OCH_2CH_3$), 2.82-2.72 (1H, m, —NH—CHHCH$_2$CH$_2$—), 2.51-2.37 (2H, m, —NH—CHHCH$_2$CHH—), 2.33-2.27 (2H, m, —NH—CH$_2$CH$_2$CHH—), 2.17-1.96 (2H, m, —NH—CH$_2$CH$_2$CH$_2$—), 1.20 (3H, t, J 7.0, —$OCH_2CH_3$); $\delta_C$ (100 MHz, $CDCl_3$) 158.92 (C), 139.06 (C), 138.65 (C), 136.28 (C), 134.60 (C), 128.75 (2CH), 128.62 (6CH), 128.31 (CH), 126.92 (2CH), 126.16 (CH), 113.12 (2CH), 91.10 (C), 84.65 (CH), 81.49 (CH), 78.56 (CH), 72.15 (CH), 7.77 ($CH_2$), 70.66 ($CH_2$), 70.58 ($CH_2$), 69.76 ($CH_2$), 69.55 ($CH_2$), 68.91 (CH), 67.40 ($CH_2$), 66.59 ($CH_2$), 65.52 (CH), 56.76 ($OCH_3$), 49.36 ($CH_2$), 30.22 ($CH_2$), 27.30 ($CH_2$), 15.12 ($CH_3$); m/z ESI-MS $[M-Cl]^+$ 777.1; HRMS found 777.2163 ($C_{38}H_{47}N_2O_7RuS$—Cl+ requires 777.2151, error=–2.0 ppm).

(1R,2R)-N,N-Bis(3-(4-methoxyphenyl)propyl)-1,2-diphenylethane-1,2-diamine

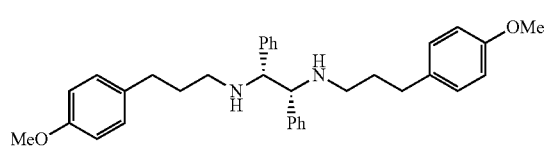 [SMILES: COc1ccc(CCCN[C@H](c2ccccc2)[C@H](NCCCc2ccc(OC)cc2)c2ccccc2)cc1]

To a nitrogen purged, dried flask was added 3-(4-methoxyphenyl)propan-1-ol (416 mg, 2.50 mmol) was added 2,6-lutidine (321 mg, 3.00 mmol) and anhydrous DCM (5 $cm^3$). The solution was cooled to 0° C. and to it as added a solution of $Tf_2O$ (759 mg, 2.70 mmol) in anhydrous DCM (1 $cm^3$). The reaction was stirred at 0° C. for 30 min and then at room temperature for 60 min. After this the reaction was again cooled to 0° C. and to it was added a solution of (R,R)-DPEN (212 mg, 1.00 mmol) and $Et_3N$ (354 mg, 3.5 mmol) in anhydrous DCM (1 $cm^3$). The reaction was stirred at 0° C. for 30 min and then at room temperature overnight. After this DCM was added and the reaction washed with saturated $NaHCO_3$ solution (aq). (3×10 $cm^3$). The organic phase was dried over $Na_2SO_4$, filtered and the solvent removed under reduced pressure to leave the crude as a yellow oil. The crude product was purified by column chromatography (silica gel, 0-50% EtOAc in petroleum ether, TLC: silica gel, 30% EtOAc in petroleum ether, product Rf=0.18 visualisation by UV and $KMnO_4$, 2,6-lutidine Rf=0.38 visualisation by UV, 2,6-lutidine elutes before product) to give the product as a white solid (326 mg, 0.64 mmol, 64% based on (R,R)-DPEN). $[\alpha]_D^{26}$+ 4.4 (c 0.5 in $CHCl_3$) (R,R); (found (ESI): $M^+$+H, 509.3164 $C_{34}H_{41}N_2O_2$ requires M, 509.3163); $\upsilon_{max}$ 2931, 2834, 1510, 1452, 1243, 1035, 830, 810, 731, 698, $cm^{-1}$; $\delta_H$ (300 MHz, $CDCl_3$) 7.17-7.12 (6H, m, CHAr), 7.07-7.02 (8H, m, CHAr), 3.77 (6H, s, $CH_3$), 3.63 (2H, s, CHN), 2.57-2.36 (8H, m, ArCH$_2$ and CH$_2$NH overlapping), 1.79-1.69 (4H, m, $CH_2CH_2CH_2N$); $\delta_C$ (75 MHz, $CDCl_3$) 157.06 (2 CAr), 141.00 (2 CAr), 133.76 (2 CAr), 128.67 (4 CHAr), 127.32 (4 CHAr), 127.28 (4 CHAr), 126.22 (2 CHAr), 113.09 (4 CHAr), 68.66 (2 CH), 54.65 (2 $CH_3$), 46.45 (2 $CH_2$), 31.97 (2 $CH_2$), 31.44 (2 $CH_2$); m/z (ESI) 509.3 ($M^+$+1).

Cationic Tethered Ruthenium Complex ('Cationic Complex')

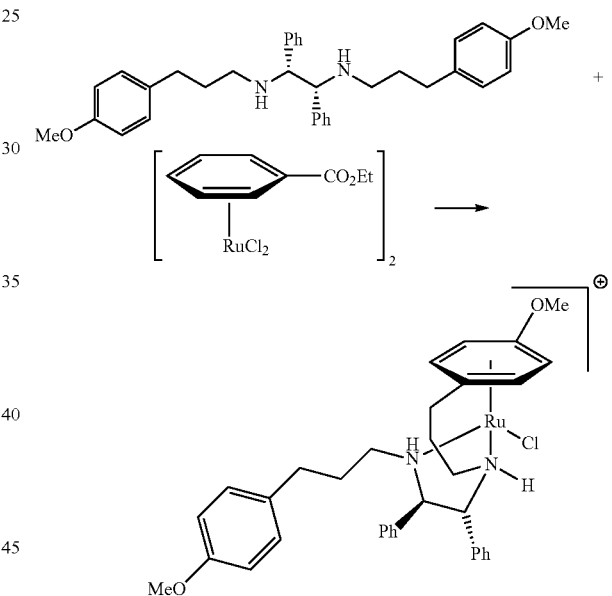

This compound was prepared according to the general method using (1R,2R)-N,N-Bis(3-(4-methoxyphenyl)propyl)-1,2-diphenylethane-1,2-diamine (200 mg, 0.40 mmol), ethylbenzoate ruthenium(II)chloride dimer (129 mg, 0.20 mmol), DCM (10.3 $cm^3$) and chlorobenzene (26.7 $cm^3$). It was only necessary to stir the reaction in chlorobenzene at 90° C. for 1 hour before complete consumption of the ligand was observed by TLC. The crude product was purified by column chromatography (silica gel, 0-30% MeOH in DCM, TLC: silica plate, 5% MeOH in DCM, visualisation in natural light, product Rf=0.48 yellow) to give the product as a yellow/orange solid (158 mg, 0.24 mmol, 60%). Mp 85° C.; $[\alpha]_D^{28}$+ 210 (c 0.01 in $CHCl_3$) (R,R); (found (ESI): $M^+$, 645.1820. $C_{34}H_{40}ClN_2O_2Ru$ requires M, 645.1822); $\upsilon_{max}$ 3059, 2928, 1511, 1454, 1244, 1177, 1029, 1005, 805, 763, 701 $cm^{-1}$; $\delta_H$ (400 MHz, $CDCl_3$) 8.72 (1H, br s, NH), 7.96 (1H, br s, NH), 7.12-7.06 (6H, m, CHAr), 6.86-6.81 (4H, m, CHAr), 6.75-6.68 (4H, m, CHAr), 5.69-5.67 (1H, m, CHAr—Ru), 5.45-5.43 (1H, m, CHAr—Ru), 5.18-5.16 (1H, m, CHAr—Ru), 5.10-5.09 (1H, m, CHAr—Ru), 4.39 (1H, br s, CHNH), 3.95-3.86 (1H, m, CHNH), 3.60 (3H, s, CH$_3$OAr—Ru), 3.05-3.02 (2H, m, CH$_2$), 2.87 (2H, br s, CH$_2$), 2.33-2.30 (4H, m, CH$_2$), 2.17 (3H, s, CH$_3$OAr(CH$_2$)$_3$N), 1.91 (1H, br s, CH$_2$), 1.72-1.59 (3H, m, CH$_2$); δ$_C$ (100 MHz, CDCl$_3$) 157.67 (CAr), 137.78 (CAr), 136.34 (CAr), 135.04 (CAr), 134.73 (CAr), 132.78 (CAr), 129.07 (2 CHAr), 129.00 (2 CHAr), 128.93 (2 CHAr), 128.76 (CHAr), 128.56 (2 CHAr), 128.26 (2 CHAr), 127.52 (CHAr), 113.65 (2 CHAr), 100.47 (CAr—Ru), 86.98 (CAr—Ru), 86.75 (CHAr—Ru), 75.53 (CHAr—Ru), 71.31 (CHAr—Ru), 70.10 (CHAr—Ru), 66.97 (CH), 56.69 (CH), 55.24 (CH$_3$), 53.38 (CH$_2$), 32.31 (CH$_2$), 31.82 (CH$_2$), 30.12 (CH$_2$), 30.09 (CH$_3$), 29.14 (CH$_2$), 27.74 (1C, s); m/z (ESI) 645.2 (M$^+$). Asymmetric reduction with this complex gave no reduction in FA/TEA, or pressure hydrogenation however it was active using sodium formate in aqueous solution (Table 3).

N-(2-(Biphenyl-2-yl)methylamino)ethyl)-4-methyl-benzenesulphonamide

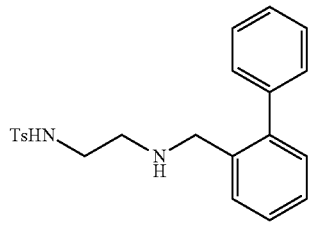

To biphenylcarboxaldehyde (182 mg, 1.00 mmol) was added activated molecular sieves (1 g) and anhydrous MeOH (6 cm$^3$). To this was added TsEN (246 mg, 1.10 mmol) and acetic acid (50 μL). The reaction was stirred at room temperature for 5 hours and then NaBH$_3$CN (251 mg, 4.00 mmol) was added and the reaction stirred at room temperature overnight. After this the reaction was filtered and the solid washed with DCM. The filtrate and DCM washings were combined and dried under reduced pressure. The residue was then dissolved in anhydrous DCM and washed with 1M NaOH (aq) solution. The DCM phase was separated, dried over Na$_2$SO$_4$, filtered and the solvent removed under reduced pressure to give the product as a pale yellow viscous oil (134 mg, 0.35 mmol, 70%). Purification was not necessary. (found (ESI): M$^+$+H, 381.1632 C$_{22}$H$_{25}$N$_2$O$_2$S requires M, 381.1631); υ$_{max}$ 3272, 2858, 1477, 1450, 1322, 1155, 1091, 814, 775, 750, 703 cm$^{-1}$; δ$_H$ (300 MHz, CDCl$_3$) 7.67 (2H, d J, 8.1 Hz, SO$_2$CHAr), 7.43-7.11 (13H, m, CHAr and NH overlapping), 3.58 (2H, s, ArCH$_2$N), 2.84 (2H, dd J, 6.5 and 4.8 Hz, CH$_2$NHSO$_2$), 2.50 (2H, dd J, 6.5 and 4.8 Hz, CH$_2$NH), 2.40 (3H, s, CH$_3$); δ$_C$ (75 MHz, CDCl$_3$) 142.64 (CAr), 141.24 (CAr), 140.53 (CAr), 136.39 (CAr), 136.22 (CAr), 129.57 (CHAr), 129.04 (2 CHAr), 128.50 (CHAr), 128.27 (2 CHAr), 127.68 (2 CHAr), 126.95 (CHAr), 126.62 (CHAr), 126.55 (CHAr), 126.49 (2 CHAr), 50.06 (CH$_2$), 46.65 (CH$_2$), 41.60 (CH$_2$), 20.92 (CH$_3$); m/z (ESI) 381.0 (M$^+$+1).

{N-(1R,2R)-[2-(biphenyl-2-yl)methylamino]ethyl-4-methylbenzenesulfonamide}ruthenium chloride SRC 1301 a (2) ('Achiral Bn' Complex)

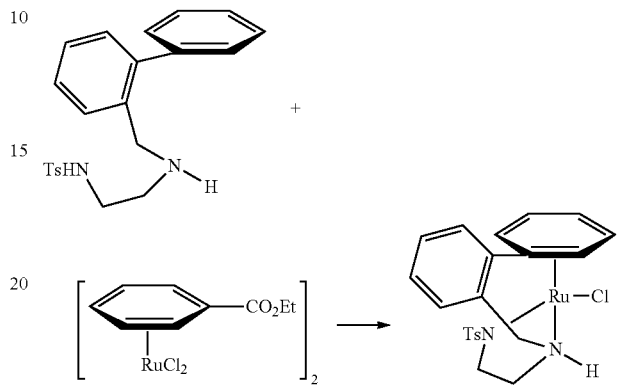

Diamine C$_{22}$H$_{24}$N$_2$O$_2$S (0.450 g, 1.184 mmol, 1.0 eq) and [RuCl$_2$(C$_9$H$_{10}$O$_2$)]$_2$ (0.381 g, 0.592 mmol, 0.5 eq) were dissolved in dry DCM (40 mL) under N$_2$ and stirred at room temp for 30 min to give a brick red solution. The mixture was concentrated on a rotavpor to give a dark orange residue. To this, chlorobenzene (60 mL) was added and mixture heated at 140° C. for 5.5 h. The reaction mixture was cooled to room temperature and concentrated to give a dark brown residue. The solid was scratched in diethyl ether, filtered and dried to give a dark brown solid. The solid was purified by column chromatography over Florisil using DCM:MeOH (95:5 to 86:14) to give compound as a brown solid. The solid was recrystallized using a mixture of MeOH and Et$_2$O to give pure complex as brown solid (0.105 g, 0.203 mmol, 14%). Mp decomposition>184° C.; ν$_{max}$ 3059, 2922, 2855, 1596, 1480, 1439, 1260, 1182, 1129, 811, 747, 704, 659 cm$^{-1}$; δ$_H$ (600 MHz, CDCl$_3$) 7.74 (2H, d, J 6.9, m-CH of —SO$_2$C$_6$H$_4$CH$_3$), 7.52-7.40 (4H, m, —CH of phenyl), 7.16 (2H, d, J 6.9, o-CH of —SO$_2$C$_6$H$_4$CH$_3$), 6.67 (1H, br s, —CH of Ru—Ar), 5.81 (1H, br s, —CH of Ru—Ar), 5.68 (1H, br s, —CH of Ru—Ar), 5.28 (1H, br s, —CH of Ru—Ar), 5.25 (1H, br s, —CH of Ru—Ar), 4.78 (1H, br d, —CH$_2$—NH—CHH—C$_6$H$_4$—), 4.49 (1H, br s, —CHNH—CH$_2$—), 4.28 (1H, br d, —CH$_2$—NH—CHH—C$_6$H$_4$—), 3.07 (1H, br d, —NHTs-CHH—), 2.59 (1H, br s, —CHH—NH—CH$_2$—C$_6$H$_4$—), 2.33 (4H, br s, —NHTs-CHH—, —CH$_3$), 2.14 (1H, br s, —CHH—NH—CH$_2$—C$_6$H$_4$—); δc (150 MHz, CDCl$_3$) 140.49 (C), 140.40 (C), 134.69 (C), 132.36 (C), 131.24 (CH), 129.81 (CH), 129.74 (CH), 129.37 (CH), 128.66 (2CH), 127.13 (2CH), 93.04 (C), 92.28 (CH), 90.62 (CH), 81.27 (CH), 78.90 (CH), 77.47 (CH), 57.75 (CH$_2$), 55.43 (CH$_2$), 48.25 (CH$_2$), 21.31 (CH$_3$); m/z ESI-MS [M-Cl]$^+$ 480.9; HRMS found 481.0524 (C$_{22}$H$_{23}$N$_2$O$_2$SRu—Cl+ requires 481.0523, error=–0.7 ppm).

Asymmetric Hydrogenation Procedures:
ATH in Water:
Catalyst (0.01 mmol) was placed in a Schlenk tube under an inert atmosphere followed by HCOONa (0.340 g, 5.0 mmol) and H$_2$O (1 mL). The mixture was degassed three times and to this solution ketone (1 mmol) was added followed by degassing 2 times. The mixture was stirred at 60° C. The reaction was monitored by chiral GC. For chiral GC analysis, the sample from the reaction mixture was diluted with Et$_2$O and H$_2$O. The organic layer was separated, filtered through a short column of silica using hexane:EtOAc (1:1). The filtrate was analysed by chiral GC. After completion of the reaction, the reaction mixture was diluted with H$_2$O and extracted with Et$_2$O (2×5 mL). The organic layers were combined, dried over anhy. Na$_2$SO$_4$, filtered and concentrated to give crude compound. The crude compound was purified by flash column chromatography to give pure product.

Recycling of Catalyst Using Hexane/Pet.Ether/n-Pentane:

Catalyst (0.01 mmol) was placed in a Schlenk tube under an inert atmosphere followed by HCOONa (0.340 g, 5.0 mmol) and H$_2$O (1 mL). The mixture was degassed three times and to this ketone (1 mmol) was added followed by degassing 2 times. The mixture was stirred at 60° C. The reaction was monitored by chiral GC. For chiral GC analysis, the sample from the reaction mixture was diluted with Et$_2$O and H$_2$O. The organic layer was separated and filtered through a short column of silica using hexane:EtOAc (1:1). The filtrate was analysed by chiral GC. After completion of the reaction, the reaction mixture was cooled to room temperature and diluted with hexane/pet.ether/n-pentane (2 mL). The organic layers were separated and this process was repeated again two times with hexane/pet.ether/n-pentane (2 mL). During this process, the catalyst separated out as brown solid. The mixture was degassed two times followed by addition of HCOOH (1 mmol). To this mixture ketone (1 mmol) was added and stirred at 60° C. and the second cycle of the reaction was followed by chiral GC analysis.

Asymmetric Transfer Hydrogenation in FA:

TEA: To a mixture of catalyst (0.002 mmol) in FA:TEA (5:2) (1.0 mL) was added ketone (2.0 mmol) and the mixture was stirred at 60° C. for 24 h under an inert atmosphere. The reaction was monitored by TLC. After 24 h, the reaction mixture was diluted with EtOAc and sat. NaHCO$_3$ soln. The organic layer was separated, washed with H$_2$O, dried over anhy. Na$_2$SO$_4$, filtered and concentrated to give a brown residue. The crude compound was analysed by $^1$H-NMR to give the conversion.

Data for the Reduction Products (R)-1-Phenylethanol SRC 1237

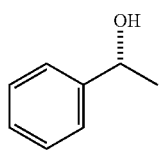

$\delta_H$ (300 MHz, CDCl$_3$) 7.38-7.24 (5H, m, Ph), 4.87 (1H, q, J 6.5, —CH), 2.07 (1H, br s, —OH), 1.48 (3H, d, J 6.5, —CH$_3$); $\delta_C$ (75 MHz, CDCl$_3$): 145.20, 127.90 (2C), 126.87, 124.78 (2C), 69.81, 24.55; the enantiomeric excess and conversion determined by GC analysis (CP-Chirasil-DEX CB 25 m×0.25 mm×0.25 μm, T=110° C., P=18 psi, He gas) Ketone 6.56 min, R isomer 14.61 min, S isomer 16.50 min; $[\alpha]_D^{28}$=+58.1 (c 0.730 in CHCl$_3$) for 97% ee [lit. value $[\alpha]_D^{27}$=+54.9 (c 1.0 in CHCl$_3$) 96% ee (R)]$^x$.

J. Hannedouche, G. Clarkson and M. Wills, *J. Am. Chem. Soc.*, 2004, 126, 986-987.

(S)-1-Cyclohexylethanol SRC 1194/1196

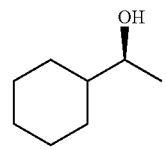

$\delta_H$ (300 MHz, CDCl$_3$) 3.58-3.50 (1H, m, CHOH), 1.87-1.65 (5H, m, cyclohexyl), 1.50 (1H, br s, —OH), 1.33-1.18 (4H, m, cyclohexyl), 1.15 (3H, d, J 6.3, —CH$_3$), 1.10-0.89 (2H, m, cyclohexyl); $\delta_C$ (75 MHz, CDCl$_3$): 72.22 (CH), 45.08, 28.67, 28.32, 26.48, 26.19, 26.0, 20.35 (CH$_3$); the enantiomeric excess determined by GC analysis of acetate derivative (CP-Chirasil-DEX CB 25 m×0.25 mm×0.25 μm, T=100° C., P=18 psi, He gas) S isomer 13.80 min, R isomer 18.64 min; $[\alpha]_D^{26}$=+3.03 (c 0.560 in CHCl$_3$) for 85% ee [lit. value $[\alpha]_D^{22}$=+2.7 (c 0.5 in CHCl$_3$) 75% ee (R)]$^x$.

G. Li and G. W. Kabalka, *Journal of Organometallic Chemistry*, 1999, 581 (1-2), 66-69.

(R)-1-Phenyl-1-propanol SRC 1240

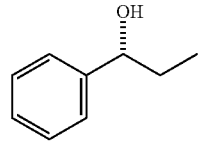

$\delta_H$ (400 MHz, CDCl$_3$) 7.36-7.25 (5H, m, Ph), 4.58 (1H, t, J 6.4, —CH), 2.03 (1H, br s, —OH), 1.87-1.68 (2H, m, —CH$_2$), 1.48 (3H, d, J 7.4, —CH$_3$); $\delta_C$ (100 MHz, CDCl$_3$): 144.55, 128.36 (2C), 127.46, 125.94 (2C), 75.99, 31.84, 10.11; the enantiomeric excess and conversion determined by GC analysis (CP-Chirasil-DEX CB 25 m×0.25 mm×0.25 μm, T=115° C., P=18 psi, He gas) Ketone 8.48 min, R isomer 19.39 min, S isomer 21.00 min; $[\alpha]_D^{29}$=+53.6 (c 0.750 in CHCl$_3$) for 98% ee (R) [lit. value $[\alpha]_D^{25}$=-47.2 (c 0.65 in CHCl$_3$) 99% ee (S)]$^x$.

Nakamura, K; Matsuda, T. *J. Org. Chem.* 1998, 63, 8957-8964.

(R)-1-Tetralol SRC 1241

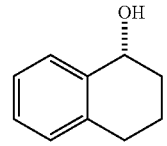

$\delta_H$ (400 MHz, CDCl$_3$) 7.47-7.37 (1H, m, —CH of Ph), 7.22-7.05 (3H, m, —CH of Ph), 4.78 (1H, br s, —CH), 2.89-2.65 (2H, m, —CH$_2$), 2.03-1.74 (5H, m, —CHOH—CH$_2$—CH$_2$); $\delta_C$ (100 MHz, CDCl$_3$): 138.77, 137.09, 128.99, 128.62, 127.56, 126.16, 68.14, 32.24, 29.21, 18.75; the enantiomeric excess and conversion determined by GC analysis (CP-Chirasil-DEX CB 25 m×0.25 mm×0.25 μm, T=120° C., P=18 psi, He gas) Ketone 24.70 min, S isomer 44.00 min, R isomer 45.12 min; $[\alpha]_D^{28}=-30.5$ (c 1.000 in CHCl$_3$) for 97% ee (R) [lit. value $[\alpha]_D=+34.4$ (c 1.01 in CHCl$_3$) 98% ee (S)]$^x$.

Palmer, M.; Walsgrove, T.; Wills, M. *J. Org. Chem.* 1997, 62, 5226-5228

(R)-1-(4-Chlorophenyl)ethanol SRC 1243

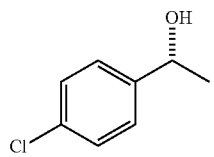

$\delta_H$ (400 MHz, CDCl$_3$) 7.30 (4H, br s, —CH of Ph), 4.86 (1H, t, J 6.4, —CH), 2.00 (1H, br s, —OH), 1.48 (3H, d, J 6.4, —CH$_3$); $\delta_C$ (100 MHz, CDCl$_3$): 144.19, 133.00, 128.55 (2C), 126.75 (2C), 89.69, 25.23; the enantiomeric excess and conversion determined by GC analysis (CP-Chirasil-DEX CB 25 m×0.25 mm×0.25 μm, T=150° C., P=18 psi, He gas) Ketone 4.48 min, R isomer 7.75 min, S isomer 8.56 min; $[\alpha]_D^{26}=+45.0$ (c 0.840 in CHCl$_3$) for 95% ee (R) [lit. value $[\alpha]_D=+38.6$ (c 1.01 in CHCl$_3$) 88% ee (R)]$^x$.

M. Locatelli, P. G. Cozzi. *Angew. Chem. Int. Ed*, 2003, 42, 4928-4930.

(R)-1-(4-Methoxyphenyl)ethanol SRC 1242

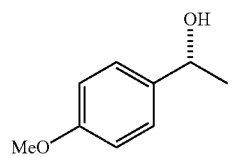

$\delta_H$ (300 MHz, CDCl$_3$) 7.30 (2H, d, J 8.7, —CH of Ph), 6.88 (2H, d, J 8.7, —CH of Ph), 4.85 (1H, t, J 6.4, —CH), 3.80 (3H, s, —OCH$_3$), 1.88 (1H, br s, —OH), 1.48 (3H, d, J 6.4, —CH$_3$); $\delta_C$ (75 MHz, CDCl$_3$): 158.92, 137.94, 126.63 (2C), 113.79 (2C), 69.96, 55.25, 24.98; the enantiomeric excess and conversion determined by GC analysis (CP-Chirasil-DEX CB 25 m×0.25 mm×0.25 μm, T=115° C., P=18 psi, He gas) Ketone 13.20 min, R isomer 18.04 min, S isomer 19.81 min; $[\alpha]_D^{262}=+47.4$ (c 0.610 in CHCl$_3$) for 97% ee (R) [lit. value $[\alpha]_D^{27}=+32.3$ (c 1.0 in CHCl$_3$) 90% ee (R)]$^x$.

J. Hannedouche, G. Clarkson, M. Wills, *J. Am. Chem. Soc.* 2004, 126, 986-987.

(R)-1-(3-Methoxyphenyl)ethanol SRC 1245

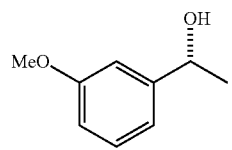

$\delta_H$ (300 MHz, CDCl$_3$) 7.26 (1H, t, J 8.1, —CH of Ph), 6.95-6.93 (2H, m, —CH of Ph), 6.81 (1H, ddd J 8.1, 2.4, 0.9, —CH of Ph), 4.86 (1H, t, J 6.3, —CH), 3.81 (3H, s, —OCH$_3$), 1.94 (1H, br s, —OH), 1.48 (3H, d, J 6.3, —CH$_3$); $\delta_C$ (75 MHz, CDCl$_3$): 159.72, 147.56, 129.50, 117.63, 112.84, 110.83, 70.30, 55.19, 25.11; the enantiomeric excess and conversion determined by GC analysis (CP-Chirasil-DEX CB 25 m×0.25 mm×0.25 μm, T=140° C., P=18 psi, He gas) Ketone 6.45 min, R isomer 11.75 min, S isomer 12.69 min; $[\alpha]_D^{28}=+38.06$ (c 0.670 in CHCl$_3$) for 97% ee (R) [lit. value $[\alpha]_D^{23}=+31.8$ (c 2.0 in CHCl$_3$) 94% ee (R)]$^x$.

F. Wang, H. Liu, L. Cun, J. Zhu, J. Deng, Y. Jiang. *J. Org. Chem.* 2005, 70, 9424-9429.

(R)-1-(2-Methoxyphenyl)ethanol SRC 1246

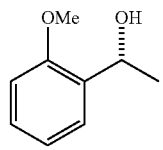

$\delta_H$ (400 MHz, CDCl$_3$) 7.34 (1H, dd, J 7.2, 1.2, —CH of Ph), 7.26-7.22 (1H, m, —CH of Ph), 6.96 (1H, t, J 7.4, —CH of Ph), 6.88 (1H, br d, J 8.0, —CH of Ph), 5.09 (1H, t, J 6.4, —CH), 3.85 (3H, s, —OCH$_3$), 2.72 (1H, br s, —OH), 1.50 (3H, d, J 6.4, —CH$_3$); $\delta_C$ (100 MHz, CDCl$_3$): 156.52, 133.37, 128.26, 126.06, 120.76, 110.40, 66.51, 55.22, 22.80; the enantiomeric excess and conversion determined by GC analysis (CP-Chirasil-DEX CB 25 m×0.25 mm×0.25 μm, T=150° C., P=18 psi, He gas) Ketone 4.66 min, S isomer 6.59 min, R isomer 6.89 min; $[\alpha]_D^{28}=+26.5$ (c 1.200 in CHCl$_3$) for 96% ee (R) [lit. value $[\alpha]_D^{20}=+32.3$ (c 2.0 in CHCl$_3$) 94% ee (R)]$^x$.

T. S. Kaufman, *Tetrahedron Lett.* 1996, 37, 5329-5332.

(R)-1-(1-Naphthyl)ethanol SRC 1247

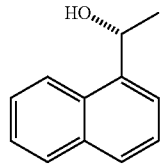

$\delta_H$ (400 MHz, CDCl$_3$) 8.10 (1H, d, J 8.4, —CH of naphthyl), 7.86 (1H, dd, J 7.2, 2, —CH of naphthyl), 7.76 (1H, d, J 8.4, —CH of naphthyl), 7.76 (1H, d, J 7.2, —CH of naphthyl), 7.53-7.44 (3H, m, —CH of naphthyl), 5.65 (1H, q, J 6.4, —CH), 2.08 (1H, br s, —OH), 1.65 (3H, d, J 6.4, —CH$_3$); $\delta_C$ (100 MHz, CDCl$_3$): 141.30, 133.77, 130.24, 128.86, 127.90, 126.00, 125.51, 125.49, 123.12, 121.95, 67.09, 24.30; the enantiomeric excess and conversion determined by GC analysis (CP-Chirasil-DEX CB 25 m×0.25 mm×0.25 μm, T=160° C., P=18 psi, He gas) Ketone 10.37 min, S isomer 21.01 min, R isomer 22.40 min; $[\alpha]_D^{32}=+60.3$ (c 0.910 in CHCl$_3$) for 99% ee (R) [lit. value $[\alpha]_D=+67.3$ (c 0.4 in CHCl$_3$) 100% ee (R)]$^x$.

H. Ziffer, K. Kawai, M. Kasai, M. Imuta, C. Froussios. J. Org. Chem. 1983, 48, 3017-3021.

(R)-1-(2-Naphthyl)ethanol SRC 1248

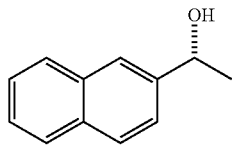

$\delta_H$ (400 MHz, CDCl$_3$) 7.87-7.73 (4H, m, —CH of naphthyl), 7.54-7.40 (3H, m, —CH of naphthyl), 5.04 (1H, t, J 6.4, —CH), 1.98 (1H, br s, —OH), 1.48 (3H, d, J 6.4, —CH$_3$); $\delta_C$ (100 MHz, CDCl$_3$): 143.15, 133.29, 132.89, 128.28, 127.90, 127.64, 126.11, 125.76, 123.78 (2C), 70.49, 25.10; the enantiomeric excess and conversion determined by GC analysis (CP-Chirasil-DEX CB 25 m×0.25 mm×0.25 μm, T=150° C., P=18 psi, He gas) Ketone 18.92 min, R isomer 30.87 min, S isomer 33.38 min; $[\alpha]_D^{28}$=+46.4 (c 0.850 in CHCl$_3$) for 97% ee (R) [lit. value $[\alpha]_D^{23}$=+46.7 (c 1.02 in CHCl$_3$) 92% ee (R)]$^x$.

Y. Ma, H. Liu, L. Chen, X, Cui, J. Zhu, J. Deng. Org. Lett. 2003, 5, 2103-2106.

(S)-1-Phenyl-2-chloroethanol SRC 1249

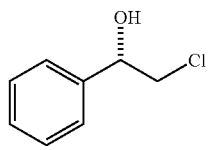

$\delta_H$ (400 MHz, CDCl$_3$) 7.39-7.31 (5H, m, Ph), 4.89 (1H, m, —CHOH), 3.74 (1H, dd, J 11.4, 3.6, —CHHCl), 3.64 (1H, dd, J 11.4, 8.6, —CHHCl), 2.69 (1H, d, J 3.2, —OH); $\delta_C$ (100 MHz, CDCl$_3$): 139.86, 128.65 (2C), 128.43, 126.02 (2C), 74.03, 50.88; the enantiomeric excess and conversion determined by GC analysis (CP-Chirasil-DEX CB 25 m×0.25 mm×0.25 μm, T=150° C., P=18 psi, He gas) Ketone 6.96 min, R isomer 9.00 min, S isomer 9.60 min; $[\alpha]_D^{32}$=+61.8 (c 0.810 in CHCl$_3$) for 95% ee (S) [lit. value $[\alpha]_D^{22}$=+53.8 (c 1.0 in CHCl$_3$) >99% ee (S)]$^x$.

D. Zhu, C. Mukherjee, L. Hua. Tetrahedron: *Asymmetry,* 2005, 16, 3275-3278.

(R)-1-(4-Trifluoromethylphenyl)ethanol SRC 1250

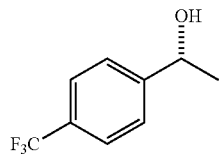

$\delta_H$ (300 MHz, CDCl$_3$) 7.60 (2H, d, J 8.0, —CH of Ph), 7.48 (2H, d, J 7.9, —CH of Ph), 4.95 (1H, t, J 6.4, —CH), 2.11 (1H, br s, —OH), 1.49 (3H, d, J 6.4, —CH$_3$); $\delta_C$ (75 MHz, CDCl$_3$): 149.65, 125.93, 125.62 (2C), 125.41 (2C, q, $^3J_{C-F}$ 4.3 Hz), 122.33, 69.80, 25.36; the enantiomeric excess and conversion determined by GC analysis (CP-Chirasil-DEX CB 25 m×0.25 mm×0.25 μm, T=120° C., P=18 psi, He gas) Ketone 5.02 min, R isomer 13.92 min, S isomer 17.19 min; $[\alpha]_D^{29}$=+32.5 (c 0.690 in CHCl$_3$) for 94% ee (R) [lit. value $[\alpha]_D^{22}$=+29.3 (c 1.0 in CHCl$_3$) >99% ee (R)]$^x$.

D. Zhu, Y. Yang, L. Hua, *J. Org. Chem.* 2006, 71, 4202-4205.

(R)-1-(2-Trifluoromethylphenyl)ethanol SRC 1251

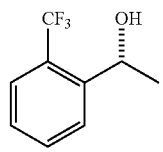

$\delta_H$ (300 MHz, CDCl$_3$) 7.82 (1H, br d, J 7.8, —CH of Ph), 7.61-7.56 (2H, m, —CH of Ph), 7.36 (1H, t, J 7.5, —CH of Ph), 5.37-5.29 (1H, m, —CH), 2.03 (1H, br d, —OH), 1.48 (3H, d, J 6.6, —CH$_3$); $\delta_C$ (75 MHz, CDCl$_3$): 144.99, 132.36, 127.32, 127.06, 126.15, 125.27 (q, $^3J_{C-F}$ 6.1 Hz), 122.52, 65.64, 25.40; the enantiomeric excess and conversion determined by GC analysis (CP-Chirasil-DEX CB 25 m×0.25 mm×0.25 μm, T=110° C., P=18 psi, He gas) Ketone 5.30 min, R isomer 16.74 min, S isomer 19.44 min; $[\alpha]_D^{25}$=+34.78 (c 1.11 in CHCl3) for 69% ee (R) [lit. value $[\alpha]_D^{22}$=−45.4 (c 0.661 in MeOH) 97% ee (S)]$^x$.

Nakamura, K.; Matsuda, T. *J. Org. Chem.* 1998, 63, 8957.

(R)-1-(4-Aminophenyl)ethanol SRC 1254/1256/1261

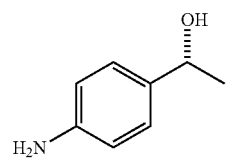

$\delta_H$ (300 MHz, CDCl$_3$) 7.16 (2H, d, J 8.6, —CH of Ph), 6.66 (2H, d, J 8.6, —CH of Ph), 4.78 (1H, t, J 6.4, —CH), 3.61 (2H, br s, —NH$_2$), 1.80 (1H, br s, —OH), 1.45 (3H, d, J 6.4, —CH$_3$); $\delta_C$ (75 MHz, CDCl$_3$): 145.75, 135.89, 126.61 (2C), 115.03 (2C), 70.08, 24.75; the enantiomeric excess determined by chiral HPLC analysis (ChiralPak OD-H Column: 0.46 cm×25 cm, hexane:IPA 80:20, 1.0 mL/min, 239 nM, 30° C.) R$_t$ (min)=18.61 (R isomer), 28.76 min (S isomer); $[\alpha]_D^{24}$=+43.07 (c 0.570 in MeOH) for 95.5% ee (R) [lit. value $[\alpha]_D^{27}$=+52.0 (c 0.54 in MeOH) 99% ee (R)]$^x$.

T. Ohkuma, M. Koizumi, H. Doucet, T. Pham, M. Kozawa, K. Murata, E. Katayama, T. Yokozawa, T. Ikariya, R. Noyori. *J. Am. Chem. Soc.*, 1998, 120, 13529-13530.

(R)-1-[(4'-Dimethylamino)phenyl]ethanol SRC 1258/1260

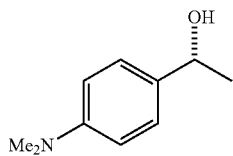

$\delta_H$ (400 MHz, CDCl$_3$) 7.25 (2H, d, J 8.7, —CH of Ph), 6.72 (2H, d, J 8.7, —CH of Ph), 4.81 (1H, t, J 6.4, —CH), 2.93 (6H, s, N(CH$_3$)$_2$), 1.78 (1H, br s, —OH), 1.47 (3H, d, J 6.4, —CH$_3$); $\delta_C$ (100 MHz, CDCl$_3$): 150.17, 133.17, 126.41 (2C), 112.57 (2C), 70.10, 40.67 (2C), 24.64; the enantiomeric excess determined by chiral HPLC analysis (ChiralPak OD-H Column: 0.46 cm×25 cm, hexane:IPA 95:5, 1.0 mL/min, 256 nM, 30° C.) R$_t$ (min)=15.21 (R isomer), 17.15 min (S isomer); [α]$_D^{27}$=+54.2 (c 0.710 in CHCl$_3$) for 91% ee (R) [lit. value [α]$_D^{25}$=+51.8 (c 21.0 in CHCl$_3$) 86% ee (R)]$^x$.

T. Inagaki, L. T. Phong, A. Furuta, J. Ito, H. Nishiyama. *Chem. Eur. J.* 2010, 16, 3090-3096

Polymer-Supported Catalysts

N-((1R,2R)-2-(3-(4-(Hex-5-ynyloxy)phenyl)propylamino)-1,2-diphenylethyl)-4-methylbenzenesulfonamide This compound was prepared according to general procedure 5 using 3 ethyl-3-(4-(hex-5-ynyloxy)phenyl)propan-1-ol (400 mg, 1.72 mmol), 2,6-lutidine (353 mg, 3.30 mmol), trifluoromethanesulfonic anhydride (787 mg, 2.80 mmol), (R,R)-TsDPEN (403 mg, 1.10 mmol), Et$_3$N (263 mg, 2.60 mmol) and DCM (8 cm$^3$). The product was purified by column chromatography as in the general procedure. TLC: silica gel, 30% EtOAc in petroleum ether, product Rf=0.36 with visualisation by UV and KMnO$_4$, 2,6-lutidine Rf=0.29 with visualisation by UV, 2,6-lutidine elutes with the product). The fractions containing the product were collected, combined and dried under reduced pressure to give a white solid. The solid was then washed with pentane to remove residual 2,6-lutidine. The mixture was filtered and the solid dried to give the product as a white solid (524 mg, 0.900 mmol, 82% based on 403 mg, 1.1 mmol N-(2-aminoethyl)-4-methylbenzenesulfonamide)). Mp 123-124° C.; [α]$_D^{27}$−25.2 (c 0.25 in CHCl$_3$) (R,R); (found (ESI): M$^+$+H, 581.2833 C$_{36}$H$_{41}$N$_2$O$_3$S requires M, 581.2832); $\upsilon_{max}$ 3286, 3248, 2915, 1510, 1454, 1434, 1316, 1242, 1160, 1031, 808, 700 cm$^{-1}$; $\delta_H$ (400 MHz, CDCl$_3$) 7.37 (2H, d, J 8.5 Hz, CHArSO$_2$), 7.13-7.11 (3H, m, CHAr), 7.05-6.88 (12H, m, CHAr and NHSO$_2$ overlapping), 6.78 (2H, d, J 8.5 Hz, CHArSO$_2$), 6.28 (1H, br s, NH), 4.25 (1H, d, J 7.8 Hz, CHNSO$_2$), 3.95 (2H, t, J 5.0 Hz, CH$_2$OAr), 3.59 (1H, d, J 7.8 Hz, CHN), 2.51-2.38 (3H, m, ArCH$_2$ and CH$_2$N overlapping), 2.31 (3H, s, CH$_3$), 2.29-2.24 (3H, m, HCCCH$_2$ and CH$_2$N overlapping), 1.96 (1H, t, J 2.6 Hz, HCCCH$_2$), 1.92-1.85 (2H, m, CH$_2$CH$_2$CH$_2$OAr), 1.75-1.61 (4H, m, CH$_2$CH$_2$N and HCCCH$_2$CH$_2$); $\delta_C$ (100 MHz, CDCl$_3$) 157.20 (CAr), 142.70 (CAr), 139.33 (CAr), 138.39 (CAr), 137.09 (CAr), 133.79 (CAr), 129.21 (2 CHAr), 129.10 (2 CHAr), 128.31 (2 CHAr), 127.93 (2 CHAr), 127.58 (2 CHAr), 127.46 (CHAr), 127.41 (2 CHAr), 127.29 (CHAr), 127.13 (2 CHAr), 114.39 (2 CHAr) 84.18 (C), 68.64 (CH), 67.77 (CH), 67.29 (CH$_2$), 63.09 (CH), 46.45 (CH$_2$), 32.37 (CH$_2$), 31.71 (CH$_2$), 28.37 (CH$_2$), 25.11 (CH$_2$), 21.46 (CH$_3$), 18.19 (CH$_2$); m/z (ESI) 581.3 (M$^+$+1).

(R,R)-3C-Tethered Monomer with o-Hexyne Substituent

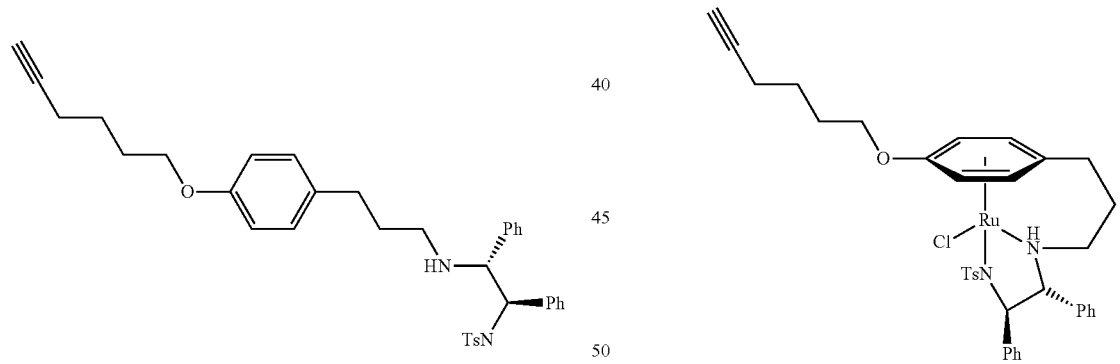

This compound was prepared as for general procedure 7 using N-((1R,2R)-2-(3-(4-(hex-5-ynyloxy)phenyl)propylamino)-1,2-diphenylethyl)-4-methylbenzene sulfonamide (116 mg, 0.2 mmol), ethylbenzoate ruthenium(II)chloride dimer (64 mg, 0.1 mmol), DCM (5 cm$^3$) and chlorobenzene (13.4 cm$^3$). After 5 hours at 90° C. mass spectrometry analysis showed the desired monomer 2:1 two isomers (m/z 681.2 [M$^+$+H−Cl]). Due to the small scale of the reaction, the product was not purified. The reaction was carried out as proof of concept for aryl substitution with this ligand structure prior to preparing the polymer supported derivatives.

N-((1R,2R)-2-(3-(4-(4-(3-Benzyl-3H-1,2,3-triazol-4-yl)butoxy)phenyl)propylamino)-1,2-diphenylethyl)-4-methylbenzenesulfonamide

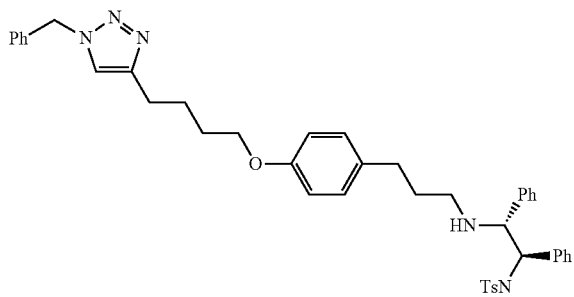

To a nitrogen purged flask was added the N-((1R,2R)-2-(3-(4-(hex-5-ynyloxy)phenyl)propylamino)-1,2-diphenylethyl)-4-methylbenzenesulfonamide (116 mg, 0.200 mmol), Cu(OAc)$_2$ (7 mg, 0.04 mmol) and sodium-(L)-ascorbate (16 mg, 0.08 mmol) and degassed solution of 1/1 THF/water (5 cm$^3$). To the stirred solution was then added benzyl azide (32 mg, 0.24 mmol). The reaction became a blue colour when stirred and then became cloudy white. The reaction was stirred at room temperature for 48 hours. After this EtOAc (10 cm$^3$) was added followed by ammonium hydroxide (35%) solution. The EtOAc was separated and aqueous phase extracted with further EtOAc (2×10 cm$^3$). The EtOAc phases were combined and washed with further ammonium hydroxide (35%) solution. The EtOAc phases were dried over Na$_2$SO$_4$, filtered and the solvent removed under reduced pressure to leave the product as a white solid (140 mg, 0.19 mmol, 95%). Purification was not necessary. Mp 123-124° C.; $[\alpha]_D^{27}$ −25.2 (c 0.25 in CHCl$_3$) (R,R); (found (ESI): M$^+$+H, 714.3481 C$_{43}$H$_{48}$N$_5$O$_3$S requires M, 714.3472); $\upsilon_{max}$ 2925, 1510, 1454, 1324, 1241, 1155, 1047, 811, 698 cm$^{-1}$; $\delta_H$ (400 MHz, CDCl$_3$) 7.38-7.34 (4H, m, CHAr), 7.25-7.21 (3H, m, CHAr), 7.13-7.10 (3H, m, CHAr), 7.04-7.00 (5H, m, CHAr), 6.97-6.88 (6H, m, CHAr), 6.75 (2H, d, J 8.5 Hz, CHAr), 6.30 (1H, br s, NH), 5.46 (2H, s, ArCH$_2$NNN), 4.25 (1H, d, J 7.9 Hz, CHNHSO$_2$), 3.93 (2H, t, J 5.7 Hz, CH$_2$OAr), 3.59 (1H, d, J 7.9 Hz, CHNH), 2.76 (2H, t, J 7.0 Hz, CH$_2$CNNN), 2.49-2.38 (3H, m, CH$_2$Ar and CHHNH), 2.31-2.24 (4H, m, CH$_3$ and CHHNH overlapping), 1.84-1.81 (4H, m, CH$_2$CH$_2$CH$_2$CH$_2$OAr), 1.69-1.61 (2H, m, CH$_2$CH$_2$NH); $\delta_C$ (100 MHz, CDCl$_3$) 157.18 (CAr), 148.42 (CAr), 142.72 (CAr), 139.31 (CAr), 138.40 (CAr), 137.09 (CAr), 133.76 (CAr), 129.21 (2 CHAr), 129.12 (2 CHAr), 129.09 (2 CHAr), 128.64 (CHAr), 128.31 (2 CHAr), 128.01 (2 CHAr), 127.93 (2 CHAr), 127.58 (2 CHAr), 127.45 (2 CHAr), 127.28 (CHAr), 127.11 (2 CHAr), 120.72 (CHAr), 114.37 (2 CHAr), 82.82 (CH), 67.76 (CH), 67.52 (CH$_2$), 65.19 (C), 63.14 (CH), 62.18 (C), 54.01 (CH$_2$), 46.44 (CH$_2$), 32.37 (CH$_2$), 31.70 (CH$_2$), 28.88 (CH$_2$), 25.98 (CH$_2$), 25.46 (CH$_2$), 21.46 (CH$_3$); m/z (ESI) 714.3 (M$^+$+1).

(R,R)-3C-Tethered Ruthenium Monomer with Triazole Linker

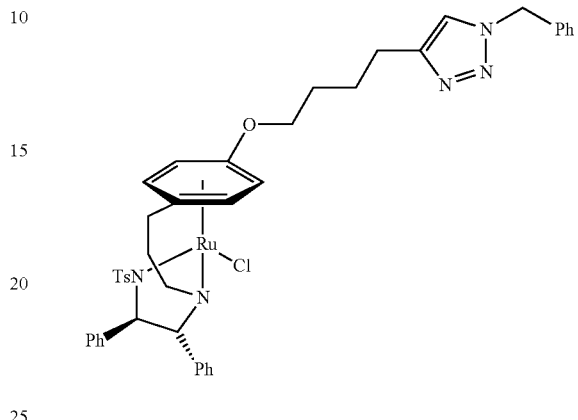

This compound was prepared as for general procedure 7 using N-((1R,2R)-2-(3-(4-(4-(3-benzyl-3H-1,2,3-triazol-4-yl)butoxy)phenyl)propylamino)-1,2-diphenylethyl)-4-methylbenzenesulfonamide (36 mg, 0.05 mmol), ethylbenzoate ruthenium(II)chloride dimer (16 mg, 0.025 mmol), DCM (1.3 cm$^3$) and chlorobenzene (3.3 cm$^3$). After 5 hours mass spectrometry analysis showed the desired monomer 3:1 two isomers (m/z 814.2 [M$^+$+H−Cl]). Due to the small scale of the reaction, the product was not isolated. The reaction was carried out as proof of concept for aryl substitution with this ligand structure prior to preparing the polymer supported derivatives.

Azido Opened Polymer.

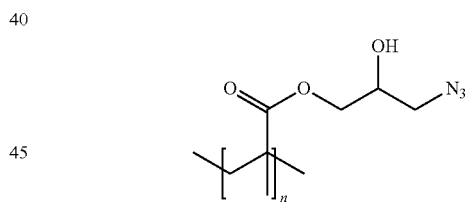

This compound is known in the literature and has previously been fully characterised. To poly(glycidyl methacrylate) Mn~20,000 (568 mg, 4 mmol epoxide) was added NaN$_3$ (780 mg, 12 mmol) and NH$_4$Cl (636 mg, 12 mmol). To this was then added anhydrous DMF (40 cm$^3$). The reaction was stirred at 50° C. for 24 hours. The reaction was cooled to room temperature and water was added until a white precipitate formed. The precipitate was collected by filtration and dried to give the product as a white solid (565 mg, 3.3 mmol repeat units, 83%). Mp 250° C. (decomposed); $\upsilon_{max}$ 3427, 2987, 2096, 1720, 1251, 1149, 1089, 747 cm$^{-1}$; $\delta_H$ (300 MHz, THF) 4.71 (1H, br s, OH), 3.87-3.84 (3H, m, COOCH$_2$ and CH overlapping), 3.25 (2H, br s, CH$_2$N$_3$), 1.86-1.78 (2H, m, CH$_2$CCH$_3$), 0.99-0.83 (3H, m, CH$_2$CCH$_3$); $\delta_C$ (75 MHz, THF) 176.71 (C=O), 68.29 (CH), 66.11 (CH$_2$), 53.79 (CH$_2$), 44.71 (CH$_2$), 16.78 (CH$_3$). Ref: N. V. Tsarevsky, S. A. Bencherif and K. Matyjaszewski, *Macromolecules* 2007, 40, 4439-4445.

Ligand Functionalised Polymer.

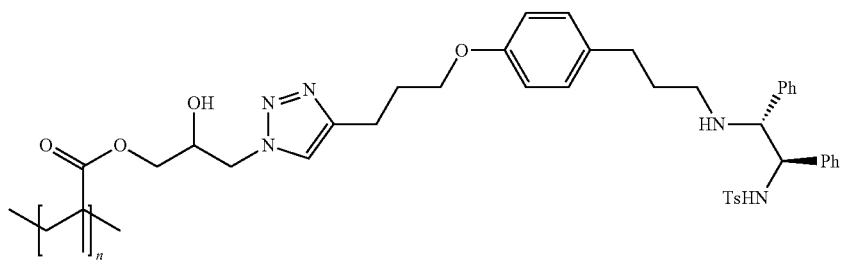

To a nitrogen purged flask was added the azido opened polymer (45 mg, 0.20 mmol $N_3$) and N-((1R,2R)-2-(3-(4-(hex-5-ynyloxy)phenyl)propylamino)-1,2-diphenylethyl)-4-methylbenzenesulfonamide (113 mg, 0.20 mmol). To this was then added $Cu(OAc)_2$ (7 mg, 0.04 mmol) and sodium-(L)-ascorbate 16 mg, 0.08 mmol followed by degassed THF/water 1/1 (5 cm$^3$). The reaction was stirred at room temperature for 48 hours. A blue precipitate formed and was collected by filtration. This was washed with ammonium hydroxide (aq.) and dried to give the product as a blue/green insoluble gel (147 mg, 0.19 mmol clicked ligand). $\upsilon_{max}$ 3375, 2987, 2901, 2103 (weak $N_3$ signal), 1726, 1241, 1152, 1077, 1056, 810, 698, 665, 548 cm$^{-1}$.

Polymer Supported (R,R)-3C-Tethered Ru Complex (A).

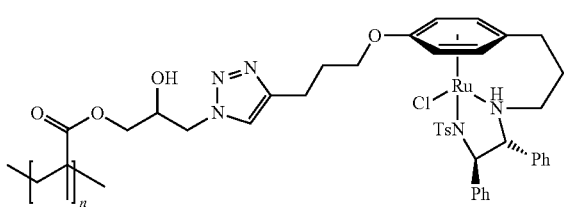

To a nitrogen purged flask was added the ligand functionalised polymer described above (100 mg, 0.13 mmol ligand) was added the ethylbenzoate ruthenium(II)chloride dimer (42 mg, 0.065 mmol). To this was then added anhydrous DCM (3.4 cm$^3$) and the solution was stirred at room temperature for 30 min. The DCM was removed under reduced pressure and was replaced with chlorobenzene (8.6 cm$^3$) and the reaction was stirred at 90° C. for 5 hours. The chlorobenzene was removed under vacuum to leave the product as a red/brown insoluble solid. This was washed with further DCM to remove unreacted ethylbenzoate ruthenium(II)chloride dimer to give the product (97 mg, 0.11 mmol Ru catalyst, 85%). MP 234° C. (decomposed); $\upsilon_{max}$ 3406, 2931, 1720, 1510, 1445, 1269, 1156, 1106, 1049, 810, 744, 699 cm$^{-1}$;

1:9 Ligand:Hexyne Functionalised Polymer.

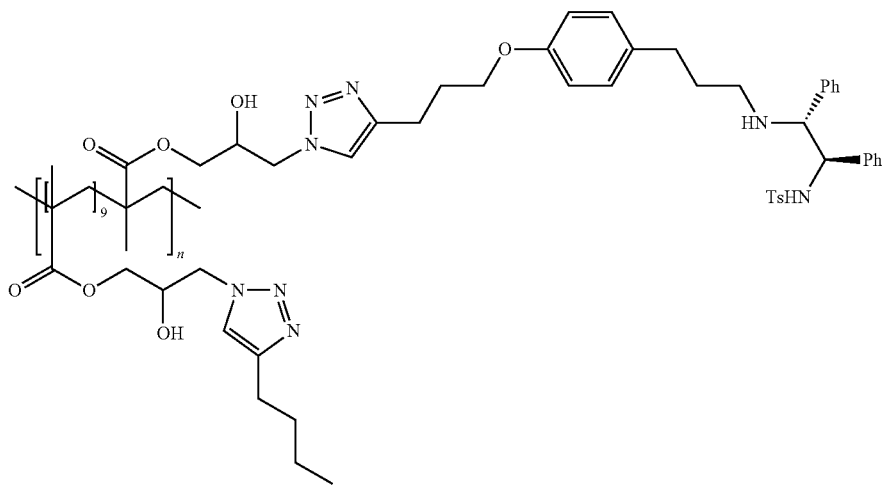

To a nitrogen purged flask was added the azido opened polymer (97 mg, 0.50 mmol $N_3$) and N-((1R,2R)-2-(3-(4-(hex-5-ynyloxy)phenyl)propylamino)-1,2-diphenylethyl)-4-methylbenzenesulfonamide (29 mg, 0.05 mmol) and hexyne (37 mg, 0.45 mmol). To this was then added $Cu(OAc)_2$ (18 mg, 0.1 mmol) and sodium-(L)-ascorbate (40 mg, 0.2 mmol) and THF/water 4/1 (10 cm$^3$). The reaction was stirred at room temperature for 48 hours. After this the product had separated from solution as a blue/green jelly. This was removed, washed with ammonium hydroxide (aq.) (35%) and dried to give the product as an insoluble blue gel (103 mg, 0.035 mmol ligand/ 0.32 mmol clicked hexyne, 70%). $\upsilon_{max}$ 3265, 2954, 2931, 2871, 1728, 1453, 1149, 1058, 809, 701, 665, 549 cm$^{-1}$.

1:9 (R,R)-3C-Tethered Ru Complex:Hexyne Functionalised Polymer (B).

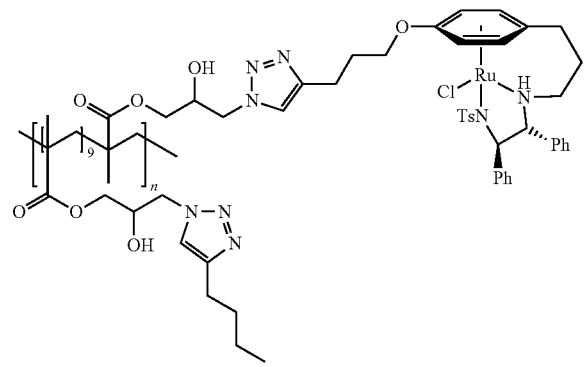

To a nitrogen purged flask was added 1:9 ligand:hexyne functionalised polymer described above (100 mg, 0.034 mmol ligand) was added ethylbenzoate ruthenium(II)chloride dimer (11 mg, 0.017 mmol) and anhydrous DCM (0.9 cm³). The reaction was stirred at room temperature for 30 min before the DCM was removed under reduced pressure. Chlorobenzene (2.2 cm³) was added and the reaction stirred at 90° C. for 5 hours. After this the reaction was cooled to room temperature, filtered and the solid dried to give the product as a red/brown solid. This was washed with further DCM to remove unreacted ethylbenzoate ruthenium(II)chloride dimer to give the product (70 mg, 0.021 mmol Ru catalyst, 62%). $\upsilon_{max}$ 3230, 3079, 2930, 1722, 1443, 1396, 1367, 1288, 1268, 1149, 1105, 1054, 771, 746, 700, 665 cm⁻¹.

3:7 Ligand:Hexyne Functionalised Polymer.

To a nitrogen purged flask was added the azido opened polymer (93 mg, 0.5 mmol N₃) and N-((1R,2R)-2-(3-(4-(hex-5-ynyloxy)phenyl)propylamino)-1,2-diphenylethyl)-4-methylbenzenesulfonamide (87 mg, 0.15 mmol) and hexyne (29 mg, 0.35 mmol). To this was then added Cu(OAc)₂ (18 mg, 0.1 mmol) and sodium-(L)-ascorbate (40 mg, 0.2 mmol) and THF/water 4/1 (10 cm³). The reaction was stirred at room temperature for 48 hours. After this the product had separated from solution as a blue/green jelly. This was removed, washed with ammonium hydroxide (aq.) (35%) and dried to give the product as an insoluble blue gel (180 mg, 0.13 mmol ligand/ 0.30 mmol clicked hexyne, 87%). $\upsilon_{max}$ 3272, 2930, 2869, 1727, 1454, 1242, 1152, 1055, 810, 699, 665, 548 cm⁻¹.

3:7 (R,R)-3C-Tethered Ru Complex:Hexyne Functionalised Polymer (C).

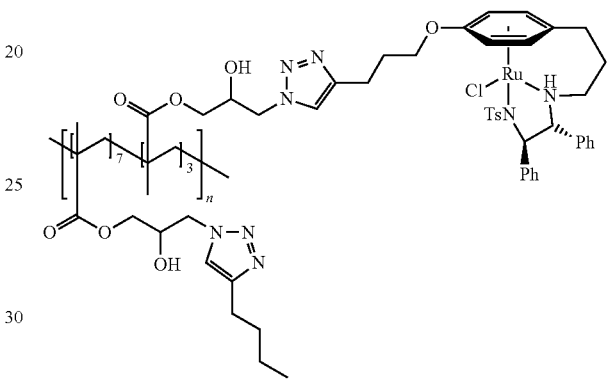

This compound was prepared using 3:7 ligand:hexyne functionalised polymer described above (180 mg, 0.13 mmol ligand), ethylbenzoate ruthenium(II)chloride dimer (42 mg, 0.065 mmol), anhydrous DCM (1.2 cm³) and chlorobenzene (2.8 cm³) to give the product (189 mg, 0.12 mmol Ru catalyst, 92%). $\upsilon_{max}$ 3687, 3674, 2972, 2901, 1723, 1394, 1251, 1056, 861, 679, 565 cm⁻¹.

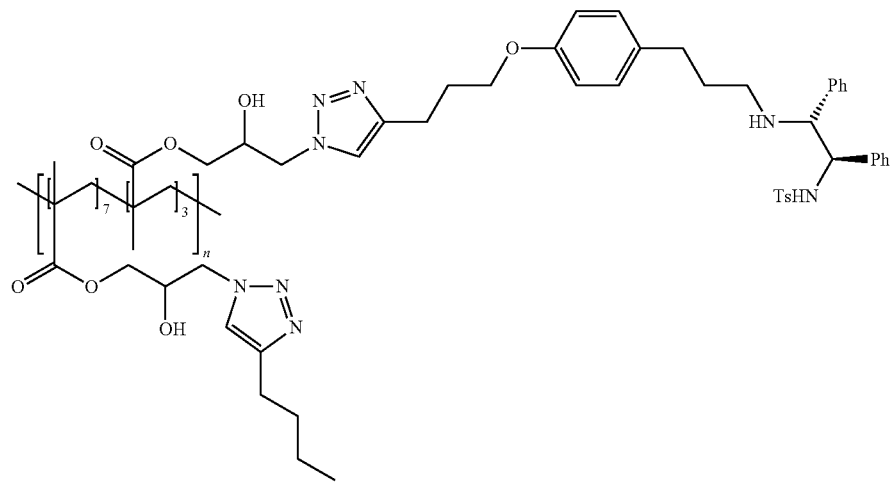

10% Azido Opened poly(glycidyl methacrylate).

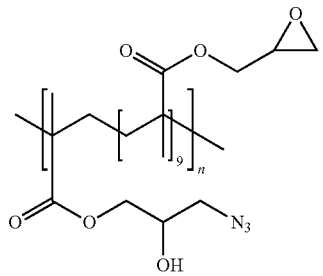

To a nitrogen purged flask was added poly(glycidyl methacrylate) Mn 20,000 (568 mg, 4 mmol epoxide) was added NaN$_3$ (26 mg, 0.4 mmol) and NH$_4$Cl (21 mg, 0.4 mmol). To this was then added anhydrous DMF (40 cm$^3$). The reaction was stirred at 50° C. overnight. The reaction was cooled to room temperature and DMF removed under vacuum. The residue was then washed with water and dried to leave a viscous, sparingly soluble colourless gel (330 mg, 0.23 mmol N$_3$/2.0 mmol epoxide, 58%). $\upsilon_{max}$ 3435 (weak), 2932, 2102 (weak), 1728 (weak), 1665, 1386, 1255, 1148, 1091, 658 cm$^{-1}$; $\delta_H$(400 MHz, THF) 4.61 (0.1H, br s, OH), 4.17 (0.9H, br s, COOCH$^a$H$^b$), 3.89-3.84 (0.3H, m, COOCH$_2$ and CHOH overlapping), 3.70 (0.9H, br s, COOCH$^a$H$^b$), 3.24 (0.2H, br s, CH$_2$N$_3$), 3.10 (0.9H, br s, COOCH$_2$CH), 2.66 (0.9H, br s, CH$^a$H$^b$O in epoxide), 2.51 (0.9H, br s, CH$^a$H$^b$O in epoxide), 1.91-1.81 (2H, CH$_2$CCH$_3$), 1.00-0.84 (3H, m, CH$_3$); $\delta_C$ (100 MHz, DMSO) quaternary carbon CC=O not observed 162.28 (1C, s), 143.17 (1C, s), 65.70 (1C, s), 65.45 (1C, s), 48.57 (1C, s), 48.49 (1C, s), 43.79 (1C, s), 39.96 (1C, s), 35.75 (1C, s), 30.67 (1C, s).

1:9 Azido:Diethylamine Functionalised poly(glycidyl methacrylate).

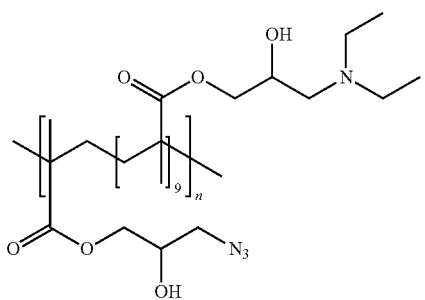

To a nitrogen purged flask connected to a condenser was added 10% azide opened poly(glycidyl methacrylate) (230 mg, 1.44 mmol epoxide/0.16 mmol N$_3$) was added DMSO (2.5 cm$^3$) and diethylamine (124 mg, 1.7 mmol). The reaction was stirred at 60° C. overnight. After this the reaction was cooled to room temperature and the DMSO removed under vacuum with gentle heating to leave the product as a straw coloured, insoluble, viscous gel (280 mg, 0.15 mmol N$_3$/1.4 mmol diethylamine, 97%). $\upsilon_{max}$ 3386, 2965, 2931, 2101, 1724, 1438, 1385, 1269, 1152, 1020, 952 cm$^{-1}$. For procedure see reference 164.

1:9 Ligand:Diethylamine Functionalised Polymer.

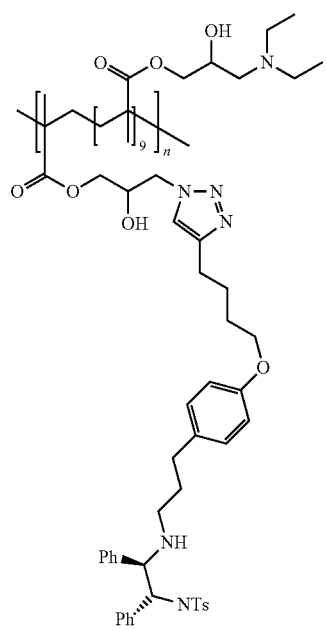

To a nitrogen purged flask was added 1:9 azide:diethylamine opened poly(glycidyl methacrylate) described above (280 mg, 0.15 mmol N$_3$/1.4 mmol diethylamine) and N-((1R, 2R)-2-(3-(4-(hex-5-ynyloxy)phenyl)propylamino)-1,2-diphenylethyl)-4-methylbenzenesulfonamide (87 mg, 0.15 mmol). To this was then added Cu(OAc)$_2$ (5.5 mg, 0.03 mmol) and sodium-(L)-ascorbate (12 mg, 0.06 mmol) followed by THF/water 4/1 (3 cm$^3$). The reaction was stirred at room temperature for 48 hours. The reaction was filtered and the solid was washed with ammonium hydroxide (aq.) (35%) and dried to leave a blue/green insoluble solid (250 mg, 0.09 mmol clicked ligand/0.81 mmol diethylamine, 75%). $\upsilon_{max}$ 3344, 2968, 2936, 1726, 1453, 1386, 1374, 1241, 1151, 1060, 811, 700 cm$^{-1}$.

1:9 (R,R)-3C-Tethered Ru Complex:Diethylamine Functionalised Polymer (D).

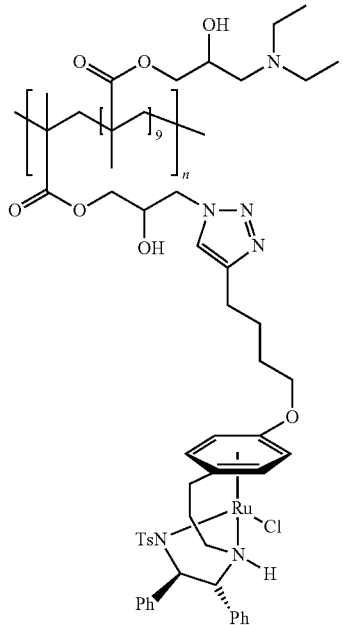

This compound was prepared as for 256 using 1:9 ligand: diethylamine functionalised polymer described above (250 mg, 0.09 mmol clicked ligand), ethylbenzoate ruthenium(II) chloride dimer 197 (29 mg, 0.045 mmol), anhydrous DCM (0.8 cm$^3$) and chlorobenzene (2 cm$^3$) to give the product (141 mg, 0.05 mmol Ru/0.45 mmol diethylamine, 56%). $\upsilon_{max}$ 3374, 2967, 1724, 1665, 1453, 1386, 1266, 1151, 1084, 997, 746, 700 cm$^{-1}$ Microwave Reactions:

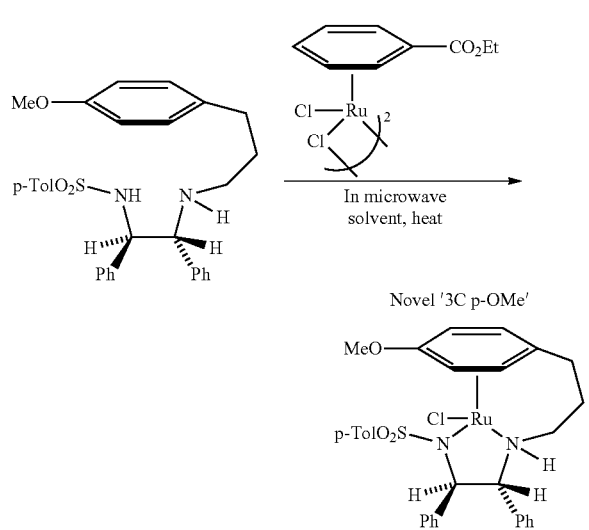

4-OMe complex formation in chlorobenzene using Microwave SRC 1304(1):

A solution of ligand $C_{31}H_{34}N_2O_3S$ (50 mg, 1.0 eq) and [Ru($C_9H_{10}O_2$)$Cl_2$]$_2$ (31.6 mg, 0.5 eq) in chlorobenzene (3 mL) was placed in glass tube, sealed and irradiated with microwave radiation under the following conditions. The reaction mixture was analysed by ESI-MS and TLC after each run. ESI-MS complied for required complex formation with [M-Cl]$^+$ peak at 615.0.

1st run: Power=40 W, Temp=90° C., RAMP=1 min, Hold=10 min. Product visible by TLC on silica gel and by ESI-MS, shown in FIG. 4.

2nd run: Power=40 W, Temp=90° C., RAMP=1 min, Hold=10 min. Product visible by TLC on silica gel and ESI MS but with signs of decomposition is shown in FIG. 5.

4-OMe complex formation using Microwave (intermediate preformed in DCM) SRC 1304(2):

A solution of ligand $C_{31}H_{34}N_2O_3S$ (50 mg, 1.0 eq) and [Ru($C_9H_{10}O_2$)$Cl_2$]$_2$ (31.6 mg, 0.5 eq) in DCM (3 mL) was stirred at room temperature under an inert atmosphere for 30 min. The mixture was concentrated on a rotavapor to give orange residue. The residue was dissolved in chlorobenzene (3 mL), transferred to a glass tube, sealed and irradiated with microwave radiation under the following conditions. ESI-MS complied for required complex formation with [M-Cl]$^+$ peak at 615.0 with formation of undesired bidentate complex with [M-Cl]$^+$ peak at 764.1. Both desired and undesired complexes were visible by TLC on silica gel.

Power=40 W, Temp=90° C., RAMP=1 min, Hold=10 min is shown in FIG. 6.

4-OMe complex formation in DCM using Microwave SRC 1305(1):

A solution of ligand $C_{31}H_{34}N_2O_3S$ (50 mg, 1.0 eq) and [Ru($C_9H_{10}O_2$)$Cl_2$]$_2$ (31.6 mg, 0.5 eq) in DCM (3 mL) was placed in glass tube, sealed and irradiated with microwave radiation under the following conditions. The reaction mixture was analysed by ESI-MS and TLC after each run. ESI-MS indicated formation of the undesired bidentate complex formation with [M-Cl]$^+$ peak at 765.1. 1st run: Power=40 W, Temp=50° C., RAMP=2 min, Hold=10 min, Pressure=60 psi is shown in FIG. 7.

2nd run: Power=40 W, Temp=50° C., RAMP=2 min, Hold=10 min, Pressure=60 psi.

3rd run: Power=80 W, Temp=75° C., RAMP=2 min, Hold=10 min, Pressure=100 psi is shown in FIG. 8.

4-OMe complex formation in DCE using Microwave SRC 1305(2):

A solution of ligand $C_{31}H_{34}N_2O_3S$ (50 mg, 1.0 eq) and [Ru($C_9H_{10}O_2$)$Cl_2$]$_2$ (31.6 mg, 0.5 eq) in DCE (3 mL) was placed in glass tube, sealed and irradiated with microwave radiation under the following conditions. The reaction mixture was analysed by ESI-MS and TLC after each run. ESI-MS complied with undesired bidentate complex formation with [M-Cl]$^+$ peak at 765.1 after 1$^{st}$ run and there was required complex formation after 2$^{nd}$ run with [M-Cl]$^+$ peak at 614. But complex formation was not clean as observed in reaction carried out in chlorobenzene.

Figure 9:
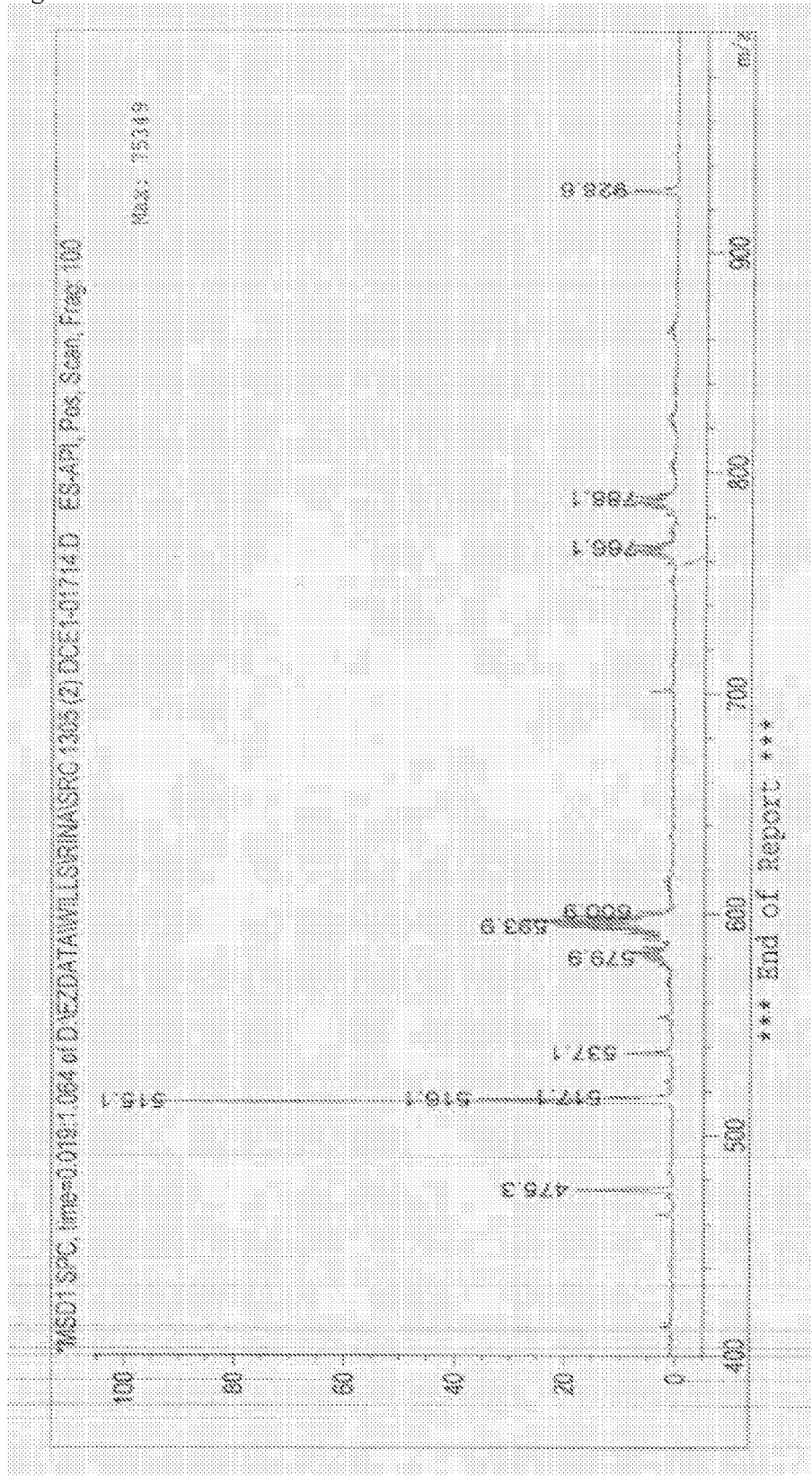

1st run: Power=80 W, Temp=80° C., RAMP=2 min, Hold=10 min, Pressure=60 psi is shown in FIG. 9.

2nd run: Power=80 W, Temp=100° C., RAMP=2 min, Hold=10 min, Pressure=60 psi is shown in FIG. 10.

MW Reactions on Other Ligands (F16).

Ligand (0.05 mmol) and [RuC$_6$H$_5$CO$_2$EtCl$_2$]$_2$ (0.025 mmol) were dissolved in chlorobenzene (1.5 ml) and the resulting solution was stirred at rt for 5 min. The mixture was heated to 90° C./130° C. (Power=100 W Pressure=60 psi) in a microwave reactor for 10 min and results were recorded by mass spectrometry.

F16 4 and 8

Ligand (24.3 mg, 0.05 mmol) and [RuC$_6$H$_5$CO$_2$EtCl$_2$]$_2$ (15.8 mg, 0.025 mmol) were dissolved in chlorobenzene (1.5 ml) and the resulting solution was stirred at rt for 5 min. The mixture was heated to 90° C./130° C. in microwave MW reactor for 10 min results were recorded by MS.

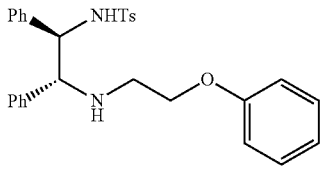

product formed by MS under 130° C. in MW for 10 min but did not form under 90° C. in microwave for 10 min is shown in FIG. 11.

F16 3 and 7

Ligand (28.8 mg, 0.05 mmol) and [RuC$_6$H$_5$CO$_2$EtCl$_2$]$_2$ (15.8 mg, 0.025 mmol) were dissolved in chlorobenzene (1.5 ml) and the resulting solution was stirred at rt for 5 min. The mixture was heated to 90° C./130° C. in microwave reactor for 10 min results were recorded by MS.

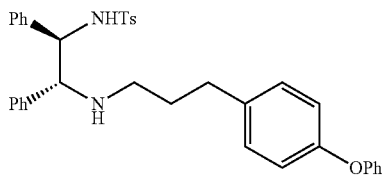

product formed by MS under 130° C. in MW for 10 min but did not form under 90° C. in microwave for 10 min is shown in FIG. 12.

F16 5

Ligand (27.2 mg, 0.05 mmol) and [RuC$_6$H$_5$CO$_2$EtCl$_2$]$_2$ (15.8 mg, 0.025 mmol) were dissolved in chlorobenzene (1.5 ml) and the resulting solution was stirred at rt for 5 min. The mixture was heated to 90° C./130° C. in microwave reactor for 10 min results were recorded by MS.

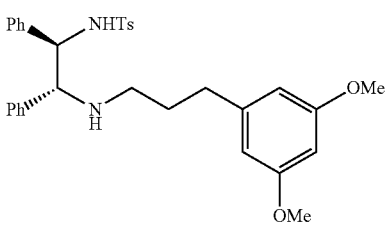

product formed by MS 130° C. in MW for 10 min but did not form under 90° C. in microwave for 10 min is shown in FIG. 13.

Synthesis of Ligands for the Microwave Studies Above

N-{(1R,2R)-2-[3-(4-phenoxyphenyl)propylamino]-1,2-diphenylethyl}-4-methylbenzenesulfonamide SRC 997

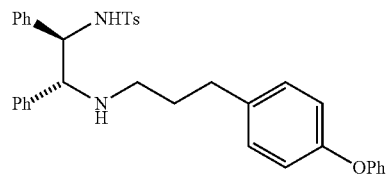

To a mixture of C$_{15}$H$_{16}$O$_2$ (0.249 g, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) into dry DCM (2.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R)TsDPEN (0.250 g, 0.683 mmol, 1.0 eq) and TEA (0.228 mL, 1.639 mmol, 2.4 eq) in dry DCM (2.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×25 mL). The organic layer was separated, washed with H$_2$O (2×15 mL), brine (25 mL), dried over anhy. Na$_2$SO$_4$, filtered and concentrated to give crude compound. The crude compound was purified by column chromatography over silica gel using EtOAc:Pet. ether (25:75) as an eluent to give residue. The residue was triturated in n-pentane (to remove traces of 2,6-lutidine) to give solid. The solid was filtered, washed with n-pentane and dried under vacuum to give pure compound as white solid (0.295 g, 0.512 mmol, 75%). Mp 54-56° C.; $[\alpha]_D^{28}$=−20.00 (c 0.825 in CHCl$_3$); $v_{max}$ 3298, 3060, 3028, 2926, 2857, 1589, 1487, 1229, 1157, 807, 754, 696, 666 cm$^{-1}$; $\delta_H$ (400 MHz, CDCl$_3$) 7.36 (2H, d, J 8.0, —CH of —SO$_2$C$_6$H$_4$CH$_3$), 7.33-7.29 (2H, m, —CH of phenyl), 7.15-7.11 (3H, m, —CH of phenyl), 7.09-6.98 (9H, m, —CH of phenyl), 6.96-6.89 (7H, m, —CH of phenyl), 6.24 (1H, br s, —NHTs), 4.27 (1H, d, J 7.6, —CHNHTs), 3.60 (1H, d, J 7.6, —CHNH(CH$_2$)$_3$—), 2.58-2.47 (2H, m, —NH—CH$_2$CH$_2$CH$_2$—), 2.45-2.40 (1H, m, —NH—CHHCH$_2$CH$_2$—), 2.34-2.37 (4H, m, —NH—CHHCH$_2$CH$_2$—, —CH$_3$), 1.75-1.61 (2H, m, —NH—CH$_2$CH$_2$CH$_2$—), 1.44 (1H, br s, —NH(CH$_2$)$_3$—); $\delta$c (100 MHz, CDCl$_3$) 155.07 (C), 142.67 (C), 139.23 (C), 138.29 (C), 137.02 (C), 136.71 (C), 129.63 (2CH), 129.48 (2CH), 129.05 (2CH), 128.28 (2CH), 127.90 (2CH), 127.51 (2CH), 127.44 (CH), 127.35 (2CH), 127.26 (CH), 127.08 (2CH), 122.90 (CH), 119.00 (2CH), 118.47 (2CH), 67.73 (CH), 63.02 (CH), 46.37 (CH$_2$), 32.48 (CH$_2$), 31.56 (CH$_2$), 21.4

(CH$_3$); m/z ESI-MS [M+H]$^+$ 577.2; HRMS found 577.2515 (C$_{36}$H$_{36}$N$_2$O$_3$S H+ requires 577.2519, error=1.1 ppm).

4-Methyl-N-[(1R,2R)-2-(2-phenoxyethylamino)-1,2-diphenylethyl]benzenesulfonamide SRC 878

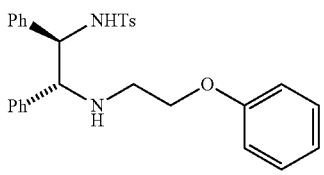

To a mixture of C$_8$H$_{10}$O$_2$ (0.151 g, 1.093 mmol, 1.6 eq) and 2,6-lutidine (0.167 mL, 1.434 mmol, 2.10 eq) in dry DCM (5 mL) was added a solution of triflic anhydride (0.195 mL, 1.161 mmol, 1.70 eq) in dry DCM (2.5 mL) dropwise at 0° C. under an inert atmosphere. The resulting light pink solution was stirred at 0° C. for 30 min and at room temperature for 60 min. The mixture was again cooled down to 0° C. To this, solution of (1R,2R)TsDPEN (0.250 g, 0.683 mmol, 1.0 eq) and TEA (0.228 mL, 1.639 mmol, 2.4 eq) into dry DCM (2.5 mL) was added dropwise at 0° C. The resulting yellow coloured mixture was stirred at 0° C. for 30 min and then at room temperature for 17 h. The reaction mixture was diluted with DCM (20 mL) and washed with sat. NaHCO$_3$ solution (3×25 mL). The organic layer was separated, washed with H$_2$O (2×15 mL), brine (25 mL), dried over anhy. Na$_2$SO$_4$, filtered and concentrated to give crude compound. The crude compound was purified by column chromatography over silica gel using EtOAc:Pet. ether (25:75) as an eluent to give a residue. The residue was triturated in n-pentane (to remove traces of 2,6-lutidine) to give a solid. The solid was filtered, washed with n-pentane and dried under vacuum to give pure compound as white solid (0.250 g, 0.514 mmol, 75%). Mp 130-132° C.; [α]$_D^{28}$=−6.21 (c 0.515 in CHCl$_3$); ν$_{max}$ 3344, 3297, 3064, 3029, 2940, 1600, 1491, 1454, 1433, 1303, 1248, 1159, 807, 754, 696, 668 cm$^{-1}$; δ$_H$ (300 MHz, CDCl$_3$) 7.36 (2H, d, J 8.4, —CH of —SO$_2$C$_6$H$_4$CH$_3$), 7.30-7.24 (2H, m, —CH of phenyl), 7.16-7.11 (3H, m, —CH of phenyl), 7.09-7.02 (3H, m, —CH of phenyl), 6.99-6.93 (7H, m, —CH of phenyl), 6.80 (2H, d, J 7.8, —CH of phenyl), 6.18 (1H, br s, —NHTs), 4.28 (1H, d, J 7.3, —CHNHTs), 4.01-3.87 (2H, m, —CH$_2$CH$_2$OC$_6$H$_5$), 3.73 (1H, d, J 7.3, —CHNHCH$_2$—), 2.84-2.76 (1H, m, —CHHCH$_2$OC$_6$H$_5$), 2.69-2.62 (1H, m, —CHHCH$_2$OC$_6$H$_5$), 2.30 (3H, s, —CH$_3$), 1.79 (1H, br s, —NHCH$_2$—); δc (75 MHz, CDCl$_3$) 157.92 (C), 142.06 (C), 138.30 (C), 137.70 (C), 136.37 (C), 128.84 (2CH), 128.47 (2CH), 127.75 (2CH), 127.36 (2CH), 126.95 (CH), 126.87 (2CH), 126.82 (2CH), 126.71 (CH), 126.46 (2CH), 120.34 (CH), 113.90 (2CH), 67.00 (CH), 66.38 (CH$_2$), 62.47 (CH), 45.52 (CH$_2$), 20.80 (CH$_3$); m/z ESI-MS [M+H]$^+$ 487.1; HRMS found 487.2051 (C$_{29}$H$_{30}$N$_2$O$_3$S H+ requires 487.2050, error=−0.2 ppm).

2) Reactions with the OMe-Substituted Diene which Demonstrate that the OMe Catalyst Cannot be Prepared by the Traditional Route

3-(4-Methoxycyclohexa-1,4-dienyl)propan-1-ol

A flask and condenser set up was cooled to −78° C. with a dry ice/acetone mixture. The system was purged with nitrogen and 3-(4-methoxyphenyl-1-propanol) (1.5 g, 9.02 mmol) and anhydrous ethanol (4.5 mL) was added to the addition funnel. Ammonia gas was added at 0.2 bar, which condensed in the flask to give liquid ammonia (40 mL). The ethanolic solution of 3-(4-methoxyphenyl-1-propanol) was added dropwise with stirring with additional ethanol (0.5 mL portions) added to maintain precipitate dissipation (5 mL in total). Sodium pieces (1.50 g in total) were added, leaving time for the blue color produced to fade before adding more (additional ethanol was added when stirring ceased). Once the blue color started to persist for longer the reaction was left to slowly warm to room temperature overnight. Saturated NH$_4$Cl (35 mL) was slowly added to the resulting solution with great care initially in case of any unreacted sodium present. This was then extracted with DCM (4×20 mL) and the organic layers were collected, combined and dried over Na$_2$SO$_4$ then filtered and concentrated to give the product as a yellow oil as the pure product (1.562 g, 9.29 mmol, 102%); ν$_{max}$ 3361 (OH stretch), 2936, 1665, 1389, 1214, 1171, 1011; δ$_H$ (400 MHz, CDCl$_3$) 5.42 (1H, s, CH═COCH$_3$), 4.63 (1H, s, C═CHCH$_2$), 3.67-3.63 (2H, m, CH$_2$OH), 3.55 (3H, s, CH$_3$), 2.73 (4H, br s, CH$_2$C═C and CH$_2$C═C(CH$_2$)$_3$), 2.08 (2H, t, J 8.0, CH$_2$ (CH$_2$)$_2$OH), 1.74-1.67 (2H, m, CH$_2$CH$_2$OH), 1.50 (1H, br s, OH); δ$_C$ (100 MHz, CDCl$_3$) 152.98 (C), 134.94 (C), 117.67 (CH), 90.39 (CH), 62.69 (CH$_2$), 53.85 (OCH$_3$), 32.91 (CH$_2$), 30.54 (CH$_2$), 29.26 (CH$_2$), 29.08 (CH$_2$); m/z ESI-MS [M+Na]$^+$ 191.1; HRMS found 191.041 (C$_{10}$H$_{16}$O$_2$ Na+ requires 191.1043, error=−0.8 ppm). E. N. Marvell, D. Sturmer and C. Rowell, *Tetrahedron* 1966, 22, 861-866; H.-S. Liu and Y. Han, *Chem. Commun.* 1991, 1484-1485.

N-{2-[3-(4-Methoxycyclohexa-1,4-dienyl)propylamino]-1,2-diphenylethyl}-4-methylbenzenesulfonamide

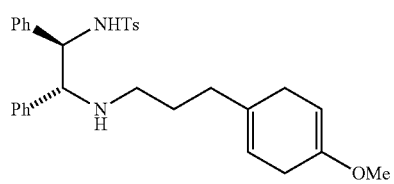

A mixture of 3-(4-methoxycyclohexa-1,4-dienyl)propan-1-ol (0.184 g, 1.093 mmol) and 2,6-lutidine (0.167 mL, 1.434 mmol) in dry DCM (5 mL) under nitrogen was cooled to 0° C. To this was added a mixture of triflic anhydride (0.195 mL, 1.161 mmol) and dry DCM (1.25 mL) dropwise over 5 minutes. The resulting solution was stirred at 0° C. for 30 minutes and then room temperature for 60 minutes. The reaction mixture was again cooled to 0° C. and a solution of (1R,2R)-TsDPEN (0.25 g, 0.683 mmol) and TEA (0.228 mL, 1.639 mmol) in dry DCM (1.25 mL) was added slowly. The resulting solution was stirred at 0° C. for 30 minutes then at room temperature for 18 hours. This was diluted with DCM (7.5 mL) and washed with NaHCO$_3$ (3×15 mL), water (2×7.5 mL) and brine solution (15 mL). The organic layer was dried over Na$_2$SO$_4$, filtered and concentrated to give the crude product. This was purified by column filtration to give pure product (70.5 mg, 0.137 mmol, 20.0%). Mp 88-90° C.; $[\alpha]_D^{29}$=−56.0 (c 0.25 in CHCl$_3$); v$_{max}$ 3302, 2930, 1164, 1215, 1159, 807, 701; $\delta_H$ (400 MHz, CDCl$_3$) 7.36 (2H, d, J 8.4, —CH of phenyl), 7.13-7.12 (3H, m, —CH of phenyl), 7.06-7.01 (5H, m, —CH of phenyl), 6.95-6.89 (4H, m, —CH of phenyl), 6.28 (1H, br s, N—H), 5.25 (1H, br s, CH═C), 4.60 (1H, br s, CH═C), 4.24 (1H, d, J 7.8, —CHNHTs), 3.59 (1H, d, J 7.8, CHNH(CH$_2$)$_3$—), 3.54 (3H, s, —OCH$_3$), 2.66 (4H, br s, CH$_2$C═C and CH$_2$C═C(CH$_2$)$_3$), 2.41-2.35 (1H, m, —NH—CHHCH$_2$CH$_2$—), 2.33 (3H, s, —CH$_3$), 2.29-2.23 (1H, m, —NH—CHHCH$_2$CH$_2$—), 1.95-1.86 (2H, m, —NH—CH$_2$CH$_2$CH$_2$—), 1.56-1.43 (2H, m, —NH—CH$_2$CH$_2$CH$_2$—); $\delta_C$ (100 MHz, CDCl$_3$) 152.95 (C), 142.62 (C), 139.30 (C). 138.34 (C), 137.03 (C), 134.71 (C), 129.03 (2CH), 128.24 (2CH), 127.87 (2CH), 127.50 (2CH), 127.39 (CH), 127.33 (2CH), 127.22 (CH), 127.07 (2CH), 117.66 (CH), 90.36 (CH), 67.76 (CH), 63.02 (CH), 53.85 (OCH$_3$), 46.60 (CH$_2$), 34.02 (CH$_2$), 29.14 (CH$_2$), 29.06 (CH$_2$), 27.76 (CH$_2$), 21.39 (CH$_3$); m/z ESI-MS [M+H]$^+$ 517.1; HRMS found 517.2519 (C$_{31}$H$_{36}$N$_2$O$_3$S H+ requires 517.2519, error=−0.2 ppm). Tosylation of 3-(4-methoxycyclohexa-1,4-dienyl)propan-1-ol was described in H.-S. Liu and Y. Han, *Chem. Commun.* 1991, 1484-1485.

Attempted Synthesis of {N-[(1R,2R)-2-[3-(4-methoxyphenyl)propylammonium chloride]-1,2-diphenylethyl]-4-methylbenzenesulfonamide}ruthenium chloride dimer 4 using N-{2-[3-(4-Methoxycyclohexa-1,4-dienyl)propylamino]-1,2-diphenylethyl}-4-methylbenzenesulfonamide

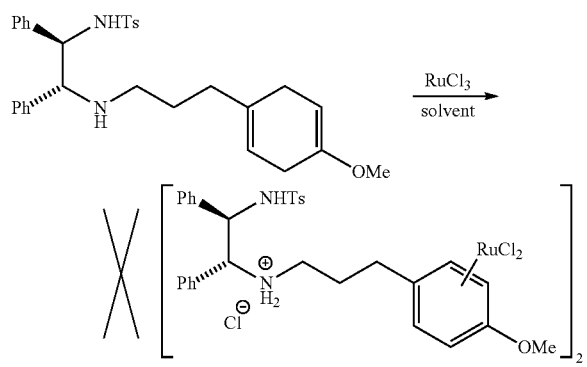

SRC 936, 26 Jul. 2012.

N-{2-[3-(4-Methoxycyclohexa-1,4-dienyl)propylamino]-1,2-diphenylethyl}-4-methylbenzenesulfonamide (0.250 g, 0.484 mmol) in dry DCM (5 mL) under an inert atmosphere was cooled to 0° C. To this, HCl (2M in Et$_2$O, 0.726 mL) was added and stirred for 30 min. The mixture was concentrated on a rotavapor to give a white solid. The solid was dissolved in anhydrous EtOH (10 mL) under an inert atmosphere. To this, RuCl$_3$. xH$_2$O (0.101 g, 0.387 mmol, 0.8 eq) was added and the resulting mixture was heated at 80° C. for 16 h. The reaction mixture was cooled to room temperature and filtered to give a black solid (20 mg; mostly decomposed ruthenium chloride). The filtrate was concentrated to give a green residue (0.2 g). The $^1$H-NMR of residue was complex with no evidence of the required product. ESI-MS complied with aromatised starting compound is shown in FIG. 14.

SRC 1209, 11 Jun. 2013.

A solution of HCl salt of ligand (0.250 g, 1.3 eq) and RuCl$_3$. xH$_2$O (1.0 eq) in methanol was refluxed at 65° C. for 16 h to give a reddish orange mixture (methanol was used instead of ethanol). No solid separated out. The solvent was evaporated on a rotavapor and solid residue (0.379 g, crude) was analysed by 1H-NMR and ESI-MS. ESI-MS complied with aromatised starting compound is shown in FIG. 15.

SRC 1219a, 19 Jun. 2013.

A solution of HCl salt of ligand (0.150 g, 1.0 eq) and RuCl$_3$. xH$_2$O (15 mg, 0.2 eq) in methanol was refluxed at 65° C. for 16 h to give an orange mixture. No solid separated out. The solvent was evaporated on a rotavapor and solid residue (0.174 g) was analysed by 1H-NMR and ESI-MS. ESI-MS complied with aromatised starting compound is shown in FIG. 16.

SRC 1219b, 19 Jun. 2013.

A solution of ligand (0.150 g, 1.0 eq) and RuCl$_3$. xH$_2$O (15 mg, 0.2 eq) in methanol was refluxed at 65° C. for 16 h to give a dark brown mixture. No solid separated out. The solvent was evaporated on a rotavapor and the solid residue (0.160 g) was analysed by 1H-NMR and ESI-MS. ESI-MS complied with starting compound and methanol adduct (possibly an acetal) but it did not aromatise. (note these conditions should not promote complexation) is shown in FIG. 17.

1268, 29 Aug. 2013.

Salt not formed. 1.0 eq ligand and 0.8 eq. RuCL3.xH2O combined in methanol at reflux however this led to aromatisation and no product was observed. This suggests that the RuCl$_3$ causes aromatisation. See FIG. 18.

1271, 2 Sep. 2013.

A solution of HCl salt of ligand (0.100 g) was refluxed in methanol for 16 h. Aromatisation of starting ligand was observed by ESI-MS analysis this is show in FIG. 19.

1305(3), 3 Oct. 2013.

A solution of HCl salt of ligand (50 mg, 1.3 eq) and RuCl$_3$. xH$_2$O (1.0 eq) in methanol (3 mL) was irradiated with microwave radiation under following conditions. Power=80 W, Temperature=70° C., RAMP=2 min, Hold=20 min, Pressure=60 psi. The reaction mixture was analysed by ESI-MS analysis. ESI-MS complied with aromatised starting compound is shown in FIG. 20.

1321(2), 29 Oct. 2013.

A solution of ligand (50 mg, 1.3 eq) and RuCl$_3$. xH$_2$O (1.0 eq) in methanol (3 mL) was irradiated with microwave radiation under following conditions. Power=80 W, Temperature=65° C., RAMP=2 min, Hold=20 min, Pressure=60 psi. The reaction mixture was analysed by ESI-MS analysis. ESI-MS complied with starting compound and methanol adduct of it is shown in FIG. 21.

Stability Tests on the Non-OMe Substituted Ligand Indicated that it was More Stable:

F10-1: Ligand (below) (48 mg, 0.1 mmol) was dissolved in EtOH (5 ml), the resulting solution was refluxing under N$_2$ atmosphere for 24 h and the results were tested by $^1$H NMR.

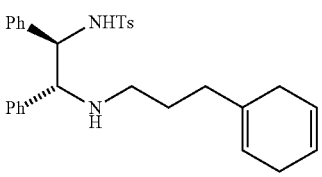

This compound is stable under refluxing in EtOH for 24 h.

F10-2: Ligand (below) (48 mg, 0.1 mmol) was dissolved in EtOH (5 ml) and HCl/Et$_2$O (0.5 ml, 1M solution) was added dropwise. Excess HCl was removed under reduced pressure and the ligand salt was dissolved in EtOH (5 ml) and refluxed under N$_2$ atmosphere for 24 h and the results were tested by $^1$H NMR.

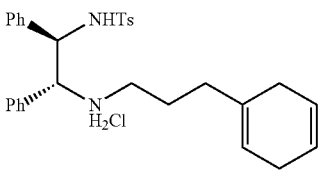

This compound is stable under refluxing in EtOH for 24 h.

F10-3: Ligand (below) (48 mg, 0.1 mmol) was dissolved in EtOH (5 ml) and HCl/Et$_2$O (0.5 ml, 1M solution) was added dropwise. Excess HCl was removed under reduced pressure and the ligand salt was dissolved in EtOH (5 ml) and RuCl$_3$XH$_2$O (28 mg, 0.1 mmol) was added. The resulting mixture was refluxed under N$_2$ atmosphere for 24 h and the results were tested by $^1$H NMR.

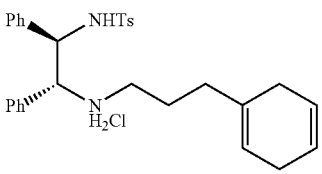

This compound formed dimer with RuCl$_3$XH$_2$O in EtOH refluxing for 24 h.

Reaction of OMecyclohexadiene Needs Large Excess of Diene:

Methoxybenzene Ruthenium(II)chloride Dimer (203).

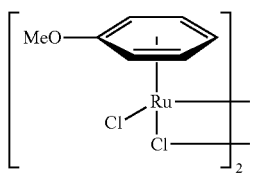

This result reflects the large excess of OMe-containing ligand that is required for formation of an electron-rich arene Ru(II) complex. No product was formed at lower loadings of diene; using 1.2 equivalents of diene, no dimer product was formed.

To a nitrogen purged flask was added RuCl$_3$.3H$_2$O (261 mg, 1 mmol) and MeOH (13.5 cm$^3$). To this was then added 1-methyl-1,4-cyclohexadiene (1.22 g, 11 mmol) and the reaction was stirred at reflux for 6 hours. The reaction solution was cooled to room temperature and filtered to give a black solid (138 mg, 0.25 mmol, 50%). $\delta_H$ (400 MHz, d$_6$-DMSO) 6.21 (2H, t, J, 6 Hz, CHAr—Ru), 5.59 (2H, d, J, 6.0 Hz, CHAr—Ru), 5.42 (1H, t J, 6.0 Hz, CHAr—Ru), 3.97 (3H, s, CH$_3$); $\delta_C$ (100 MHz, DCMSO) 140.43 (2 CAr—Ru), 94.10 (4 CHAr—Ru), 74.39 (2 CHAr—Ru), 65.19 (4 CHAr—Ru), 57.20 (2 CH$_3$).

Hexamethylbenzene cannot be reduced by the Birch reduction, which indicates that highly electron-rich aromatic rings may be unsuitable starting materials for the synthesis of tethered complexes (lit—M. A. Bennett, T.-N. Huang T. W. Matheson and A K. Smith, *Inorganic Syntheses* 1982, XXI, 74-78.

Unless otherwise stated each of the integers described in the invention may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

TABLE 1a

| Ketone | Batch number | Catalyst | Time | Conv. (%) | E.e.[a] (%) |
|---|---|---|---|---|---|
| ![ketone1] | 1 SRC946 | 4-Methoxy | 1 h | 83.3 | 96.7(R) |
| | | | 1.5 h | 92.7 | 96.8(R) |
| | | | 2 h | 99.8 | 96(R) |
| | SRC958 | 3,5-Dimethoxy | 1 h | 24 | 89.7(R) |
| | | | 2 h | 79.3 | 89.2(R) |
| | | | 3 h | 97.9 | 89.7(R) |
| | | | 4 h | 99.9 | 88.8(R) |
| ![ketone2] | 2 SRC947 | 4-Methoxy | 1.5 h | 59.6 | 96(R) |
| | | | 3.5 h | 99.9 | 96.8(R) |
| | SRC960 | 3,5-Dimethoxy | 1 h | 16.6 | 88.9(R) |
| | | | 3 h | 88.0 | 87.9(R) |
| | | | 5 h | 99.8 | 88(R) |
| ![ketone3] | 3 SRC948(1) | 4-Methoxy | 1 h | 98.6 | 95.7(R) |
| | | | 1.5 h | 99.9 | 95.5(R) |
| | SRC972 | 3,5-Dimethoxy | 5 h | 21.3 | 75.1(R) |
| | | | 8 h | 49.5 | 73.3(R) |
| | | | 23 h | 97.3 | 69.5(R) |
| | | | 31 h | 98.9 | 68.5(R) |
| ![ketone4] | 4 SRC956 | 4-Methoxy | 1 h | 64.2 | 98.1(R) |
| | | | 2 h | >99 | 98$^c$(R) |
| | SRC973 | 3,5-Dimethoxy | 1 h | 23.5 | 95.0(R) |
| | | | 2 h | 84.4 | 95.7(R) |
| | | | 3 h | 99.5 | 95.7(R) |

TABLE 1a-continued

| Ketone | | Batch number | Catalyst | Time | Conv. (%) | E.e.[a] (%) |
|---|---|---|---|---|---|---|
| 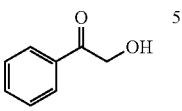 | 5 | SRC950<br>SRC963 | 4-Methoxy<br>3,5-Dimethoxy | 1 h<br>2 h<br>1 h<br>2 h | 99.1<br>99.8<br>>99<br>99.9 | 95(S)<br>97.8(S)<br>95.5(S)<br>95(S) |
| 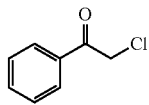 | 6 | SRC949<br>SRC962 | 4-Methoxy<br>3,5-Dimethoxy | 1 h<br>1 h<br>2 h | >99<br>88.3<br>>99 | 95[c](S)<br>94.1(S)<br>93.9(S) |
| 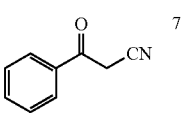 | 7 | SRC954<br>SRC967 | 4-Methoxy<br>3,5-Dimethoxy | 1 h<br>1 h<br>2 h | 99.8<br>83.4<br>>99 | 97.8(R)<br>92.2(R)<br>92.8(R) |
| 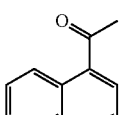 | 8 | SRC970<br>SRC969 | 4-Methoxy<br>3,5-Dimethoxy | 1 h<br>2 h<br>3 h<br>1 h<br>3 h<br>6 h<br>8 h<br>23 h<br>31 h | 48.6<br>99.3<br>99.9<br>1.7<br>31.0<br>62.2<br>63.9<br>89.5<br>96.4 | 98.9(R)<br>99.1(R)<br>99(R)<br>25.4(R)<br>17.8(R)<br>21.6(R)<br>21.3(R)<br>20.3(R)<br>20.6(R) |
| 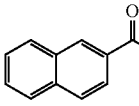 | 9 | SRC953<br>SRC966 | 4-Methoxy<br>3,5-Dimethoxy | 1 h<br>2 h<br>1 h<br>2 h<br>3 h<br>4 h | 78.6<br>99.9<br>27.3<br>85.8<br>99.4<br>99.9 | 94.8(R)<br>95[c](R)<br>89.3(R)<br>82.5(R)<br>79.6(R)<br>81.2(R)<br>86.9[c](R) |
| 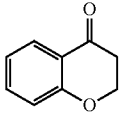 | 10 | SRC952<br>SRC965 | 4-Methoxy<br>3,5-Dimethoxy | 1 h<br>3 h<br>1 h<br>2 h<br>3 h | 42.6<br>99.9<br>77.0<br>99.7<br>99.9 | 99[b](R)<br>99[b](R) |
| 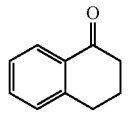 [SMILES: O=C1CCCc2ccccc21] | 11 | SRC957(1)<br>SRC964 | 4-Methoxy<br>3,5-Dimethoxy | 1 h<br>2 h<br>3 h<br>4 h<br>5 h<br>1 h<br>2 h<br>3 h<br>4 h<br>5 h | 20.5<br>67.0<br>91.8<br>98.4<br>99.5<br>22.6<br>64.3<br>91.0<br>99.1<br>99.8 | 99(R)<br>99(R) |
| 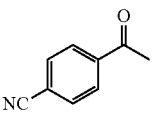 | 12 | SRC971<br>SRC968 | 4-Methoxy<br>3,5-Dimethoxy | 0.5 h<br>1 h<br>1.5 h<br>1 h<br>2 h | 37.3<br>98.1<br>99.3<br>78.2<br>99.9 | 89.8(R)<br>89.0(R)<br>88.9(R)<br>70.6(R)<br>66.5(R) |
| 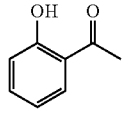 | 13 | SRC980<br>SRC981 | 4-Methoxy<br>3,5-Dimethoxy | 1 h<br>2 h<br>3 h<br>7 h | 41.3<br>93.1<br>99.8<br>99.8 | >99(R)<br>>99(R)<br>>99(R)<br>96.1(R) |
| 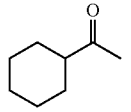 | 14 | SRC974<br>SRC975 | 4-Methoxy<br>3,5-Dimethoxy | 2 h<br>4 h<br>5 h<br>2 h<br>4 h<br>5 h<br>6 h | 75.9<br>99.2<br>99.7<br>57.4<br>95.9<br>99.2<br>99.9 | 37.4[d](S)<br>73.4[d](S) |
| 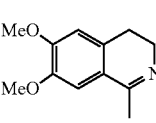 | 15 | SRC 986<br>SRC 987 | 4-Methoxy<br>3,5-Dimethoxy | 1 h<br>2 h<br>4 h<br>1 h<br>2 h | 92.3<br>98.6<br>99.5<br>95.2<br>99.3 | 35(S)<br>45.7(S)<br>50(S)<br>75.3(S)<br>75.6(S) |

[a] represents % Conv and % ee were calculated by chiral GC analysis;
[b] represents % ee was calculated by chiral HPLC analysis;
[c] indicates that for this compound % ee was given for the chiral GC analysis carried out after final work up of the reaction;
[d] represents % ee was calculated for acetate derivative.

TABLE 1b

| Catalyst | Ketone | Time | Conv. (%) | E.e. (%) |
|---|---|---|---|---|
| 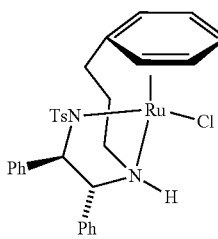 | 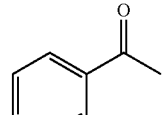 | 4.5 h | >99% | 97.4% (R) |
| | 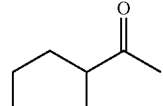 | 22 h | >99% | 41% (R) |

TABLE 1b-continued

| Catalyst | Ketone | Time | Conv. (%) | E.e. (%) | |
|---|---|---|---|---|---|
| [3,5-(MeO)₂-C₆H₃ tethered TsDPEN-Ru-Cl catalyst] | acetophenone | 8 h | 99.1% | 91.2% | (R) |
| | cyclohexyl methyl ketone | 21.5 h | 99% | 74% | (R) |
| [4-iPr-C₆H₄ tethered TsDPEN-Ru-Cl catalyst] | acetophenone | 22 h | 99.9% | 97.4% | (R) |
| | cyclohexyl methyl ketone | 20 h | 99% | 31% | (R) |
| [4-tBu-C₆H₄ tethered TsDPEN-Ru-Cl catalyst] | acetophenone | 94 h | 54.8% | 87.4% | (R) (S) |
| | cyclohexyl methyl ketone | 44 h | 29.7% | 4% | |
| [4-Ph-C₆H₄ tethered TsDPEN-Ru-Cl catalyst] | acetophenone | 23 h | 99.9% | 96.1% | (R) |
| | cyclohexyl methyl ketone | 44 h | 99% | 60% | (R) |

TABLE 2a

| Catalyst | S/C | solvent | Temp. (°C.) | Pressure (bar) | Time | Conv (%) | E.e. (%) | Ref. | Substrate |
|---|---|---|---|---|---|---|---|---|---|
| (structure: tethered Ru catalyst with benzene ring, TsN, Ru-Cl, NH, Ph, Ph) | 500/1 | MeOH [S] 0.5M | 60 | 30 | 16 | 99.8 | 96.7 (R) | Adv Synth & Catal, 2012, Wills* | Ph-C(O)-Me |
| (structure: tethered Ru catalyst with 3,5-dimethoxybenzene, TsN, Ru-Cl, NH, Ph, Ph) | 500/1 | MeOH [S] 0.5M | 60 | 30 | 16 | 99.9 | 94.0 (R) | | Ph-C(O)-Me |
| (structure: tethered Ru catalyst with 2,5-dimethoxybenzene, TsN, Ru-Cl, NH, Ph, Ph) | 500/1 | MeOH [S] 0.5M | 60 | 30 | 16 | 99.8 | 83.5 | | Ph-C(O)-Me |

***'Application of Tethered Ruthenium Catalysts to Asymmetric Hydrogenation of ketones, and the Selective Hydrogenation of Aldehydes', Katherine E. Jolley, Antonio Zanotti-Gerosa, Fred Hancock, Alan Dyke, Damian M. Grainger, Jonathan A. Medlock, Hans G. Nedden, Jacques J. M. Le Paih, Stephen J. Roseblade, A. Seger, V. Sivakumar, David J Morris and Martin Wills, *Adv. Synth. Catal.* 2012, 354, 2545-2555.

TABLE 2b

| Catalyst | S/C | solvent | Temp. (°C.) | Pressure (bar) | Time | Conv (%) | E.e. (%) | Ref. | Substrate |
|---|---|---|---|---|---|---|---|---|---|
| (structure: tethered Ru catalyst with benzene, TsN, Ru-Cl, NH, Ph, Ph) | 500/1 | MeOH [S] 0.5M | 60 | 30 | 24 | 99.9 | 99.0 (R) | Adv Synth & Catal, 2012, Wills* | chroman-4-one |
| (structure: tethered Ru catalyst with OMe-substituted benzene, TsN, Ru-Cl, NH, Ph, Ph) | 500/1 | MeOH [S] 0.5M | 60 | 30 | 24 | 97.6 | 99.6 (R) | | chroman-4-one |

TABLE 2b-continued

| Catalyst | S/C | solvent | Temp. (° C.) | Pressure (bar) | Time | Conv (%) | E.e. (%) | Ref. | Substrate |
|---|---|---|---|---|---|---|---|---|---|
| 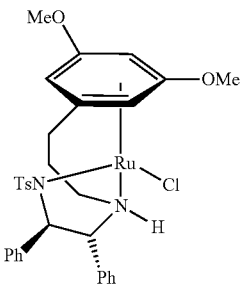 | 500/1 | MeOH [S] 0.5M | 60 | 30 | 24 | 99.9 | 98.8 (R) | | 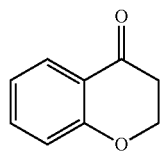 |

*'Application of Tethered Ruthenium Catalysts to Asymmetric Hydrogenation of ketones, and the Selective Hydrogenation of Aldehydes', Katherine E. Jolley, Antonio Zanotti-Gerosa Fred Hancock, Alan Dyke, Damian M. Grainger, Jonathan A. Medlock, Hans G. Nedden, Jacques J. M. Le Paih, Stephen J. Roseblade, A. Seger, V. Sivakumar, David J Morris and Martin Wills, *Adv. Synth. Catal.* 2012, 354, 2545-2555.

TABLE 2c

| Catalyst | S/C | solvent | Temp. (° C.) | Pressure (bar) | Time | Conv (%) | Ee (%) | Ref. | Substrate |
|---|---|---|---|---|---|---|---|---|---|
| 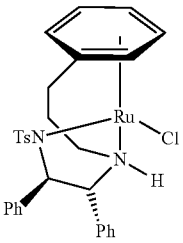 | 500/1 | MeOH [S] 0.5M | 60 | 30 | 48 | 99.5 | 97.5 (R) | Adv Synth & Catal, 2012, Wills* | 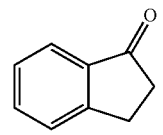 |
| 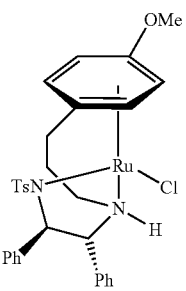 | 500/1 | MeOH [S] 0.5M | 60 | 30 | 48 | 91.9 | 97.7 (R) | | 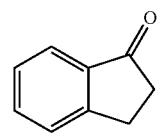 |
| 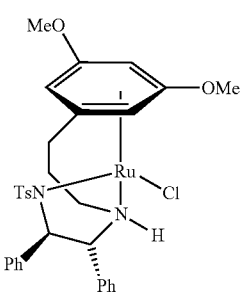 | 500/1 | MeOH [S] 0.5M | 60 | 30 | 48 | 71.7 | 95.2 (R) | | 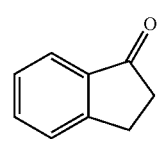 |

*'Application of Tethered Ruthenium Catalysts to Asymmetric Hydrogenation of ketones, and the Selective Hydrogenation of Aldehydes', Katherine E. Jolley, Antonio Zanotti-Gerosa Fred Hancock, Alan Dyke, Damian M. Grainger, Jonathan A. Medlock, Hans G. Nedden, Jacques J. M. Le Paih, Stephen J. Roseblade, A. Seger, V. Sivakumar, David J Morris and Martin Wills, *Adv. Synth. Catal.* 2012, 354, 2545-2555.

TABLE 2d

| Catalyst | S/C | solvent | Temp. (°C.) | Pressure (bar) | Time | Conv (%) | E.e. (%) | Ref. | Substrate |
|---|---|---|---|---|---|---|---|---|---|
| 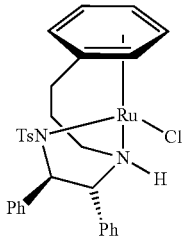 | 500/1 | MeOH [S] 0.5M | 60 | 30 | 48 | 99.9 | 99.3 (R) | Adv Synth & Catal, 2012, Wills* | 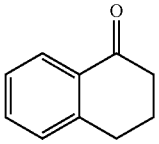 [SMILES: O=C1CCCc2ccccc21] |
| 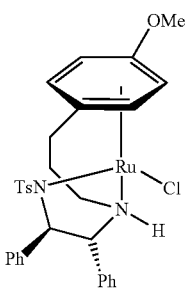 | 500/1 | MeOH [S] 0.5M | 60 | 30 | 48 | 99.5 | 98.6 (R) | | 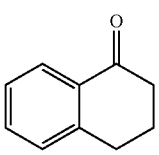 [SMILES: O=C1CCCc2ccccc21] |
| 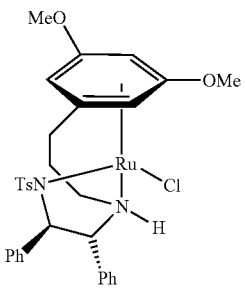 | 500/1 | MeOH [S] 0.5M | 60 | 30 | 48 | 59.7 | 98.6 (R) | | 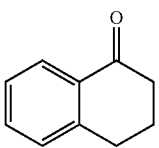 [SMILES: O=C1CCCc2ccccc21] |

* 'Application of Tethered Ruthenium Catalysts to Asymmetric Hydrogenation of ketones, and the Selective Hydrogenation of Aldehydes', Katherine E. Jolley, Antonio Zanotti-Gerosa Fred Hancock, Alan Dyke, Damian M. Grainger, Jonathan A. Medlock, Hans G. Nedden, Jacques J. M. Le Paih, Stephen J. Roseblade, A. Seger, V. Sivakumar, David J Morris and Martin Wills, *Adv. Synth. Catal.* 2012, 354, 2545-2555.

TABLE 2e

| Catalyst | S/C | solvent | Temp. (°C.) | Pressure (bar) | Time | Conv (%) | E.e. (%) | Ref. | Substrate |
|---|---|---|---|---|---|---|---|---|---|
| 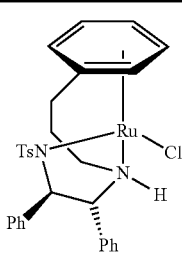 | 500/1 | MeOH [S] 0.5M | 60 | 30 | 24 | >99 | >99 (S) | Adv Synth & Catal, 2012, Wills* | 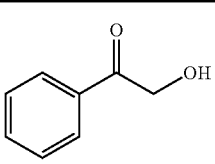 |

TABLE 2e-continued

| Catalyst | S/C | solvent | Temp. (°C.) | Pressure (bar) | Time | Conv (%) | E.e. (%) | Ref. | Substrate |
|---|---|---|---|---|---|---|---|---|---|
| (Ru complex with OMe-aryl tether, TsN, Ph, Ph, Cl) | 500/1 | MeOH [S] 0.5M | 60 | 30 | 24 | 99.7 | 90.7 (S) | | phenacyl alcohol (PhC(O)CH₂OH) |
| (Ru complex with 2,5-diOMe-aryl tether, TsN, Ph, Ph, Cl) | 500/1 | MeOH [S] 0.5M | 60 | 30 | 24 | 94.2 | 87.8 (S) | | phenacyl alcohol (PhC(O)CH₂OH) |

*'Application of Tethered Ruthenium Catalysts to Asymmetric Hydrogenation of ketones, and the Selective Hydrogenation of Aldehydes', Katherine E. Jolley, Antonio Zanotti-Gerosa Fred Hancock, Alan Dyke, Damian J. M. Grainger, Jonathan A. Medlock, Hans G. Nedden, Jacques J. M. Le Paih, Stephen J. Roseblade, A. Seger, V. Sivakumar, David J Morris and Martin Wills, *Adv. Synth. Catal.* 2012, 354, 2545-2555.

TABLE 3a

MeOH solvent with [S] 0.5M, 60° C., S/C 500/1, 30 bar H₂

Catalyst: (Ru complex with aryl tether, TsN, Ph, Ph, Cl, NH)

| Ketone | Time (hr.) | Conv. (%) | E.e. (%) |
|---|---|---|---|
| acetophenone (PhC(O)Me) | 16 | 99.8 | 96.7 (R) |
| cyclohexyl methyl ketone | 48 | >99.9 | 66.8 (S) |
| 4-methoxyacetophenone (4-MeO-C₆H₄-C(O)Me) | 16 | 99.3 | 91.1 (R) |

TABLE 3a-continued

MeOH solvent with [S] 0.5M, 60° C., S/C 500/1, 30 bar H₂

Catalyst: (Ru complex with aryl tether, TsN, Ph, Ph, Cl, NH)

| Ketone | Time (hr.) | Conv. (%) | E.e. (%) |
|---|---|---|---|
| 4-trifluoromethylacetophenone (4-F₃C-C₆H₄-C(O)Me) | 16 | >99.9 | 88.2 (R) |
| 3,5-bis(trifluoromethyl)acetophenone | 24 | >99 | 70.0 (R) |
| propiophenone (PhC(O)Et) | 16 | 98.3 | 90.4 (R) |

TABLE 3a-continued
MeOH solvent with [S] 0.5M, 60° C., S/C 500/1, 30 bar H$_2$
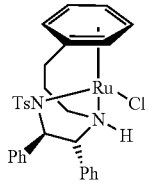
| Ketone | Catalyst Time (hr.) | Conv. (%) | E.e. (%) |
|---|---|---|---|
| 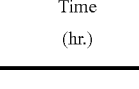 | 48 | 73.7 | 68.8 (R) |
| 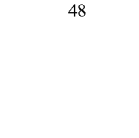 | 24 | 99.9 | 84.4 (S) |
|  | 24 | >99 | >99 (S) |
|  | 48 | 99.5 | 97.5 (R) |
| 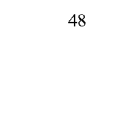 | 48 | 99.9 | 99.3 (R) |
|  | 24 | 99.9 | 99.0 (R) |
TABLE 3b
MeOH solvent with [S] 0.5M, 60° C., S/C 500/1, 30 bar H$_2$
 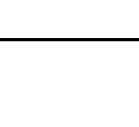
| Ketone | Time (hr.) | Conv. (%) | E.e. (%) | Time (hr.) | Conv. (%) | E.e. (%) |
|---|---|---|---|---|---|---|
| 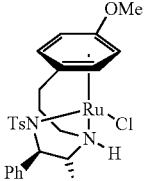 | 16 | 99.9 | 94.0 (R) | 16 | 99.8 | 83.5 (R) |
| 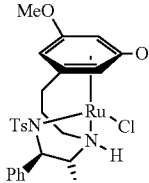 | 48 | 99.3 | 37.1 (S) | 48 | 54.6 | 80.3 (S) |
| 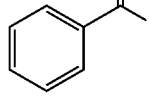 | 16 | 99.9 | 93.9 (R) | 16 | 99.9 | 79.5 (R) |
| 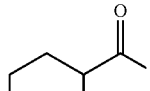 | 16 | 99.4 | 92.1 (R) | 16 | 99.2 | 73.5 (R) |
| 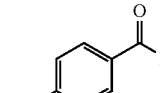 | 24 | >99.0 | 82.0 (R) | 24 | >99.9 | 53.6 (R) |
| 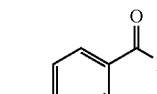 | 16 | 69.6 | 84.3 (R) | 16 | 18.8 | 72.8 (R) |
| 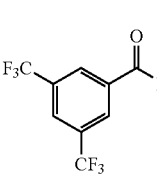 | 48 | 36.4 | 83.3 (R) | 48 | 26.8 | 77.6 (R) |
| 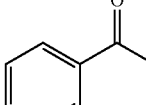 | 24 | >99.0 | 94.5 (S) | 24 | 99.9 | 80.7 (S) |
| 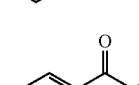 | 24 | 99.7 | 90.7 (S) | 24 | 94.2 | 87.8 (S) |

TABLE 3b-continued
MeOH solvent with [S] 0.5M, 60° C., S/C 500/1, 30 bar H$_2$
| Ketone | 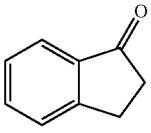 | | | 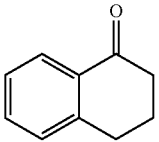 [SMILES: O=C1CCCc2ccccc21] | | |
|---|---|---|---|---|---|---|
| | Time (hr.) | Conv. (%) | E.e. (%) | Time (hr.) | Conv. (%) | E.e. (%) |
| 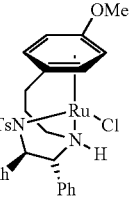 | 48 | 91.9 | 97.7 (R) | 48 | 71.7 | 95.2 (R) |
| 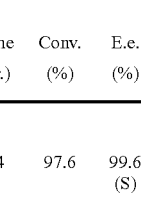 | 48 | 99.5 | 98.6 (R) | 48 | 59.7 | 98.6 (R) |
TABLE 3b-continued
MeOH solvent with [S] 0.5M, 60° C., S/C 500/1, 30 bar H$_2$
| Ketone | 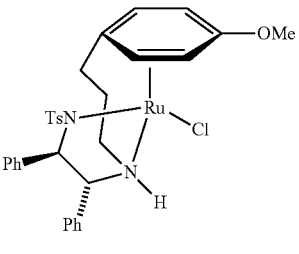 | | | 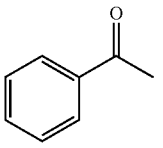 | | |
|---|---|---|---|---|---|---|
| | Time (hr.) | Conv. (%) | E.e. (%) | Time (hr.) | Conv. (%) | E.e. (%) |
| 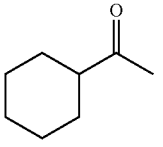 | 24 | 97.6 | 99.6 (S) | 24 | 99.9 | 98.8 (S) |
TABLE 4
| Catalyst | Ketone | Time | % Conv | % ee |
|---|---|---|---|---|
| 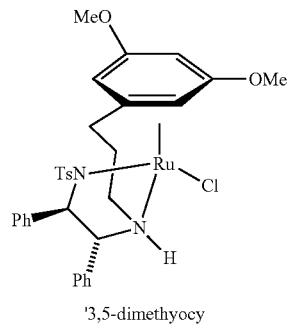<br>'4-methoxy' | 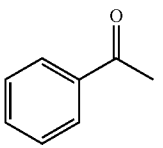 | 4.5 h | >99% | 97.4%(R) |
| | 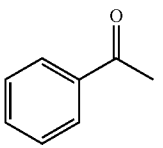 | 22 h | >99% | 41%(R) |
| 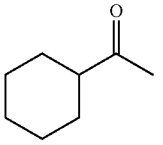<br>'3,5-dimethyocy' | 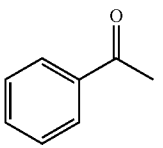 | 8 h | 99.1% | 91.2%(R) |
| | 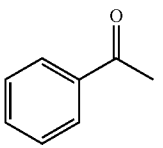 | 21.5 h | 99% | 74%(R) |

TABLE 4-continued

| Catalyst | Ketone | Time | % Conv | % ee |
|---|---|---|---|---|
| '4-isopropyl' | acetophenone | 22 h | 99.9% | 97.4%(R) |
| | cyclohexyl methyl ketone | 20 h | 99% | 31%(R) |
| '4-tertbutyl' | acetophenone | 94 h | 54.8% | 87.4%(R) |
| | cyclohexyl methyl ketone | 44 h | 29.7% | 4%(S) |
| '4-phenyl' | acetophenone | 23 h | 99.9% | 96.1%(R) |
| | cyclohexyl methyl ketone | 44 h | 99% | 60%(R) |
| 'I OMe' | acetophenone | 7 h | 99.8% | 96.6%(R) |
| 'Alkyne 4-OMe' | acetophenone | 22 h | 99.8% | 96.4%(R) |

TABLE 4-continued

| Catalyst | Ketone | Time | % Conv | % ee |
|---|---|---|---|---|
| 4-OMe TEG (R = O(CH₂CH₂O)₂CH₂CH₃; sulfonamide Ru catalyst with p-methoxy tethered arene, diphenyl-ethylenediamine) | acetophenone | 4 h | >99.8% | 96.5%(R) |
| Achiral Bn (Ru catalyst with biphenyl tethered arene, Ts-ethylenediamine) | acetophenone | 24.5 h | 100% | n/a |

TABLE 5

Catalysts: 4-methoxy, 3,5-dimethyoxy, TEG 4-OMe (R = O(CH₂CH₂O)₂CH₂CH₃), 3C-teth

| reaction no | Catalyst | S/C | Solvent | Temp | Time | % Conv | % ee |
|---|---|---|---|---|---|---|---|
| SRC 1177 | 4-Methoxy | 100 | H₂O | 60° C. | 1 h | 77 | 98(R) |
|  |  |  |  |  | 2 h | >99 | 97(R) |
| SRC 1197 | 4-Methoxy | 500 | H₂O | 60° C. | 1 h | 12 | 96(R) |
|  |  |  |  |  | 3 h | 20 | 96(R) |
|  |  |  |  |  | 7 h | 24 | 96(R) |
|  |  |  |  |  | 22 h | 26 | 96(R) |
| SRC 1193 | 3,5-dimethoxy | 100 | H₂O | 60° C. | 2 h | >99 | 77(R) |
| SRC 1195 | 3,5-dimethoxy | 500 | H₂O | 60° C. | 1 h | 35 | 86(R) |
|  |  |  |  |  | 3 h | 82 | 82(R) |
|  |  |  |  |  | 5 h | 99 | 81(R) |
| SRC 1177 | 4-Methoxy | 100 | H₂O | 40° C. | 1 h | 32 | 98(R) |
|  |  |  |  |  | 2 h | 53 | 98(R) |
|  |  |  |  |  | 4 h | 84 | 98(R) |
|  |  |  |  |  | 5 h | 97 | 98(R) |
| SRC 1309 | TEG 4-OMe | 100 | H₂O | 60° C. | 1 h | 99 | 97(R) |
| SRC 1198b | 4-Methoxy | 500 | H₂O:MeOH (1:1) | 60° C. | 1 h | 35 | 97(R) |
|  |  |  |  |  | 2 h | 58 | 97(R) |
|  |  |  |  |  | 4 h | 81 | 97(R) |

TABLE 5-continued

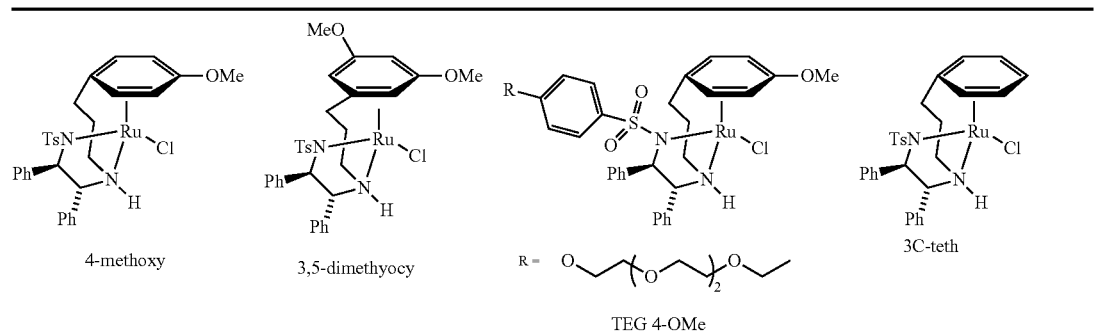

4-methoxy    3,5-dimethyocy    TEG 4-OMe    3C-teth

R = O~~O~~O~

| reaction no | Catalyst | S/C | Solvent | Temp | Time | % Conv | % ee |
|---|---|---|---|---|---|---|---|
| SRC 1200b | 4-Methoxy | 500 | H₂O:MeOH (1:1) | 60° C. | 1 h | 35 | 97(R) |
|  |  |  |  |  | 3 h | 74 | 97(R) |
|  |  |  |  |  | 4 h | 88 | 97(R) |
|  |  |  |  |  | 5 h | 98 | 97(R) |
|  |  |  |  |  | 6 h | 99 | 97(R) |
| SRC 1198c | 3,5-dimethoxy | 500 | H₂O:MeOH (1:1) | 60° C. | 1 h | 96 | 85(R) |
|  |  |  |  |  | 1.5 h | 99 | 85(R) |
| SRC 1224b | TEG 4-OMe | 100 | H₂O:MeOH | 60° C. | 1 h | 95 | 97(R) |
|  |  |  |  |  | 2 h | 99 | 97(R) |
| SRC 1225a | TEG 4-OMe | 500 | H₂O:MeOH (1:1) | 60° C. | 3 h | 33 | 97(R) |
|  |  |  |  |  | 25.5 h | 88 | 96(R) |
| SRC 1201b | 3,5-dimethoxy | 500 | H₂O:MeOH (1:0.5) | 60° C. | 1 h | 67 | 86(R) |
|  |  |  |  |  | 2 h | 99 | 86(R) |
| SRC 1201a | 3C-teth | 500 | H₂O:MeOH (1:0.5) | 60° C. | 2 h | 4 | 92(S) |
|  |  |  |  |  | 4 h | 7 | 93(S) |
|  |  |  |  |  | 7.5 h | 12 | 94(S) |
|  |  |  |  |  | 23 h | 23 | 94(S) |
| SRC 1203b | 4-Methoxy | 500 | H₂O:MeOH (1:1) | 60° C. | 1 h | 41 | 97(R) |
|  |  |  |  |  | 2 h | 73 | 97(R) |
|  |  |  |  |  | 4 h | 99 | 97(R) |
| SRC 1203c | 3,5-dimethoxy | 500 | H₂O:MeOH (1:1) | 60° C. | 1 h | 55 | 85(R) |
|  |  |  |  |  | 2 h | 92 | 85(R) |
|  |  |  |  |  | 3 h | 99 | 85(R) |
| SRC 1230a | 4-Methoxy | 100 | HCOONH₄ H₂O | 60° C. | 1 h | 11 | 97(R) |
|  |  |  |  |  | 3.5 h | 20 | 98(R) |
|  |  |  |  |  | 6.5 h | 25 | 98(R) |
|  |  |  |  |  | 22.5 h | 56 | 98(R) |
| SRC 1230b | 4-Methoxy | 100 | H₂O | 60° C. | 1 h | 31 | 97(R) |
|  |  |  |  |  | 3.5 h | 48 | 97(R) |
|  |  |  |  |  | 6.5 h | 54 | 97(R) |
|  |  |  |  |  | 22.5 h | 57 | 97(R) |
| SRC 1234(1) | 4-Methoxy * | 100 | H₂O | 60° C. | 1 h | 99 | 98(R) |
| SRC 1234(2) |  |  | HCOOH | 60° C. | 1 h | 40 | 98(R) |
|  |  |  |  |  | 2 h | 60 | 97(R) |
|  |  |  |  |  | 3.5 h | 99 | 97(R) |
| SRC 1234(3) |  |  | HCOOH | 60° C. | 1 h | 26 | 97(R) |
|  |  |  |  |  | 2.5 h | 52 | 97(R) |
|  |  |  |  |  | 15 h | 57 | 97(R) |
|  |  |  |  |  | rt | 67 | 97(R) |
|  |  |  |  |  | 5 h | 76 | 97(R) |
|  |  |  |  |  | 9.5 h |  |  |

* n-Hexane (3 × 2 mL) was used to extract product after each cycle from reaction mixture. 1 mol of HCOOH was added to regenerate HCOONa.

| SRC 1235(1) | 4-Methoxy * | 100 | H₂O | 60° C. | 1 h | 99 | 97(R) |
|---|---|---|---|---|---|---|---|
| SRC 1235(2) |  |  | HCOOH | 60° C. | 1 h | 99 | 98(R) |
|  |  |  |  |  | 1 h | 85 | 97(R) |
| SRC 1235(3) |  |  | HCOOH | 60° C. |  |  |  |
|  |  |  |  |  | 1.5 h | 99 | 98(R) |
| SRC 1235(4) |  |  | HCOOH | 60° C. | 1 h | 34 | 96(R) |
|  |  |  |  |  | 2 h | 64 | 96(R) |
|  |  |  |  |  | 15 hrt | 68 | 96(R) |
|  |  |  |  |  | 4 h | 83 | 97(R) |
|  |  |  |  |  | 6 h | 90 | 97(R) |
|  |  |  |  |  | 8 h | 93 | 97(R) |

* n-Pentane (3 × 2 mL) was used to extract product after each cycle from reaction mixture. 1 mol of HCOOH was added to regenerate HCOONa.

| SRC 1236(1) | 4-Methoxy * | 100 | H₂O | 60° C. | 1 h | 99 | 98(R) |
|---|---|---|---|---|---|---|---|
| SRC 1236(2) |  |  | HCOOH | 60° C. | 1 h | 88 | 96(R) |
| SRC 1236(3) |  |  | HCOOH | 60° C. | 1.5 h | 99 | 96(R) |
|  |  |  |  |  | 1 h | 20 | 96(R) |
|  |  |  |  |  | 4 h | 80 | 97(R) |

TABLE 5-continued

Catalyst structures (left to right): 4-methoxy, 3,5-dimethyocy, TEG 4-OMe (R = O−(CH₂CH₂O)₂−Et, i.e., $R = O{-}(CH_2CH_2O)_2{-}Et$), 3C-teth

| reaction no | Catalyst | S/C | Solvent | Temp | Time | % Conv | % ee |
|---|---|---|---|---|---|---|---|
| | | | | | 17 hrt | 88 | 97(R) |
| | | | | | 5 h | 91 | 97(R) |
| | | | | | 7 h | 94 | 97(R) |
| | | | | | 9 h | 96 | 97(R) |
| | * Pet. ether (3 × 2 mL) was used to extract product after each cycle from reaction mixture. 1 mol of HCOOH was added to regenerate HCOONa. | | | | | | |
| SRC 1237(1) | 4-Methoxy * | 100 | H₂O | 60° C. | 1 h | 99 | 97(R) |
| SRC 1237(2) | | | HCOOH | 60° C. | 1 h | 99 | 97(R) |
| SRC 1237(3) | | | HCOOH | 60° C. | 1 h | 93 | 97(R) |
| | | | | | 1.5 h | 99 | 97(R) |
| 15 h rt | | | HCOOH | 60° C. | 1 h | 23 | 95(R) |
| SRC 1237(4) | | | | | 2.5 h | 53 | 95(R) |
| | | | | | 4.5 h | 85 | 96(R) |
| | | | | | 6.5 h | 97 | 96(R) |

* n-Pentane (3 × 2 mL) was used to extract product after each cycle from reaction mixture. 1 mol of HCOOH was added to regenerate HCOONa.

TABLE 6

| Substrate | Batch no | Catalyst | S/C | Solvent | Temp | Time | % Conv | % ee |
|---|---|---|---|---|---|---|---|---|
| acetophenone | 1 SRC 1237 | 4-Methoxy | 100 | H₂O | 60° C. | 1 h | 99 | 97(R) |
| | SRC 1193 | 3,5-dimethoxy | 100 | H₂O | 60° C. | 2 h | >99 | 77(R) |
| | | | 100 | H₂O | 60° C. | 1 h | 99 | 88(R) |
| | | 3C-tech | 100 | H₂O | 60° C. | 1 h | 99 | 97(R) |
| | SRC 1244 SRC 1309 SRC 1295 | TEG 4-OMe Cationic complex | 100 | H₂O | 60° C. | 26 h | 78 | 43(S) |
| cyclohexyl methyl ketone | 2 SRC 1194 | 3,5-dimethoxy | 100 | H₂O | 60° C. | 2 h | 99 | 85(S) |
| | | | 500 | H₂O | 60° C. | 1 h | 22 | 85(S) |
| | SRC 1196 | 3,5-dimethoxy | | | | 3 h | 73 | |
| | | | | | | 5 h | 99 | |
| propiophenone | 3 SRC 1240 | 4-Methoxy | 100 | H₂O | 60° C. | 1 h | 88 | 98(R) |
| | | | | | | 1.5 h | 99 | 98(R) |
| α-tetralone | 4 SRC 1241 | 4-Methoxy | 100 | H₂O | 60° C. | 1 h | 36 | 97(R) |
| | | | | | | 3 h | 74 | |
| | | | | | | 5 h | 93 | |
| | | | | | | 7 h | 98 | |

TABLE 6-continued

| Substrate | | Batch no | Catalyst | S/C | Solvent | Temp | Time | % Conv | % ee |
|---|---|---|---|---|---|---|---|---|---|
| 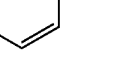 | 5 | SRC 1243 | 4-Methoxy | 100 | H₂O | 60° C. | 1 h<br>1.5 h<br>2 h | 72<br>98<br>99 | 95(R)<br>95(R)<br>95(R) |
| 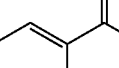 | 6 | SRC 1242 | 4-Methoxy | 100 | H₂O | 60° C. | 1 h<br>2 h<br>2.5 h<br>3 h | 53<br>97<br>98<br>99 | 98(R)<br>97(R)<br>97(R)<br>97(R) |
| 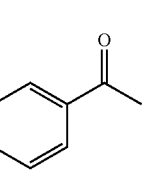 | 7 | SRC 1245 | 4-Methoxy | 100 | H₂O | 60° C. | 1 h<br>2 h | 96<br>96 | 98(R)<br>97(R) |
| 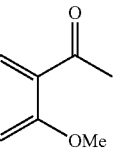 | 8 | SRC 1246 | 4-Methoxy | 100 | H₂O | 60° C. | 1 h<br>2 h | 65<br>99 | 96(R)<br>95(R) |
| 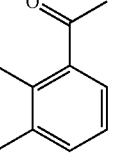 | 9 | SRC 1247 | 4-Methoxy | 100 | H₂O | 60° C. | 1 h<br>3 h | 36<br>99 | 99(R)<br>99(R) |
| 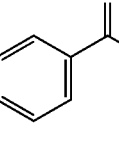 | 10 | SRC 1248 | 4-Methoxy | 100 | H₂O | 60° C. | 1 h<br>3 h | 35<br>99 | 97(R)<br>96(R) |
| 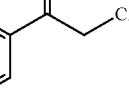 | 11 | SRC 1249 | 4-Methoxy | 100 | H₂O | 60° C. | 1 h | 99 | 96(R) |
| 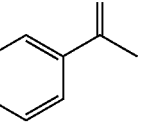 | 12 | SRC 1250 | 4-Methoxy | 100 | H₂O | 60° C. | 1 h<br>1.5 h | 85<br>99 | 94(R)<br>94(R) |
| 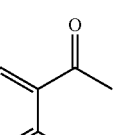 | 13 | SRC 1251 | 4-Methoxy | 100 | H₂O | 60° C. | 1 h<br>2 h<br>2.5 h | 81<br>99<br>99 | 71(R)<br>69(R)<br>69(R) |

TABLE 6-continued

| Substrate | Batch no | Catalyst | S/C | Solvent | Temp | Time | % Conv | % ee |
|---|---|---|---|---|---|---|---|---|
| 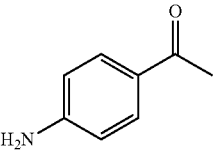 | 14 SRC 1261<br>SRC 1256<br>SRC 1267 | 4-Methoxy<br>3C-teth<br>(S,S)<br>Noyori's<br>catalyst p-<br>Cymene | 100<br>100<br>100 | H₂O:<br>MeOH<br>H₂O:<br>MeOH<br>H₂O:<br>MeOH | 60° C.<br>60° C.<br>60° C. | 4.5 h<br>4.5 h<br>15.5 h | 99<br>99<br>78 | 94(R)<br>94(S)<br>91(R) |
| 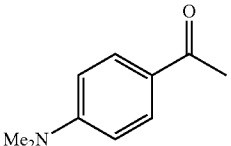 | 15 SRC 1258 | 4-Methoxy | 100 | H₂O:<br>MeOH | 60° C. | 4 h | 97 | 91(R) |

TABLE 7

| Substrate | Batch no | Catalyst | S/C | Solvent | Temp | Time | % Conv | % ee |
|---|---|---|---|---|---|---|---|---|
| 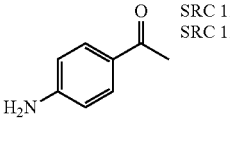 | SRC 1252<br>SRC 1254 | 4-Methoxy | 100 | H₂O:<br>MeOH | 60° C. | 4.5 h | ~98 | |
| 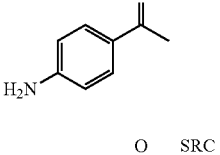 | SRC 1253 | 4-Methoxy | 1000 | FA:<br>TEA | 60° C. | 24 h | NR | |
| 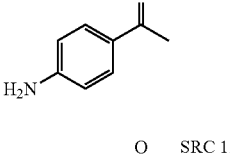 | SRC 1256 | 3C-teth<br>(S,S) | 100 | H₂O:<br>MeOH | 60° C. | 4.5 h | 99 | 94(S) |
| 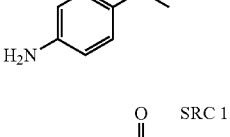 | SRC 1261 | 4-Methoxy | 100 | H₂O:<br>MeOH | 60° C. | 4.5 h | 99 | 94(R) |
| 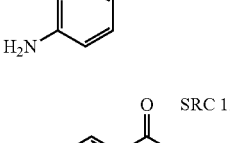 | SRC 1267 | Noyori's<br>catalyst<br>p-<br>Cymene | 100 | H₂O:<br>MeOH | 60° C. | 15.5 h | 78 | 91(R) |
| 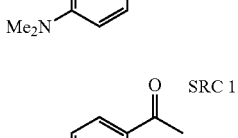 | SRC 1258 | 4-Methoxy | 100 | H₂O:<br>MeOH | 60° C. | 4 h | 97 | 91(R) |
| 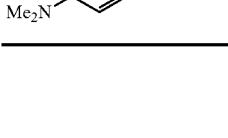 | SRC 1260 | 3C-teth<br>(S,S) | 250 | FA:<br>TEA | 45° C. | 6 h | 93 | 91(S) |

TABLE 8

Polymer supported catalyst reducing agent, S/C 100/1, 24 hours (acetophenone → 1-phenylethanol)

| Entry | Catalyst | $H_2$ source | Temp. (° C.) | Conv. (%)[a] | Ee. (%)[a,b] |
|---|---|---|---|---|---|
| 1 | A | Formic acid:$Et_3N$ 5:2 | 28° C. | 1.3 | ND |
| 2 | A | IPA/KOH | 28° C. | 0.4 | ND |
| 3 | A | Water/sodium formate | 60° C. | 6.5 | 68.3 (R) |
| 4 | B | Formic acid:$Et_3N$ 5:2 | 28° C. | 0.61 | ND |
| 5 | B | IPA/KOH | 28° C. | 0.71 | ND |
| 6 | B | Water/sodium formate | 60° C. | 32.0 | 92.7 (R) |
| 7 | Recovered B from entry 6 | Water/sodium formate | 60° C. | 4.3 | Only 1 enantiomer seen by GC |
| 8 | B | $H_2$, MeOH | 60° C. | 13.1 | Racemic |
| 9 | C | Water/sodium formate | 60° C. | 16.2 | 50.2 (R) |
| 10 | C | $H_2$, MeOH | 60° C. | 34.5 | Racemic |
| 11 | D | Formic acid:$Et_3N$ 5:2 | 28° C. | 6.9 | 93.0 (R) |
| 12 | D | IPA/KOH | 28° C. | 0.45 | ND |
| 13 | D | Water/sodium formate | 60° C. | 26.3 | 37.9 (R) |
| 14 | D | $H_2$, MeOH | 60° C. | 79.4 | 2.7 (R) |

[a]Determined by GC analysis.
[b]For conversions less than 2% the ee. was not determined.

TABLE 9

Polymer supported catalyst reducing agent, S/C 100/1, 24 hours (acetophenone → 1-phenylethanol)

| Entry | Catalyst | $H_2$ source | Temp. (° C.) | Conv. (%)[a] | Ee. (%)[a] |
|---|---|---|---|---|---|
| 1 | B | Formic acid: $Et_3N$ 5:2 | 60° C. | 10.8 | 87.0 (R) |
| 2 | B | IPA/KOH | 80° C. | 11.3 | 2.8 (R) |
| 3 | C | Formic acid: $Et_3N$ 5:2 | 60° C. | 17.9 | 82.7 (R) |
| 4 | C | IPA/KOH | 80° C. | 35.2 | Racemic |
| 5 | D | Formic acid: $Et_3N$ 5:2 | 60° C. | 5.6 | 82.8 (R) |
| 6 | D | IPA/KOH | 80° C. | 4.6 | 14.4 (R) |

[a]Determined by GC analysis.

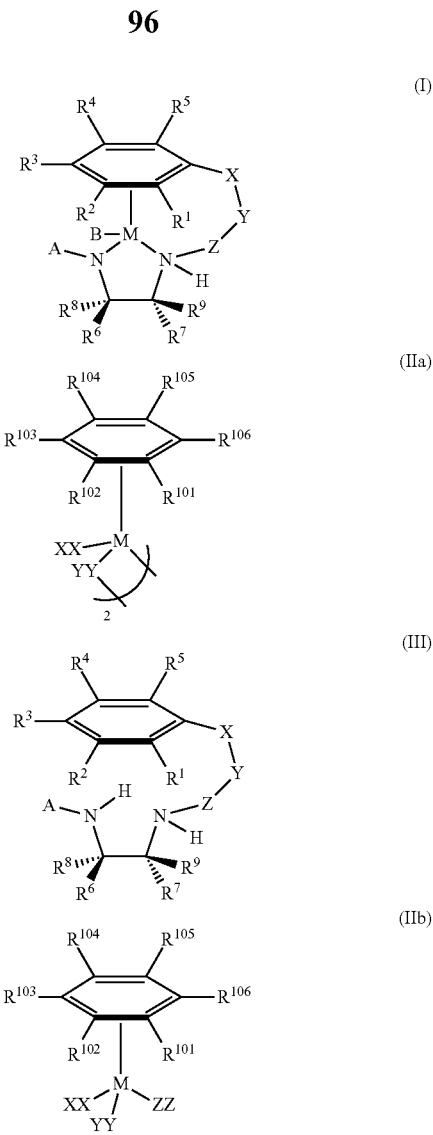

The invention claimed is:

1. A process for preparing a compound of formula (I), the process comprising the step of reacting a compound of formula (IIa) or (IIb) with the compound of formula (III)

or a salt thereof; wherein $R^1$-$R^5$, $R^6$-$R^9$ and $R^{101}$-$R^{106}$ are each independently, or in combination with another of said substituents $R^1$-$R^5$, $R^6$-$R^9$ and $R^{101}$-$R^{106}$, selected from the group consisting of H, halide, alkyl, alkenyl, alkynyl, alkoxy, hydroalkyl, carboalkyl, haloalkyl, aryl, aryloxy, arylmethyl, acyl, carboxy, alkoxycarbonyl, thiocarbonyl, cyano, hydroxyl, thiol, alkylthiol, amino, acylated amino, $NO_2$, silyl, and $SO_2R^{10}$, where $R^{10}$ is independently selected in each instance from the group consisting of H, halide, alkyl, alkenyl, alkynyl, alkoxy, hydroalkyl, carboalkyl, haloalkyl, aryl, aryloxy, arylmethyl, acyl, carboxy, alkoxycarbonyl, thiocarbonyl, cyano, hydroxyl, thiol, alkylthiol, amino, acylated amino, $NO_2$, and silyl;

A is selected from the group consisting of H, $R^{11}$, $SO_2R^{11}$, $SO_2NR^{11}R^{12}$, $SOR^{11}$ $P(O)(R^{11}R^{12})$, $P(O)(OR^{11})(OR^{12})$, and $CO_2R^{11}$, where $R^{11}$ and $R^{12}$ are each independently selected in each instance from the group consisting of H, halide, alkyl, alkenyl, alkynyl, alkoxy, hydroalkyl, carboalkyl, haloalkyl, aryl, aryloxy, arylmethyl, acyl, carboxy, alkoxycarbonyl, thiocarbonyl, cyano, hydroxyl, thiol, alkylthiol, amino, acylated amino, $NO_2$, silyl, and $SO_2R^{10}$;

B is selected from the group consisting of H, halide, trifluoromethylsulfonyl, alkylsulfonate, trifluoromethylsulfonate, aryl-sulfonate, carboxylate, and acetoxy;

M is a metal atom or a metal ion selected from the group consisting of ruthenium rhodium, osmium, iridium, and iron;

XX, YY, and ZZ are each an independently selected atom or group of atoms capable of forming a stable complex; and at least one of X, Y and Z is present; and each of X, Y, and Z is independently a bond, $CH_2$, O, S, NH, $CHR^{11}$, $CR^{11}R^{12}$, or a combination thereof, or two adjacent X, Y or Z form unsaturated carbon-carbon bonds or combinations thereof, and the total linear length of the chain defined by X-Y-Z is two, three or four atoms.

2. The process of claim 1, wherein the reaction is performed in an organic solvent.

3. The process of claim 1, wherein M is ruthenium.

4. The process of claim 1, wherein the total linear length of the chain defined by X-Y-Z is three atoms.

5. The process of claim 1, wherein X, Y and Z each are independently $CH_2$, $CHR^{11}$ $CR^{11}R^{12}$, or a combination thereof.

6. The process of claim 1, wherein the combined electron withdrawing effect generated by $R^{101}$-$R^{106}$ is greater than that generated by $R^1$-$R^5$.

7. The process of claim 1, wherein at least one of $R^1$-$R^5$ is an alkoxy group.

8. The process of claim 1, wherein at least one of $R^{101}$-$R^{106}$ is an electron withdrawing group.

9. The process of claim 1, wherein XX, YY, and ZZ are halides.

10. The process of claim 1, wherein A is $SO_2Ar$ or $SO_2R$, where Ar is aryl and R is alkyl.

11. The process of claim 1, wherein B is a halide.

12. The process of claim 1, wherein the process is performed with exposure to microwaves.

13. A compound of formula (IV)

(IV)

or a salt thereof, wherein
$R^{21}$-$R^{25}$ each independently, or in combination with another of said substituents $R^{21}$-$R^{25}$, form an electron rich or electron donating group or are selected from the group consisting of H, alkyl, aryl, alkoxy, aryloxy, acyloxy, hydroxy, amino, acylamino, thiol, and alkylthiol, each of which is optionally substituted; provided that at least one of $R^{21}$-$R^{25}$ is selected from the group consisting of aryl, alkoxy, aryloxy, acyloxy, hydroxy, amino, acylamino, thiol, and alkylthiol, each of which is optionally substituted;

$R^{26}$-$R^{29}$ are each independently selected from the group consisting of H, halide, alkyl, alkenyl, alkynyl, alkoxy, hydroalkyl, carboalkyl, haloalkyl, aryl, aryloxy, arylmethyl, acyl, carboxy, alkoxycarbonyl, thiocarbonyl, cyano, hydroxyl, thiol, alkylthiol, amino, acylated amino, $NO_2$, silyl, and $SO_2R^{10}$; and A, B, M, X, Y, Z, and $R^{10}$ are as defined in claim 1.

14. The compound of claim 13, wherein X, Y and Z each are independently $CH_2$, $CHR^{11}$ or $CR^{11}R^{12}$, or a combination thereof.

15. The compound of claim 13, wherein at least one of $R^{21}$-$R^{25}$ is an alkoxy group.

16. The compound of claim 13, wherein B is a halide.

17. The compound of claim 13, selected from the group consisting of (a)

(b)

(c)

(d)

(e)

(g)

-continued
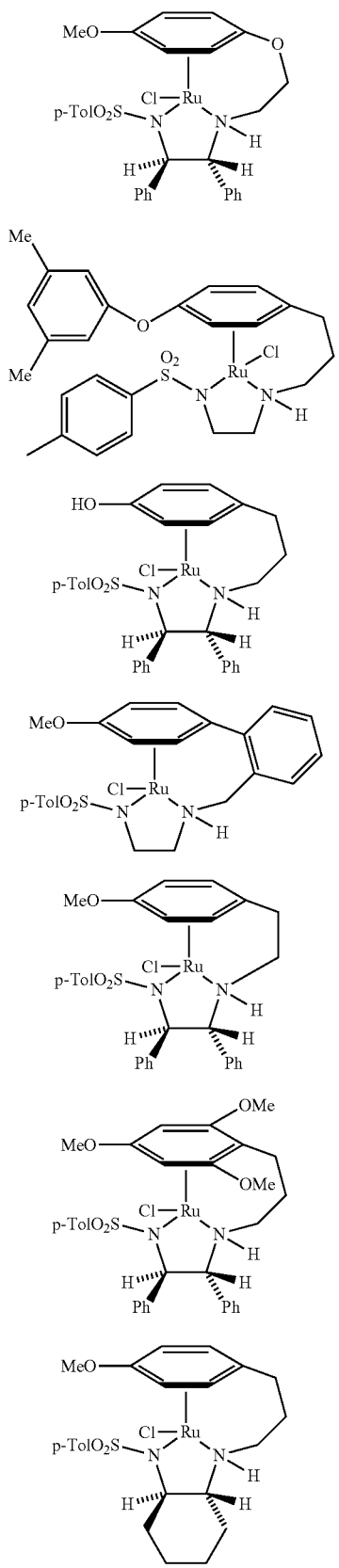
and salts thereof.
18. The compound of claim 13, selected from the group consisting of
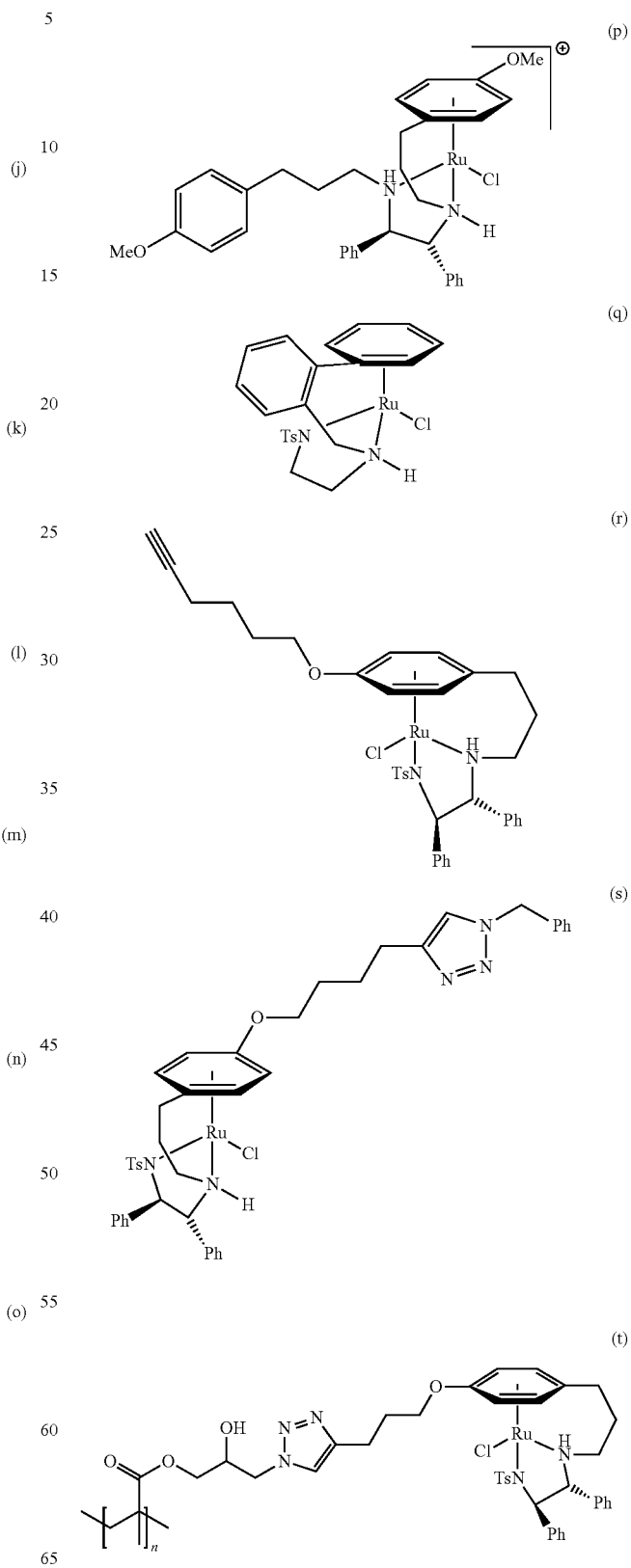

101
-continued

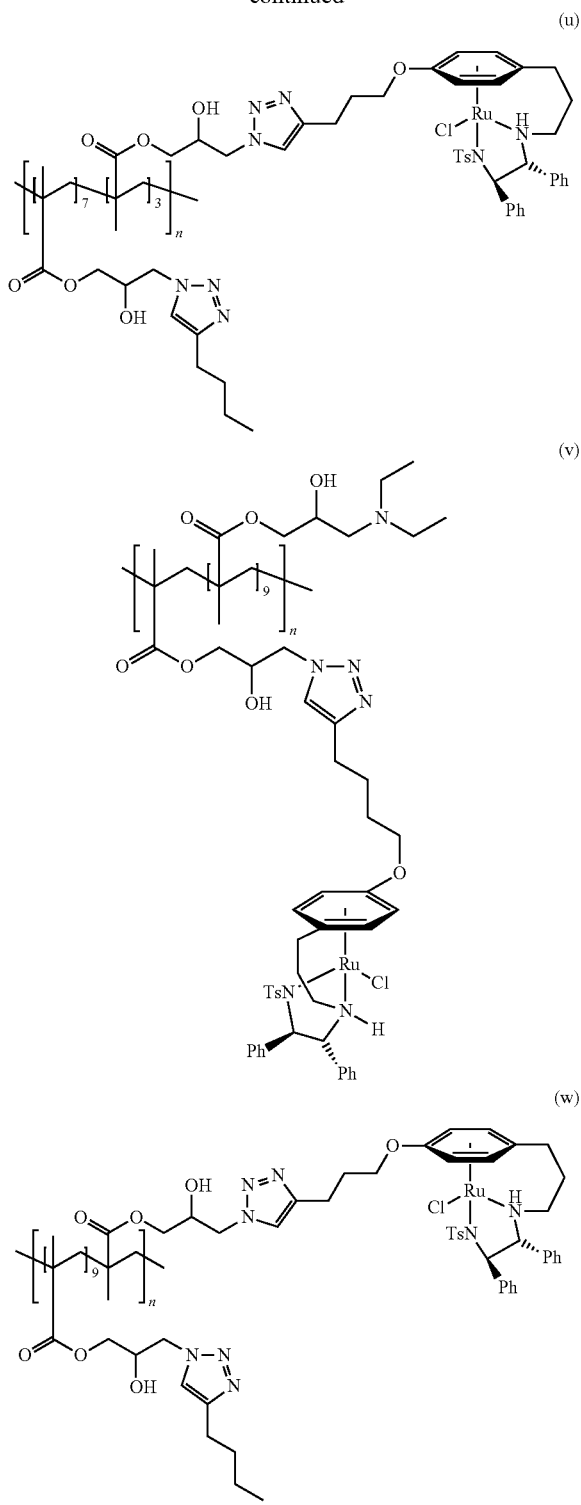

and salts thereof.

19. A process comprising the step of using a compound of claim 13 to catalyse the hydrogenation of a substrate.

20. The compound of claim 13 wherein one of $R^{21}$-$R^{25}$ is a polymer or solid support.

21. A compound of formula (IV)

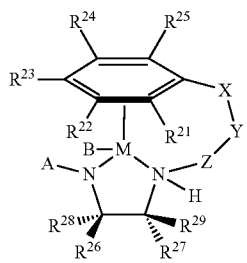

(IV)

or a salt thereof, wherein $R^{21}$-$R^{25}$ each independently, or in combination with another of said substituents $R^{21}$-$R^{25}$, form an electron rich or electron donating group or are selected from the group consisting of H, alkyl, aryl, alkoxy, aryloxy, acyloxy, hydroxy, amino, acylamino, thiol, and alkylthiol, each of which is optionally substituted; provided that at least one of $R^{21}$-$R^{25}$ is an optionally substituted branched alkyl;

$R^{26}$-$R^{29}$ are each independently selected from the group consisting of H, halide, alkyl, alkenyl, alkynyl, alkoxy, hydroalkyl, carboalkyl, haloalkyl, aryl, aryloxy, arylmethyl, acyl, carboxy, alkoxycarbonyl, thiocarbonyl, cyano, hydroxyl, thiol, alkylthiol, amino, acylated amino, $NO_2$, silyl, and $SO_2R^{10}$; and A, B, M, X, Y, Z, and $R^{10}$ are as defined in claim 1.

22. The compound of claim 21, selected from the group consisting of

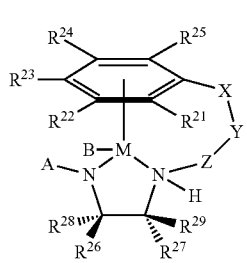

(IV)

and salts thereof.

UNITED STATES PATENT AND TRADEMARK OFFICE
CERTIFICATE OF CORRECTION

PATENT NO.        : 9,321,045 B2
APPLICATION NO.   : 14/440140
DATED             : April 26, 2016
INVENTOR(S)       : Martin Wills It is certified that error appears in the above-identified patent and that said Letters Patent is hereby corrected as shown below:

In the Claims

In Claim 22, column 102, line 40

"   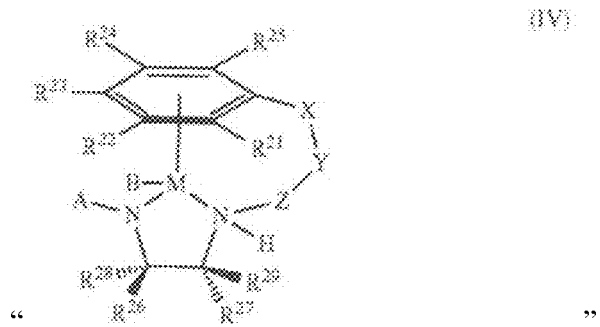   "

should read

--   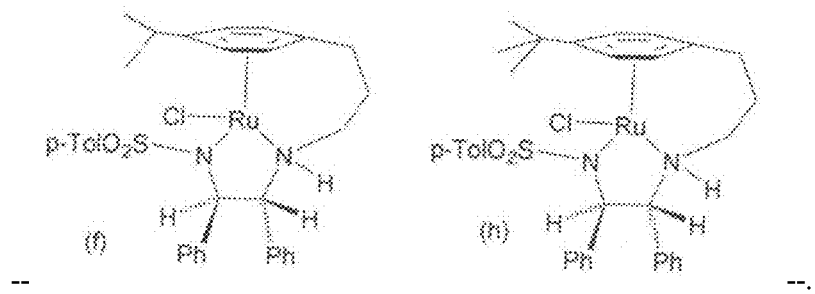   --.

Signed and Sealed this
Fifth Day of July, 2016

Michelle K. Lee
*Director of the United States Patent and Trademark Office*